United States Patent [19]

Kurokawa et al.

[11] Patent Number: 5,571,895
[45] Date of Patent: Nov. 5, 1996

[54] MODIFIED GAF POLYPEPTIDES

[75] Inventors: Tsutomu Kurokawa, Kawanishi; Ken-ichi Kuroshima, Osaka; Sumie Yoshitomi, Osaka; Chisako Seko, Osaka, all of Japan

[73] Assignee: Takeda Chemical Industries, Ltd., Osaka, Japan

[21] Appl. No.: 172,328

[22] Filed: Dec. 21, 1993

[30] Foreign Application Priority Data

Dec. 22, 1992 [JP] Japan .................................. 4-342100
Aug. 23, 1993 [JP] Japan .................................. 5-207719

[51] Int. Cl.⁶ .................................................. C07K 14/475
[52] U.S. Cl. ............................................ 530/399; 530/350
[58] Field of Search ............................... 530/350, 399

[56] References Cited

FOREIGN PATENT DOCUMENTS 0122132  10/1984  European Pat. Off. .
0503297   9/1992  European Pat. Off. .

OTHER PUBLICATIONS

Ken–ichi Naruo et al.; *J. Biol. Chem.*, 268, 2857 (1993).
Masaaki Miyamoto et al., *Mol. Cell Biol.*, 13, 4251 (1993).

*Primary Examiner*—Keith D. Hendricks
*Attorney, Agent, or Firm*—David G. Conlin; David S. Resnick; Dike, Bronstein, Roberts & Cushman

[57] ABSTRACT

The present invention relates to a glia activating factor (GAF) in which 33 to 49 N-terminal amino acids are deleted from the N-terminus of the GAF polypeptide of SEQ ID NO: 3, as well as an anti-GAF antibody which is highly sensitive to assay the GAF and is capable of neutralizing GAF's activity, is produced.

Using the antibody, GAF and its biological activity can be assayed easily with high sensitivity. Further, the neutralizing antibody can be expected to have preventive and curative effects on diseases caused by GAF's excessive action. Furthermore, the GAF polypeptide disclosed herein is more stable to acids and heat than the conventional GAFs, therefore, it can be used as a platelet-increasing agent, etc., more advantageously than the previously known GAFs.

3 Claims, 29 Drawing Sheets

FIG. 1

```
                   N3
                   ┌──▶
Met Ala Pro│Leu Gly Glu Val Gly Asn Tyr Phe Gly Val Gln Asp Ala
 1          5                10                15
Val Pro Phe Gly Asn Val Pro Val Leu Pro Val Asp Ser Pro Val Leu
   N33       20              25              30
   ┌──▶
Leu│Ser Asp His Leu Gly Gln Ser Glu Ala Gly Gly Leu Pro Arg Gly
   N49    35              40              45
   ┌──▶
Pro│Ala Val Thr Asp Leu Asp His Leu Lys Gly Ile Leu Arg Arg Arg
    50              55              60
Gln Leu Tyr Cys Arg Thr Gly Phe His Leu Glu Ile Phe Pro Asn Gly
 65              70              75              80
Thr Ile Gln Gly Thr Arg Lys Asp His Ser Arg Phe Gly Ile Leu Glu
             85              90              95
Phe Ile Ser Ile Ala Val Gly Leu Val Ser Ile Arg Gly Val Asp Ser
            100             105             110
Gly Leu Tyr Leu Gly Met Asn Glu Lys Gly Glu Leu Tyr Gly Ser Glu
            115             120             125
Lys Leu Thr Gln Glu Cys Val Phe Arg Glu Gln Phe Glu Glu Asn Trp
            130             135             140
Tyr Asn Thr Tyr Ser Ser Asn Leu Tyr Lys His Val Asp Thr Gly Arg
            145             150             155             160
Arg Tyr Tyr Val Ala Leu Asn Lys Asp Gly Thr Pro Arg Glu Gly Thr
                 165             170             175
Arg Thr Lys Arg His Gln Lys Phe Thr His Phe Leu Pro Arg Pro Val
             180             185             190
Asp Pro Asp Lys Val Pro Glu Leu Tyr Lys Asp Ile Leu Ser Gln Ser
             195             200             205     208
```

```
* 5'-TATGTTAGGTGAAGTTGGGAACTATTTCGGTGTGCAGGATGCGGTAC-3'
     ACAATCCACTTCAACCCTTGATAAAGCCACACGTCCTACGC
```

(SEQ ID NO: 10)
(SEQ ID NO: 11)

\*5' TATGAGTGACCACCTGGGTCAGTCCGAAGCAGGGGGGCTCCCCAGGGGACCCGCAGTCACGGACTTGGATCATTT 3'
3' ACTCACTGGTGGACCCAGTCAGGCTTCGTCCCCCCGAGGGGTCCCCTGGGCGTCAGTGCCTGAACCTAGTAAA 5'

(SEQ ID NO: 12)
(SEQ ID NO: 13)

** p<0.01
§ p<0.05

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( E ) HAPLOTYPE: 2n
        ( F ) TISSUE TYPE: Skin
        ( G ) CELL TYPE: Fibroblast ( v i i ) IMMEDIATE SOURCE:
        ( A ) LIBRARY: Human foreskin cDNA library
        ( B ) CLONE: pGAF1

( x i ) SEQUENCE DESCRIPTION: SEQ ID NO:1:

```
Leu Asp His Leu Lys Gly Ile Leu Arg Arg Arg Gln Leu Tyr Cys Arg
  1               5                  10                  15
Thr Gly Phe His Leu Glu Ile Phe Pro Asn Gly Thr Ile Gln Gly Thr
                 20                  25                  30
Arg Lys Asp His Ser Arg Phe Gly Ile Leu Glu Phe Ile Ser Ile Ala
             35                  40                  45
Val Gly Leu Val Ser Ile Arg Gly Val Asp Ser Gly Leu Tyr Leu Gly
     50                  55                  60
Met Asn Glu Lys Gly Glu Leu Tyr Gly Ser Glu Lys Leu Thr Gln Glu
 65                  70                  75                  80
Cys Val Phe Arg Glu Gln Phe Glu Glu Asn Trp Tyr Asn Thr Tyr Ser
                 85                  90                  95
Ser Asn Leu Tyr Lys His Val Asp Thr Gly Arg Arg Tyr Tyr Val Ala
                100                 105                 110
Leu Asn Lys Asp Gly Thr Pro Arg Glu Gly Thr Arg Thr Lys Arg His
            115                 120                 125
```

```
            Gln  Lys  Phe  Thr  His  Phe  Leu  Pro  Arg  Pro  Val  Asp  Pro  Asp
                 130                 135                      140
```

(2) INFORMATION FOR SEQ ID NO:2:

(i) SEQUENCE CHARACTERISTICS:
        (A) LENGTH: 207 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Homo sapiens
        (E) HAPLOTYPE: 2n
        (F) TISSUE TYPE: Skin
        (G) CELL TYPE: Fibroblast (vii) IMMEDIATE SOURCE:
        (A) LIBRARY: Human foreskin cDNA library
        (B) CLONE: pGAF1

(xi) SEQUENCE DESCRIPTION: SEQ ID NO:2:

```
Ala  Pro  Leu  Gly  Glu  Val  Gly  Asn  Tyr  Phe  Gly  Val  Gln  Asp  Ala  Val
 1              5                        10                       15

Pro  Phe  Gly  Asn  Val  Pro  Val  Leu  Pro  Val  Asp  Ser  Pro  Val  Leu  Leu
               20                    25                       30

Ser  Asp  His  Leu  Gly  Gln  Ser  Glu  Ala  Gly  Gly  Leu  Pro  Arg  Gly  Pro
          35                    40                       45

Ala  Val  Thr  Asp  Leu  Asp  His  Leu  Lys  Gly  Ile  Leu  Arg  Arg  Arg  Gln
     50                    55                       60

Leu  Tyr  Cys  Arg  Thr  Gly  Phe  His  Leu  Glu  Ile  Phe  Pro  Asn  Gly  Thr
65                     70                       75                        80

Ile  Gln  Gly  Thr  Arg  Lys  Asp  His  Ser  Arg  Phe  Gly  Ile  Leu  Glu  Phe
                    85                       90                       95

Ile  Ser  Ile  Ala  Val  Gly  Leu  Val  Ser  Ile  Arg  Gly  Val  Asp  Ser  Gly
               100                   105                      110

Leu  Tyr  Leu  Gly  Met  Asn  Glu  Lys  Gly  Glu  Leu  Tyr  Gly  Ser  Glu  Lys
          115                   120                      125

Leu  Thr  Gln  Glu  Cys  Val  Phe  Arg  Glu  Gln  Phe  Glu  Glu  Asn  Trp  Tyr
     130                   135                      140

Asn  Thr  Tyr  Ser  Ser  Asn  Leu  Tyr  Lys  His  Val  Asp  Thr  Gly  Arg  Arg
145                   150                      155                      160

Tyr  Tyr  Val  Ala  Leu  Asn  Lys  Asp  Gly  Thr  Pro  Arg  Glu  Gly  Thr  Arg
               165                   170                      175

Thr  Lys  Arg  His  Gln  Lys  Phe  Thr  His  Phe  Leu  Pro  Arg  Pro  Val  Asp
          180                   185                      190

Pro  Asp  Lys  Val  Pro  Glu  Leu  Tyr  Lys  Asp  Ile  Leu  Ser  Gln  Ser
          195                   200                      205
```

(2) INFORMATION FOR SEQ ID NO:3:

(i) SEQUENCE CHARACTERISTICS:
        (A) LENGTH: 208 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Homo sapiens (E) HAPLOTYPE: 2n
(F) TISSUE TYPE: Skin
(G) CELL TYPE: Fibroblast (vii) IMMEDIATE SOURCE:
(A) LIBRARY: Human foreskin cDNA library
(B) CLONE: pGAF1

(xi) SEQUENCE DESCRIPTION: SEQ ID NO:3:

| Met | Ala | Pro | Leu | Gly | Glu | Val | Gly | Asn | Tyr | Phe | Gly | Val | Gln | Asp | Ala |
|---|---|---|---|---|---|---|---|---|---|---|---|---|---|---|---|
| 1 | | | | 5 | | | | | 10 | | | | | 15 | |

| Val | Pro | Phe | Gly | Asn | Val | Pro | Val | Leu | Pro | Val | Asp | Ser | Pro | Val | Leu |
|---|---|---|---|---|---|---|---|---|---|---|---|---|---|---|---|
| | | | 20 | | | | | 25 | | | | | 30 | | |

| Leu | Ser | Asp | His | Leu | Gly | Gln | Ser | Glu | Ala | Gly | Gly | Leu | Pro | Arg | Gly |
|---|---|---|---|---|---|---|---|---|---|---|---|---|---|---|---|
| | | 35 | | | | | 40 | | | | | 45 | | | |

| Pro | Ala | Val | Thr | Asp | Leu | Asp | His | Leu | Lys | Gly | Ile | Leu | Arg | Arg | Arg |
|---|---|---|---|---|---|---|---|---|---|---|---|---|---|---|---|
| | 50 | | | | | 55 | | | | | 60 | | | | |

| Gln | Leu | Tyr | Cys | Arg | Thr | Gly | Phe | His | Leu | Glu | Ile | Phe | Pro | Asn | Gly |
|---|---|---|---|---|---|---|---|---|---|---|---|---|---|---|---|
| 65 | | | | | 70 | | | | | 75 | | | | | 80 |

| Thr | Ile | Gln | Gly | Thr | Arg | Lys | Asp | His | Ser | Arg | Phe | Gly | Ile | Leu | Glu |
|---|---|---|---|---|---|---|---|---|---|---|---|---|---|---|---|
| | | | | 85 | | | | | 90 | | | | | 95 | |

| Phe | Ile | Ser | Ile | Ala | Val | Gly | Leu | Val | Ser | Ile | Arg | Gly | Val | Asp | Ser |
|---|---|---|---|---|---|---|---|---|---|---|---|---|---|---|---|
| | | | 100 | | | | | 105 | | | | | 110 | | |

| Gly | Leu | Tyr | Leu | Gly | Met | Asn | Glu | Lys | Gly | Glu | Leu | Tyr | Gly | Ser | Glu |
|---|---|---|---|---|---|---|---|---|---|---|---|---|---|---|---|
| | | 115 | | | | | 120 | | | | | 125 | | | |

| Lys | Leu | Thr | Gln | Glu | Cys | Val | Phe | Arg | Glu | Gln | Phe | Glu | Glu | Asn | Trp |
|---|---|---|---|---|---|---|---|---|---|---|---|---|---|---|---|
| | 130 | | | | | 135 | | | | | 140 | | | | |

| Tyr | Asn | Thr | Tyr | Ser | Ser | Asn | Leu | Tyr | Lys | His | Val | Asp | Thr | Gly | Arg |
|---|---|---|---|---|---|---|---|---|---|---|---|---|---|---|---|
| 145 | | | | | 150 | | | | | 155 | | | | | 160 |

| Arg | Tyr | Tyr | Val | Ala | Leu | Asn | Lys | Asp | Gly | Thr | Pro | Arg | Glu | Gly | Thr |
|---|---|---|---|---|---|---|---|---|---|---|---|---|---|---|---|
| | | | | 165 | | | | | 170 | | | | | 175 | |

| Arg | Thr | Lys | Arg | His | Gln | Lys | Phe | Thr | His | Phe | Leu | Pro | Arg | Pro | Val |
|---|---|---|---|---|---|---|---|---|---|---|---|---|---|---|---|
| | | | 180 | | | | | 185 | | | | | 190 | | |

| Asp | Pro | Asp | Lys | Val | Pro | Glu | Leu | Tyr | Lys | Asp | Ile | Leu | Ser | Gln | Ser |
|---|---|---|---|---|---|---|---|---|---|---|---|---|---|---|---|
| | | 195 | | | | | 200 | | | | | 205 | | | |

(2) INFORMATION FOR SEQ ID NO:4:

(i) SEQUENCE CHARACTERISTICS:
(A) LENGTH: 205 amino acids
(B) TYPE: amino acid
(D) TOPOLOGY: linear (ii) MOLECULE TYPE: protein (iii) HYPOTHETICAL: NO (vi) ORIGINAL SOURCE:
(A) ORGANISM: Homo sapiens
(E) HAPLOTYPE: 2n
(F) TISSUE TYPE: Skin
(G) CELL TYPE: Fibroblast (vii) IMMEDIATE SOURCE:
(A) LIBRARY: Human foreskin cDNA library
(B) CLONE: pGAF1

(xi) SEQUENCE DESCRIPTION: SEQ ID NO:4:

| Leu | Gly | Glu | Val | Gly | Asn | Tyr | Phe | Gly | Val | Gln | Asp | Ala | Val | Pro | Phe |
|---|---|---|---|---|---|---|---|---|---|---|---|---|---|---|---|
| 1 | | | | 5 | | | | | 10 | | | | | 15 | |

| Gly | Asn | Val | Pro | Val | Leu | Pro | Val | Asp | Ser | Pro | Val | Leu | Leu | Ser | Asp |
|---|---|---|---|---|---|---|---|---|---|---|---|---|---|---|---|
| | | | 20 | | | | | 25 | | | | | 30 | | |

| His | Leu | Gly | Gln | Ser | Glu | Ala | Gly | Gly | Leu | Pro | Arg | Gly | Pro | Ala | Val |

|  | 35 |  |  |  | 40 |  |  |  | 45 |  |  |  |
|---|---|---|---|---|---|---|---|---|---|---|---|---|

Thr Asp Leu Asp His Leu Lys Gly Ile Leu Arg Arg Gln Leu Tyr
    50              55                  60

Cys Arg Thr Gly Phe His Leu Glu Ile Phe Pro Asn Gly Thr Ile Gln
65              70                  75                      80

Gly Thr Arg Lys Asp His Ser Arg Phe Gly Ile Leu Glu Phe Ile Ser
            85                  90                      95

Ile Ala Val Gly Leu Val Ser Ile Arg Gly Val Asp Ser Gly Leu Tyr
            100                 105                 110

Leu Gly Met Asn Glu Lys Gly Glu Leu Tyr Gly Ser Glu Lys Leu Thr
        115                 120                 125

Gln Glu Cys Val Phe Arg Glu Gln Phe Glu Glu Asn Trp Tyr Asn Thr
    130                 135                 140

Tyr Ser Ser Asn Leu Tyr Lys His Val Asp Thr Gly Arg Arg Tyr Tyr
145                 150                 155                 160

Val Ala Leu Asn Lys Asp Gly Thr Pro Arg Glu Gly Thr Arg Thr Lys
                165                 170                 175

Arg His Gln Lys Phe Thr His Phe Leu Pro Arg Pro Val Asp Pro Asp
            180                 185                 190

Lys Val Pro Glu Leu Tyr Lys Asp Ile Leu Ser Gln Ser
        195                 200                 205

( 2 ) INFORMATION FOR SEQ ID NO:5:

( i ) SEQUENCE CHARACTERISTICS:
        ( A ) LENGTH: 206 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( E ) HAPLOTYPE: 2n
        ( F ) TISSUE TYPE: Skin
        ( G ) CELL TYPE: Fibroblast ( v i i ) IMMEDIATE SOURCE:
        ( A ) LIBRARY: Human foreskin cDNA library
        ( B ) CLONE: pGAF1

( x i ) SEQUENCE DESCRIPTION: SEQ ID NO:5:

Met Leu Gly Glu Val Gly Asn Tyr Phe Gly Val Gln Asp Ala Val Pro
1               5                   10                  15

Phe Gly Asn Val Pro Val Leu Pro Val Asp Ser Pro Val Leu Leu Ser
            20                  25                  30

Asp His Leu Gly Gln Ser Glu Ala Gly Gly Leu Pro Arg Gly Pro Ala
        35                  40                  45

Val Thr Asp Leu Asp His Leu Lys Gly Ile Leu Arg Arg Arg Gln Leu
    50                  55                  60

Tyr Cys Arg Thr Gly Phe His Leu Glu Ile Phe Pro Asn Gly Thr Ile
65                  70                  75                  80

Gln Gly Thr Arg Lys Asp His Ser Arg Phe Gly Ile Leu Glu Phe Ile
                85                  90                  95

Ser Ile Ala Val Gly Leu Val Ser Ile Arg Gly Val Asp Ser Gly Leu
            100                 105                 110

Tyr Leu Gly Met Asn Glu Lys Gly Glu Leu Tyr Gly Ser Glu Lys Leu
        115                 120                 125

```
Thr  Gln  Glu  Cys  Val  Phe  Arg  Glu  Gln  Phe  Glu  Glu  Asn  Trp  Tyr  Asn
     130                      135                 140

Thr  Tyr  Ser  Ser  Asn  Leu  Tyr  Lys  His  Val  Asp  Thr  Gly  Arg  Arg  Tyr
145                      150                      155                           160

Tyr  Val  Ala  Leu  Asn  Lys  Asp  Gly  Thr  Pro  Arg  Glu  Gly  Thr  Arg  Thr
               165                           170                      175

Lys  Arg  His  Gln  Lys  Phe  Thr  His  Phe  Leu  Pro  Arg  Pro  Val  Asp  Pro
               180                      185                      190

Asp  Lys  Val  Pro  Glu  Leu  Tyr  Lys  Asp  Ile  Leu  Ser  Gln  Ser
          195                      200                      205
```

( 2 ) INFORMATION FOR SEQ ID NO:6:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( i v ) ANTI-SENSE: NO ( v i ) ORIGINAL SOURCE:
        ( A ) ORGANISM: Homo sapiens
        ( E ) HAPLOTYPE: 2n
        ( F ) TISSUE TYPE: Skin
        ( G ) CELL TYPE: Fibroblast ( v i i ) IMMEDIATE SOURCE:
        ( A ) LIBRARY: Human foreskin cDNA library
        ( B ) CLONE: pGAF1

( x i ) SEQUENCE DESCRIPTION: SEQ ID NO:6:

```
Ser  Asp  His  Leu  Gly  Gln  Ser  Glu  Ala  Gly  Gly  Leu  Pro  Arg  Gly  Pro
1              5                        10                      15

Ala  Val  Thr  Asp  Leu  Asp  His  Leu  Lys  Gly  Ile  Leu  Arg  Arg  Arg  Gln
               20                      25                      30

Leu  Tyr  Cys  Arg  Thr  Gly  Phe  His  Leu  Glu  Ile  Phe  Pro  Asn  Gly  Thr
          35                      40                      45

Ile  Gln  Gly  Thr  Arg  Lys  Asp  His  Ser  Arg  Phe  Gly  Ile  Leu  Glu  Phe
     50                      55                      60

Ile  Ser  Ile  Ala  Val  Gly  Leu  Val  Ser  Ile  Arg  Gly  Val  Asp  Ser  Gly
65                       70                      75                           80

Leu  Tyr  Leu  Gly  Met  Asn  Glu  Lys  Gly  Glu  Leu  Tyr  Gly  Ser  Glu  Lys
               85                      90                      95

Leu  Thr  Gln  Glu  Cys  Val  Phe  Arg  Glu  Gln  Phe  Glu  Glu  Asn  Trp  Tyr
               100                     105                     110

Asn  Thr  Tyr  Ser  Ser  Asn  Leu  Tyr  Lys  His  Val  Asp  Thr  Gly  Arg  Arg
          115                     120                     125

Tyr  Tyr  Val  Ala  Leu  Asn  Lys  Asp  Gly  Thr  Pro  Arg  Glu  Gly  Thr  Arg
     130                     135                     140

Thr  Lys  Arg  His  Gln  Lys  Phe  Thr  His  Phe  Leu  Pro  Arg  Pro  Val  Asp
145                     150                     155                          160

Pro  Asp  Lys  Val  Pro  Glu  Leu  Tyr  Lys  Asp  Ile  Leu  Ser  Gln  Ser
               165                     170                     175
```

( 2 ) INFORMATION FOR SEQ ID NO:7:

( i ) SEQUENCE CHARACTERISTICS:
        ( A ) LENGTH: 176 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
    ( A ) ORGANISM: Homo sapiens
    ( E ) HAPLOTYPE: 2n
    ( F ) TISSUE TYPE: Skin
    ( G ) CELL TYPE: Fibroblast ( v i i ) IMMEDIATE SOURCE:
    ( A ) LIBRARY: Human foreskin cDNA library
    ( B ) CLONE: pGAF1

( x i ) SEQUENCE DESCRIPTION: SEQ ID NO:7:

```
Met  Ser  Asp  His  Leu  Gly  Gln  Ser  Glu  Ala  Gly  Gly  Leu  Pro  Arg  Gly
1                   5                   10                  15

Pro  Ala  Val  Thr  Asp  Leu  Asp  His  Leu  Lys  Gly  Ile  Leu  Arg  Arg  Arg
               20                  25                  30

Gln  Leu  Tyr  Cys  Arg  Thr  Gly  Phe  His  Leu  Glu  Ile  Phe  Pro  Asn  Gly
          35                  40                  45

Thr  Ile  Gln  Gly  Thr  Arg  Lys  Asp  His  Ser  Arg  Phe  Gly  Ile  Leu  Glu
     50                  55                  60

Phe  Ile  Ser  Ile  Ala  Val  Gly  Leu  Val  Ser  Ile  Arg  Gly  Val  Asp  Ser
65                  70                  75                  80

Gly  Leu  Tyr  Leu  Gly  Met  Asn  Glu  Lys  Gly  Glu  Leu  Tyr  Gly  Ser  Glu
               85                  90                  95

Lys  Leu  Thr  Gln  Glu  Cys  Val  Phe  Arg  Glu  Gln  Phe  Glu  Glu  Asn  Trp
               100                 105                 110

Tyr  Asn  Thr  Tyr  Ser  Ser  Asn  Leu  Tyr  Lys  His  Val  Asp  Thr  Gly  Arg
          115                 120                 125

Arg  Tyr  Tyr  Val  Ala  Leu  Asn  Lys  Asp  Gly  Thr  Pro  Arg  Glu  Gly  Thr
     130                 135                 140

Arg  Thr  Lys  Arg  His  Gln  Lys  Phe  Thr  His  Phe  Leu  Pro  Arg  Pro  Val
145                 150                 155                 160

Asp  Pro  Asp  Lys  Val  Pro  Glu  Leu  Tyr  Lys  Asp  Ile  Leu  Ser  Gln  Ser
               165                 170                 175
```

( 2 ) INFORMATION FOR SEQ ID NO:8:

( i ) SEQUENCE CHARACTERISTICS:
    ( A ) LENGTH: 159 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( A ) ORGANISM: Homo sapiens
    ( E ) HAPLOTYPE: 2n
    ( F ) TISSUE TYPE: Skin
    ( G ) CELL TYPE: Fibroblast ( v i i ) IMMEDIATE SOURCE:
    ( A ) LIBRARY: Human foreskin cDNA library
    ( B ) CLONE: pGAF1

( x i ) SEQUENCE DESCRIPTION: SEQ ID NO:8:

```
Ala  Val  Thr  Asp  Leu  Asp  His  Leu  Lys  Gly  Ile  Leu  Arg  Arg  Arg  Gln
1                   5                   10                  15

Leu  Tyr  Cys  Arg  Thr  Gly  Phe  His  Leu  Glu  Ile  Phe  Pro  Asn  Gly  Thr
               20                  25                  30

Ile  Gln  Gly  Thr  Arg  Lys  Asp  His  Ser  Arg  Phe  Gly  Ile  Leu  Glu  Phe
```

|  |  |  |  | 35 |  |  |  | 40 |  |  |  | 45 |  |  |
|---|---|---|---|---|---|---|---|---|---|---|---|---|---|---|
| Ile | Ser | Ile | Ala | Val | Gly | Leu | Val | Ser | Ile | Arg | Gly | Val | Asp | Ser | Gly |
|  | 50 |  |  |  | 55 |  |  |  |  |  | 60 |  |  |  |  |
| Leu | Tyr | Leu | Gly | Met | Asn | Glu | Lys | Gly | Glu | Leu | Tyr | Gly | Ser | Glu | Lys |
| 65 |  |  |  |  | 70 |  |  |  |  | 75 |  |  |  |  | 80 |
| Leu | Thr | Gln | Glu | Cys | Val | Phe | Arg | Glu | Gln | Phe | Glu | Glu | Asn | Trp | Tyr |
|  |  |  |  | 85 |  |  |  |  | 90 |  |  |  |  | 95 |  |
| Asn | Thr | Tyr | Ser | Ser | Asn | Leu | Tyr | Lys | His | Val | Asp | Thr | Gly | Arg | Arg |
|  |  |  | 100 |  |  |  |  | 105 |  |  |  |  | 110 |  |  |
| Tyr | Tyr | Val | Ala | Leu | Asn | Lys | Asp | Gly | Thr | Pro | Arg | Glu | Gly | Thr | Arg |
|  |  | 115 |  |  |  |  | 120 |  |  |  |  | 125 |  |  |  |
| Thr | Lys | Arg | His | Gln | Lys | Phe | Thr | His | Phe | Leu | Pro | Arg | Pro | Val | Asp |
|  | 130 |  |  |  |  | 135 |  |  |  |  | 140 |  |  |  |  |
| Pro | Asp | Lys | Val | Pro | Glu | Leu | Tyr | Lys | Asp | Ile | Leu | Ser | Gln | Ser |  |
| 145 |  |  |  |  | 150 |  |  |  |  | 155 |  |  |  |  |  |

( 2 ) INFORMATION FOR SEQ ID NO:9:

( i ) SEQUENCE CHARACTERISTICS:
  ( A ) LENGTH: 160 amino acids
  ( B ) TYPE: amino acid
  ( D ) TOPOLOGY: linear ( i i ) MOLECULE TYPE: protein ( i i i ) HYPOTHETICAL: NO ( v i ) ORIGINAL SOURCE:
  ( A ) ORGANISM: Homo sapiens
  ( E ) HAPLOTYPE: 2n
  ( F ) TISSUE TYPE: Skin
  ( G ) CELL TYPE: Fibroblast ( v i i ) IMMEDIATE SOURCE:
  ( A ) LIBRARY: Human foreskin cDNA library
  ( B ) CLONE: pGAF1

( x i ) SEQUENCE DESCRIPTION: SEQ ID NO:9:

| Met | Ala | Val | Thr | Asp | Leu | Asp | His | Leu | Lys | Gly | Ile | Leu | Arg | Arg | Arg |
|---|---|---|---|---|---|---|---|---|---|---|---|---|---|---|---|
| 1 |  |  |  | 5 |  |  |  |  | 10 |  |  |  |  | 15 |  |
| Gln | Leu | Tyr | Cys | Arg | Thr | Gly | Phe | His | Leu | Glu | Ile | Phe | Pro | Asn | Gly |
|  |  |  | 20 |  |  |  |  | 25 |  |  |  |  | 30 |  |  |
| Thr | Ile | Gln | Gly | Thr | Arg | Lys | Asp | His | Ser | Arg | Phe | Gly | Ile | Leu | Glu |
|  |  |  | 35 |  |  |  |  | 40 |  |  |  |  | 45 |  |  |
| Phe | Ile | Ser | Ile | Ala | Val | Gly | Leu | Val | Ser | Ile | Arg | Gly | Val | Asp | Ser |
|  |  |  | 50 |  |  |  |  | 55 |  |  |  |  | 60 |  |  |
| Gly | Leu | Tyr | Leu | Gly | Met | Asn | Glu | Lys | Gly | Glu | Leu | Tyr | Gly | Ser | Glu |
| 65 |  |  |  |  | 70 |  |  |  |  | 75 |  |  |  |  | 80 |
| Lys | Leu | Thr | Gln | Glu | Cys | Val | Phe | Arg | Glu | Gln | Phe | Glu | Glu | Asn | Trp |
|  |  |  |  | 85 |  |  |  |  | 90 |  |  |  |  | 95 |  |
| Tyr | Asn | Thr | Tyr | Ser | Ser | Asn | Leu | Tyr | Lys | His | Val | Asp | Thr | Gly | Arg |
|  |  |  | 100 |  |  |  |  | 105 |  |  |  |  | 110 |  |  |
| Arg | Tyr | Tyr | Val | Ala | Leu | Asn | Lys | Asp | Gly | Thr | Pro | Arg | Glu | Gly | Thr |
|  |  | 115 |  |  |  |  | 120 |  |  |  |  | 125 |  |  |  |
| Arg | Thr | Lys | Arg | His | Gln | Lys | Phe | Thr | His | Phe | Leu | Pro | Arg | Pro | Val |
|  | 130 |  |  |  |  | 135 |  |  |  |  | 140 |  |  |  |  |
| Asp | Pro | Asp | Lys | Val | Pro | Glu | Leu | Tyr | Lys | Asp | Ile | Leu | Ser | Gln | Ser |
| 145 |  |  |  |  | 150 |  |  |  |  | 155 |  |  |  |  | 160 |

( 2 ) INFORMATION FOR SEQ ID NO:10:

( i ) SEQUENCE CHARACTERISTICS:
 ( A ) LENGTH: 47 base pairs
 ( B ) TYPE: nucleic acid
 ( C ) STRANDEDNESS: single
 ( D ) TOPOLOGY: linear ( i i ) MOLECULE TYPE: other nucleic acid, synthetic DNA ( i i i ) HYPOTHETICAL: NO ( i v ) ANTI-SENSE: NO ( x i ) SEQUENCE DESCRIPTION: SEQ ID NO:10:

TATGTTAGGT GAAGTTGGGA ACTATTTCGG TGTGCAGGAT GCGGTAC  47

( 2 ) INFORMATION FOR SEQ ID NO:11:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: other nucleic acid, synthetic DNA ( i i i ) HYPOTHETICAL: NO ( i v ) ANTI-SENSE: YES ( x i ) SEQUENCE DESCRIPTION: SEQ ID NO:11:

CGCATCCTGC ACACCGAAAT AGTTCCCAAC TTCACCTAAC A  41

( 2 ) INFORMATION FOR SEQ ID NO:12:

( i ) SEQUENCE CHARACTERISTICS:
  ( A ) LENGTH: 75 base pairs
  ( B ) TYPE: nucleic acid
  ( C ) STRANDEDNESS: single
  ( D ) TOPOLOGY: linear ( i i ) MOLECULE TYPE: other nucleic acid, synthetic DNA ( i i i ) HYPOTHETICAL: NO ( i v ) ANTI-SENSE: NO ( x i ) SEQUENCE DESCRIPTION: SEQ ID NO:12:

TATGAGTGAC CACCTGGGTC AGTCCGAAGC AGGGGGCTC CCCAGGGGAC CCGCAGTCAC  60

GGACTTGGAT CATTT  75

( 2 ) INFORMATION FOR SEQ ID NO:13:

( i ) SEQUENCE CHARACTERISTICS:
  ( A ) LENGTH: 73 base pairs
  ( B ) TYPE: nucleic acid
  ( C ) STRANDEDNESS: single
  ( D ) TOPOLOGY: linear ( i i ) MOLECULE TYPE: other nucleic acid, synthetic DNA ( i i i ) HYPOTHETICAL: NO ( i v ) ANTI-SENSE: YES ( x i ) SEQUENCE DESCRIPTION: SEQ ID NO:13:

AAATGATCCA AGTCCGTGAC TGCGGGTCCC CTGGGGAGCC CCCCTGCTTC GGACTGACCC  60

AGGTGGTCAC TCA  73

MODIFIED GAF POLYPEPTIDES

FIELD OF THE INVENTION

The present invention relates to an antibody which highly sensitively recognizes a glia activating factor (hereinafter, "GAF") polypeptide and neutralizes biological activity thereof by binding with the factor, a hybridoma producing the antibody, a method for the production of the hybridoma and its use. Further, the present invention relates to an excellent GAF polypeptide specified by a specific amino acid sequence, a method for the production thereof and its use.

BACKGROUND OF THE INVENTION

GAF is a growth factor composed of a heparin-binding polypeptide having a molecular weight of about 30,000 as a whole molecular type, the polypeptide being first separated from glioma cells by purification [K. Naruo et al., *J. Biol. Chem.*, 268, 2857 (1993)]. The amino acid sequence thereof (FIG. 1) has proved that GAF is one member of the family of fibroblast growth factors (hereinafter, "FGFs"). GAF having about 30% homology with each factor of the FGF family in the amino acid sequence is called "FGF9" [M. Miyamoto et al., *Mol. Cell. Biol.*, 13, 4251 (1993)]. The GAF is considered to activate mesodermal cells such as fibroblasts, glial cells and nerve cells. Further, abnormal continuous expression thereof conceivably may lead to the malignant transformation of cells which are reactive to the factor. It is therefore conceivable that an antibody inhibiting GAF's activity can be used as a drug for suppressing progress of diseases such as tumors. The assay of the blood GAF level is also considered to be necessary as one means for diagnosing these diseases. Furthermore, GAF exhibits growth promoting activity upon widely ranging cells including osteoblasts, hepatocites and vascular smooth muscle cells. Accordingly, it is expected that GAF can be widely utilized as a bone formation accelerant, etc. In addition, it has been discovered that GAF acts on megakaryoblasts to promote their growth, thereby increasing the platelets in number. Hence, GAF is also expected to be applied as a platelet-increasing agent.

The assay of the blood GAF level is indispensable for tracing thereof when GAF is administered to, for example, patients with thrombocytopenia.

On the other hand, GAF can be produced by use of host cells such as various microorganisms including *Escherichia coli* or animal cultured cells, employing recombinant technology, based on the cDNA sequence previously reported, and can be used similarly with natural extracts. However, GAF has an easily decomposable moiety on the N-terminal side, and contamination with the decomposed product makes it difficult to purify GAF. The region of this easily decomposable moiety has not been determined yet. Further, GAF is not so stable, for example, stability to acids or stability to heat, which results in disadvantages in the application for various drugs.

SUMMARY OF THE INVENTION

In view of these situations, the present inventors have succeeded in preparing antibodies which make possible a high sensitive assay for GAF and which is capable of neutralizing GAF activity. As a result of further intensive investigation into various GAF polypeptides, the present inventors have succeeded in preparing GAF polypeptides improved in stability and biological activity by deleting 33 to 49 amino acid residues from N-terminus of the GAF polypeptide sequence represented by SEQ ID NO: 3. Based on these findings, the present inventors have further conducted investigation, thus completing the present invention.

BRIEF DESCRIPTION OF THE DRAWINGS

FIG. 1 shows a whole amino acid sequence of human GAF.

*, **: The significant difference test was carried out to the group to which GAF N33 was given, for each group to which each antibody was given (*: $p<0.05$, **: $p<0.01$, Dunnett's test).

Figure 21:
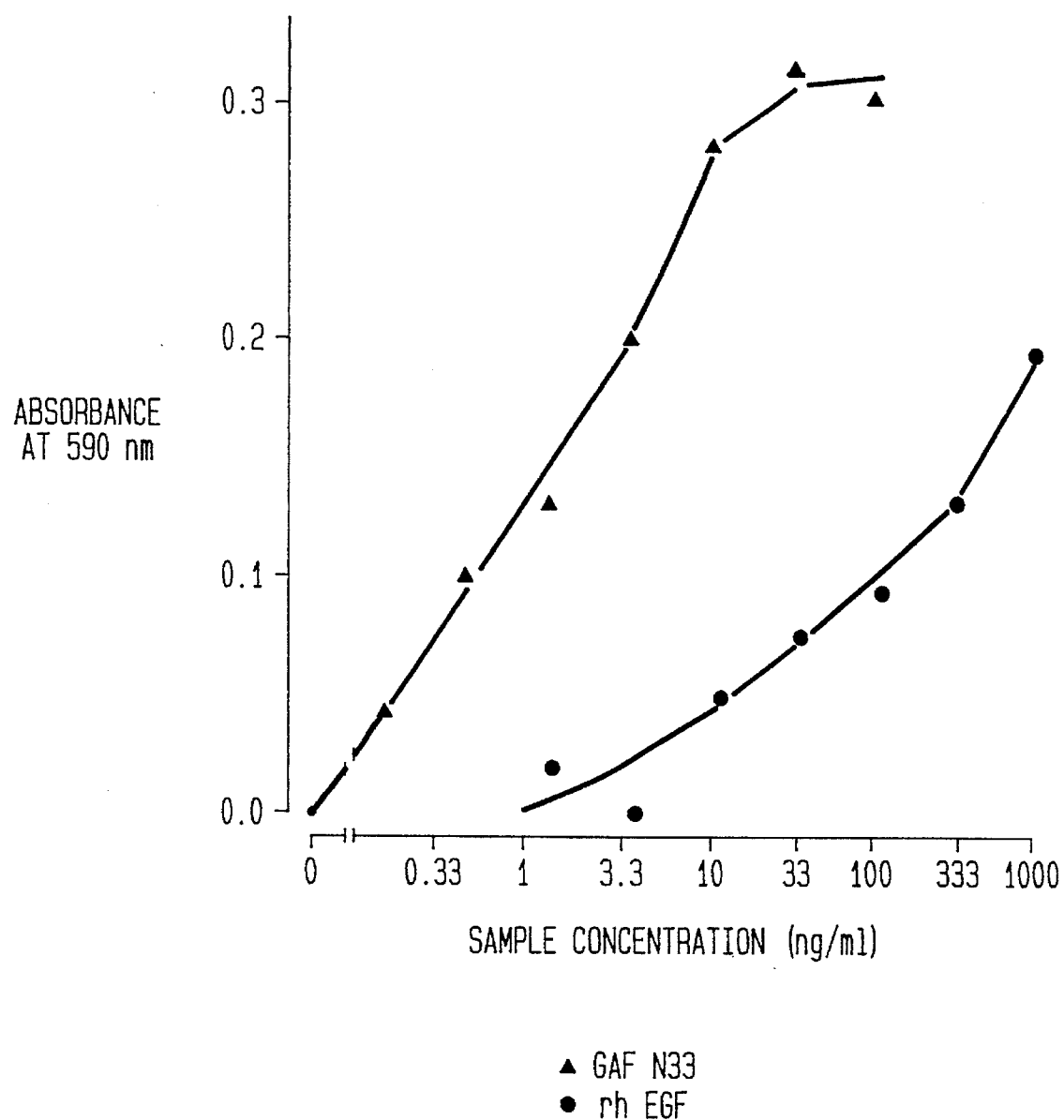

FIG. 21 is a graph showing growth promoting activity of GAF N33 (●) or rhEGF (▲) upon juvenile rat hepatic cells.

Figure 22:
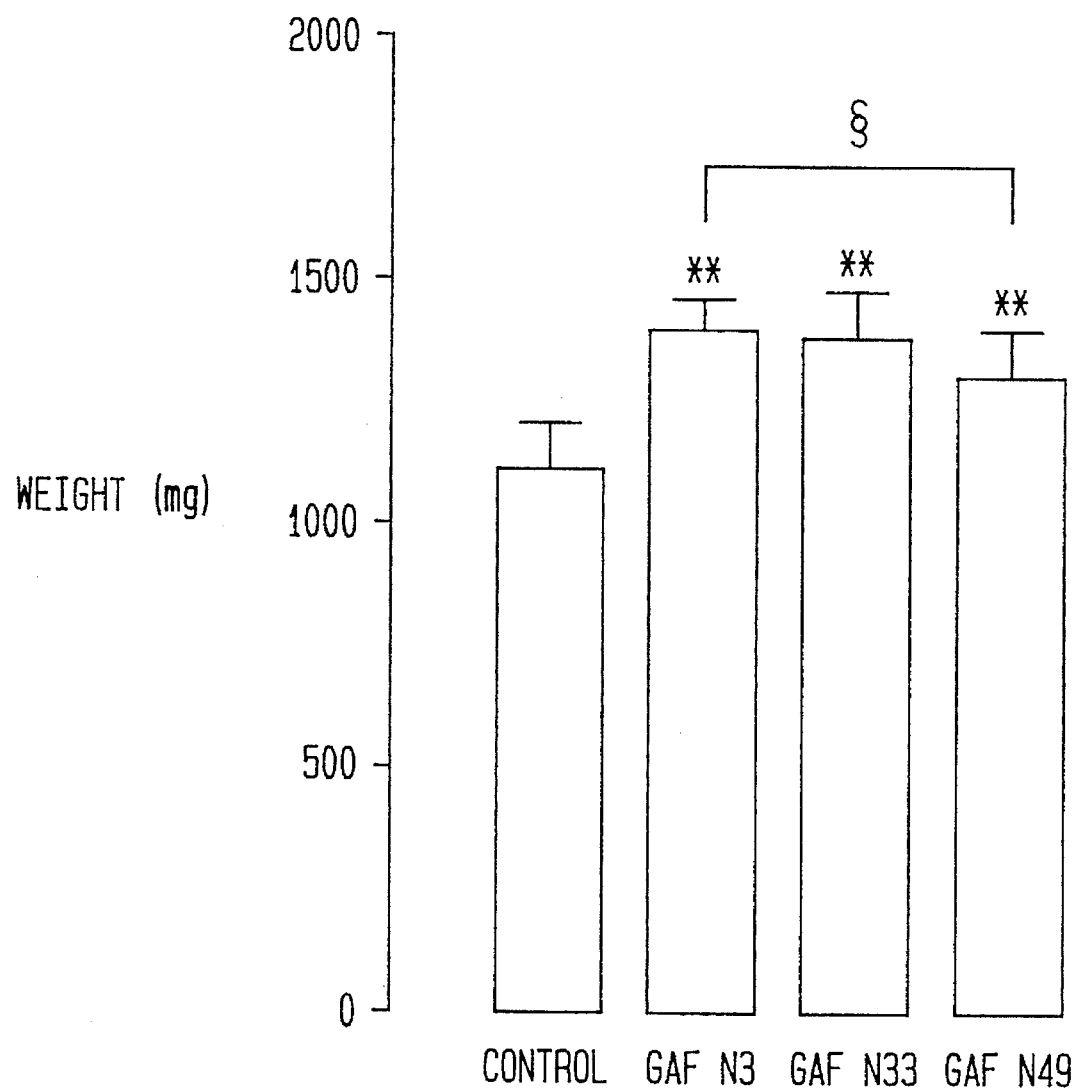

FIG. 22 is a graph showing liver weight-increasing action of GAF N3, N33 and N49.

Figure 23:
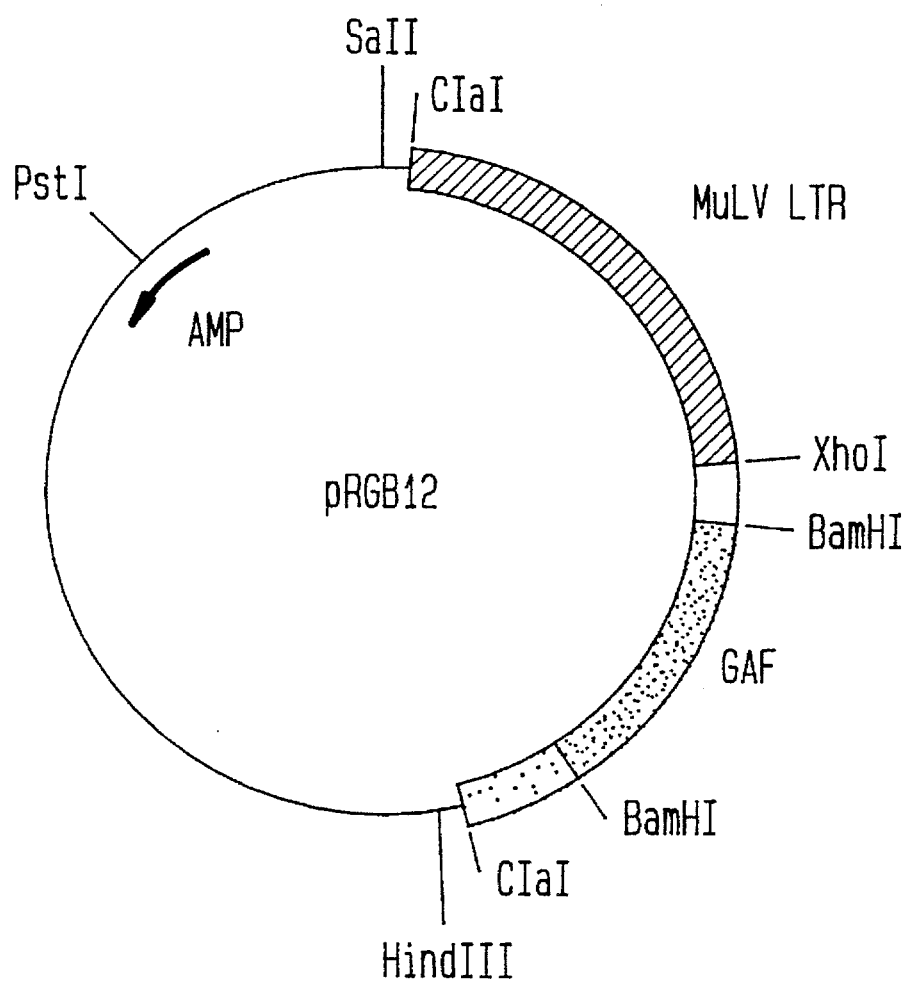

FIG. 23 is a representation showing a structure of GAF expression plasmid pRGB12 for animal cells.

Figure 24:
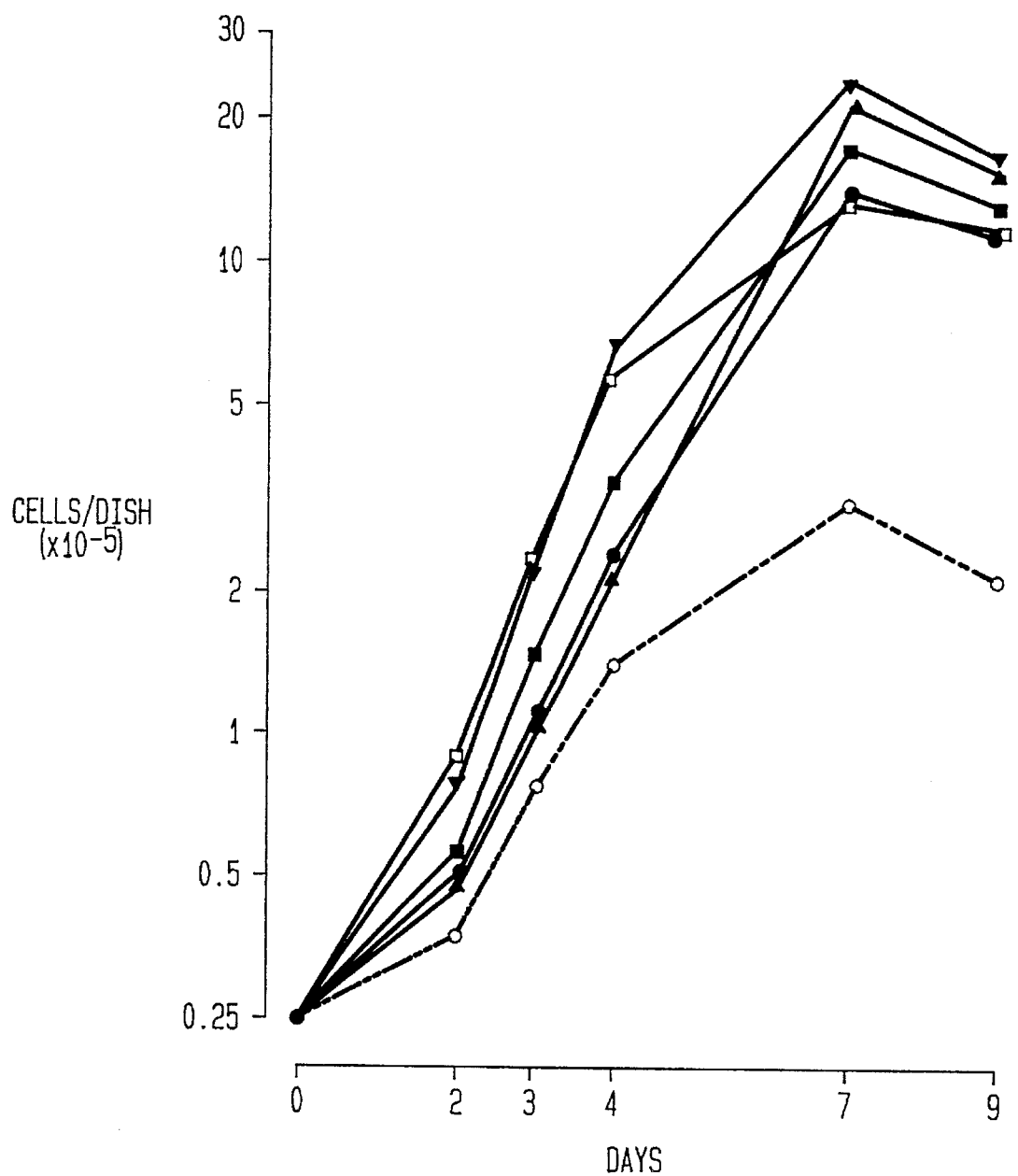

FIG. 24 is a graph showing growth curves of transformants ATG1 (●), ATG2 (▲), ATG3 (▼), ATG4 (■), ATG5 (□) and A31 (o) transformed with GAF cDNA.

Figure 25A:
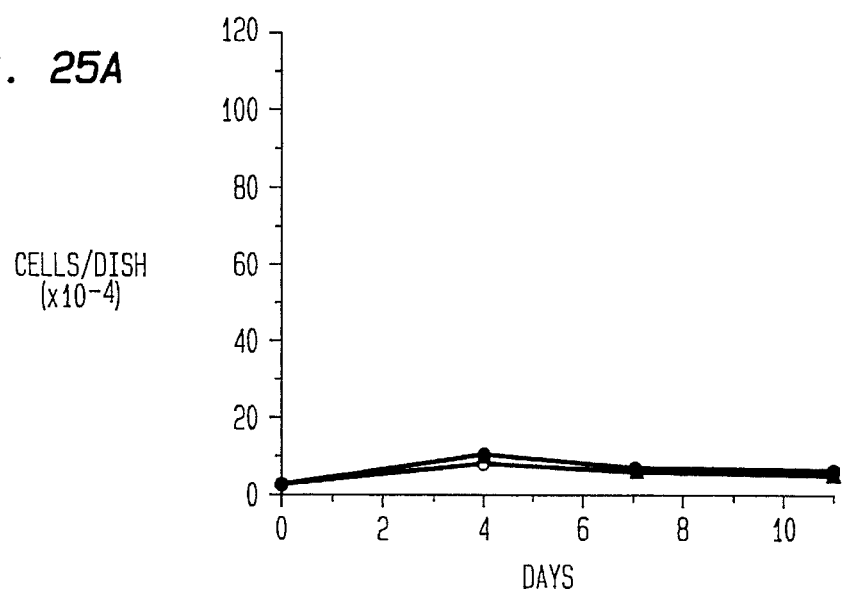
Figure 25B:
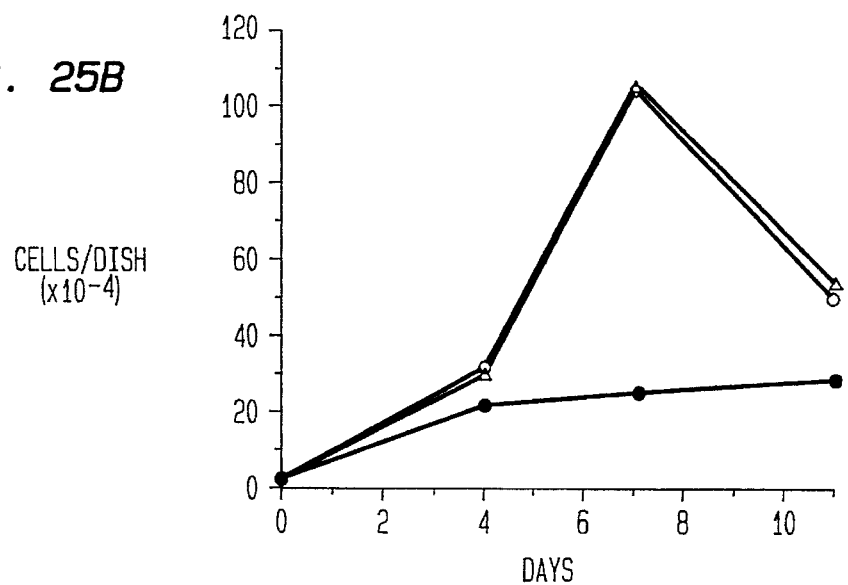
Figure 25C:
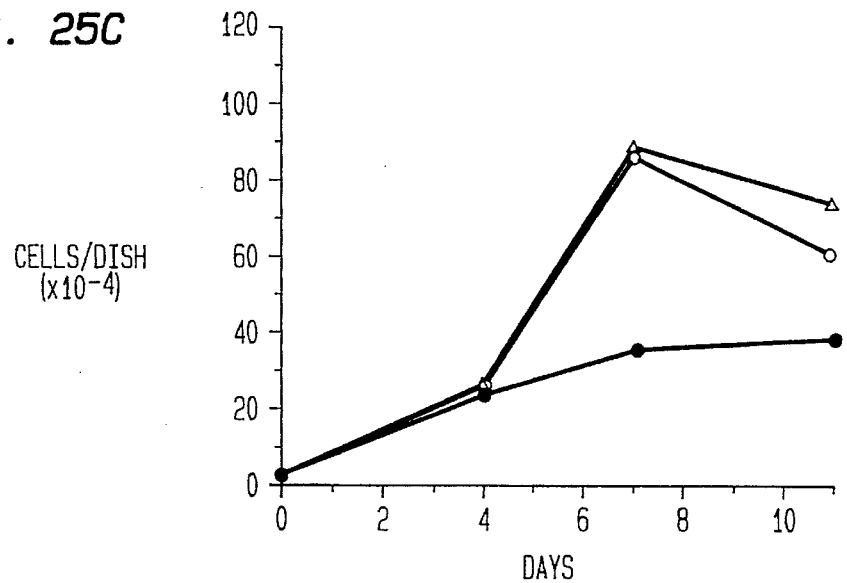

FIGS. 25(a), 25(b) and 25(c) are graphs showing action of an anti-GAF antibody on growth of parent strain A31(FIG. 25(a)), transformant ATG3(FIG. 25(b)) and ATG5(FIG. 25(c)), wherein 10 μg/ml of normal mouse IgG (Δ) or MoAb 150-59 (●) was added as the antibody. None was added as a control (o).

Figure 26:
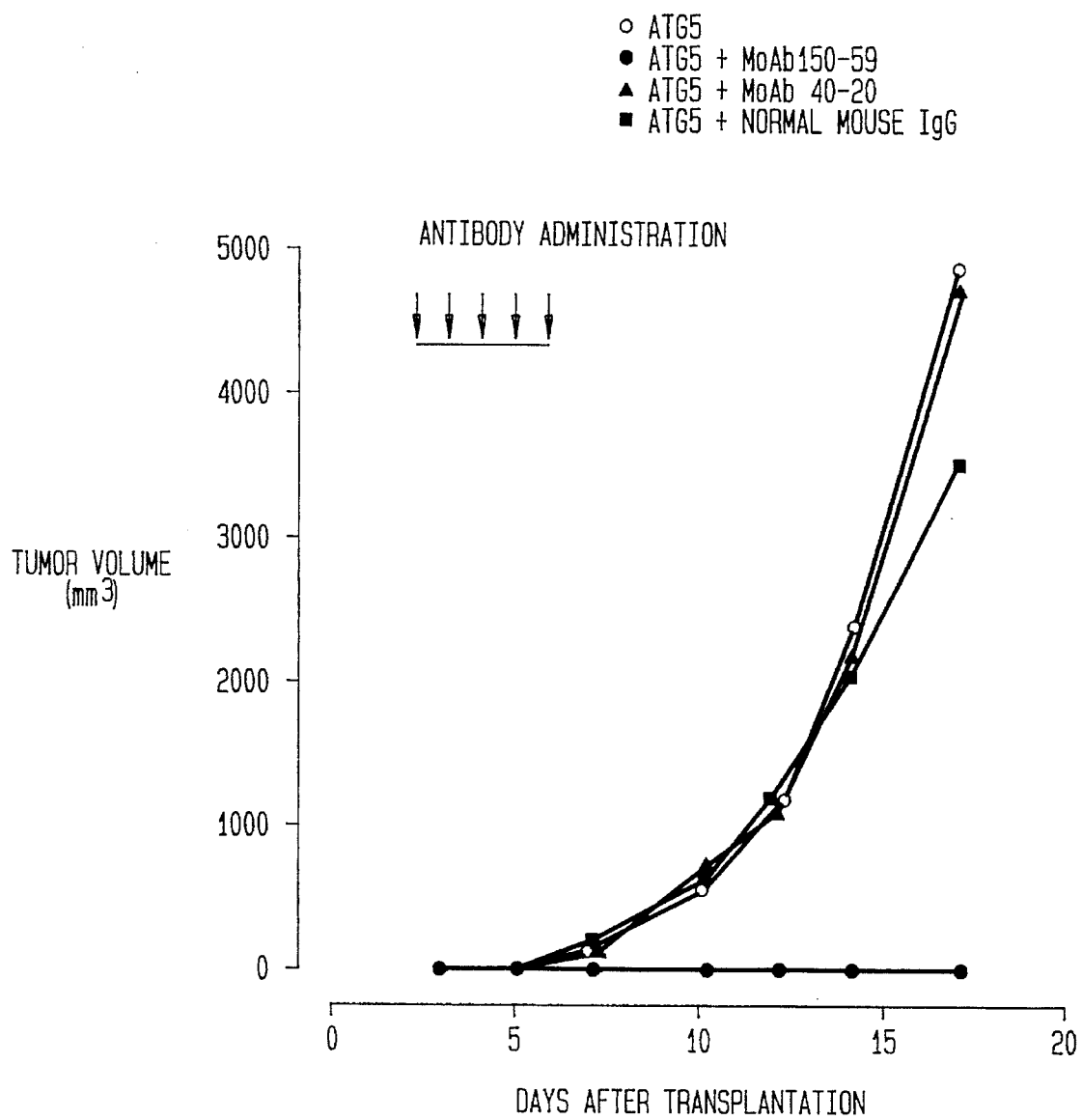

FIG. 26 is a graph showing tumor formation of transformant ATG5 in nude mice and inhibition effect with anti-GAF antibodies.

Figure 27:
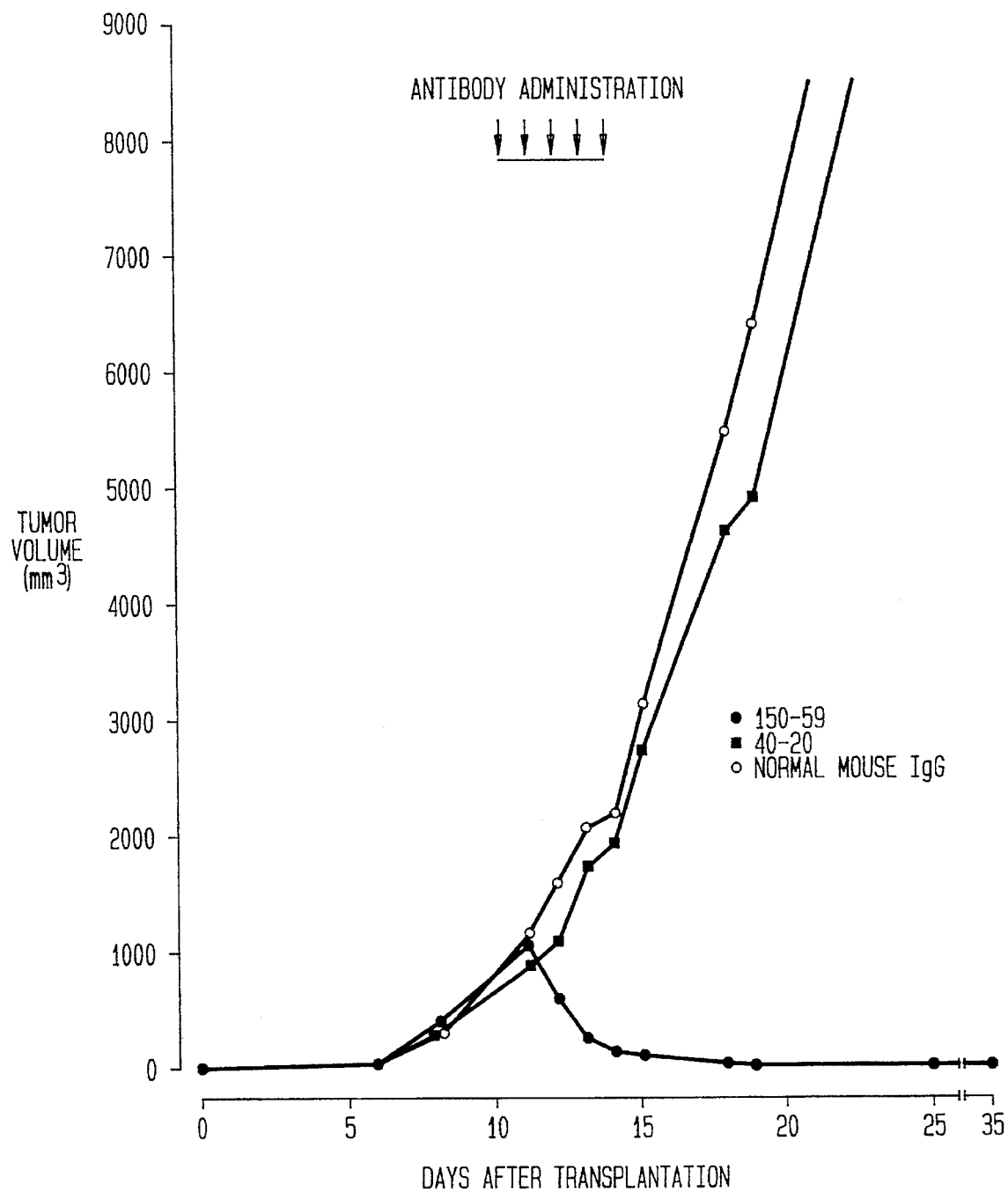

FIG. 27 is a graph showing a therapeutic experiment of tumors formed in nude mice by a transformant, with anti-GAF antibodies.

Figure 28:
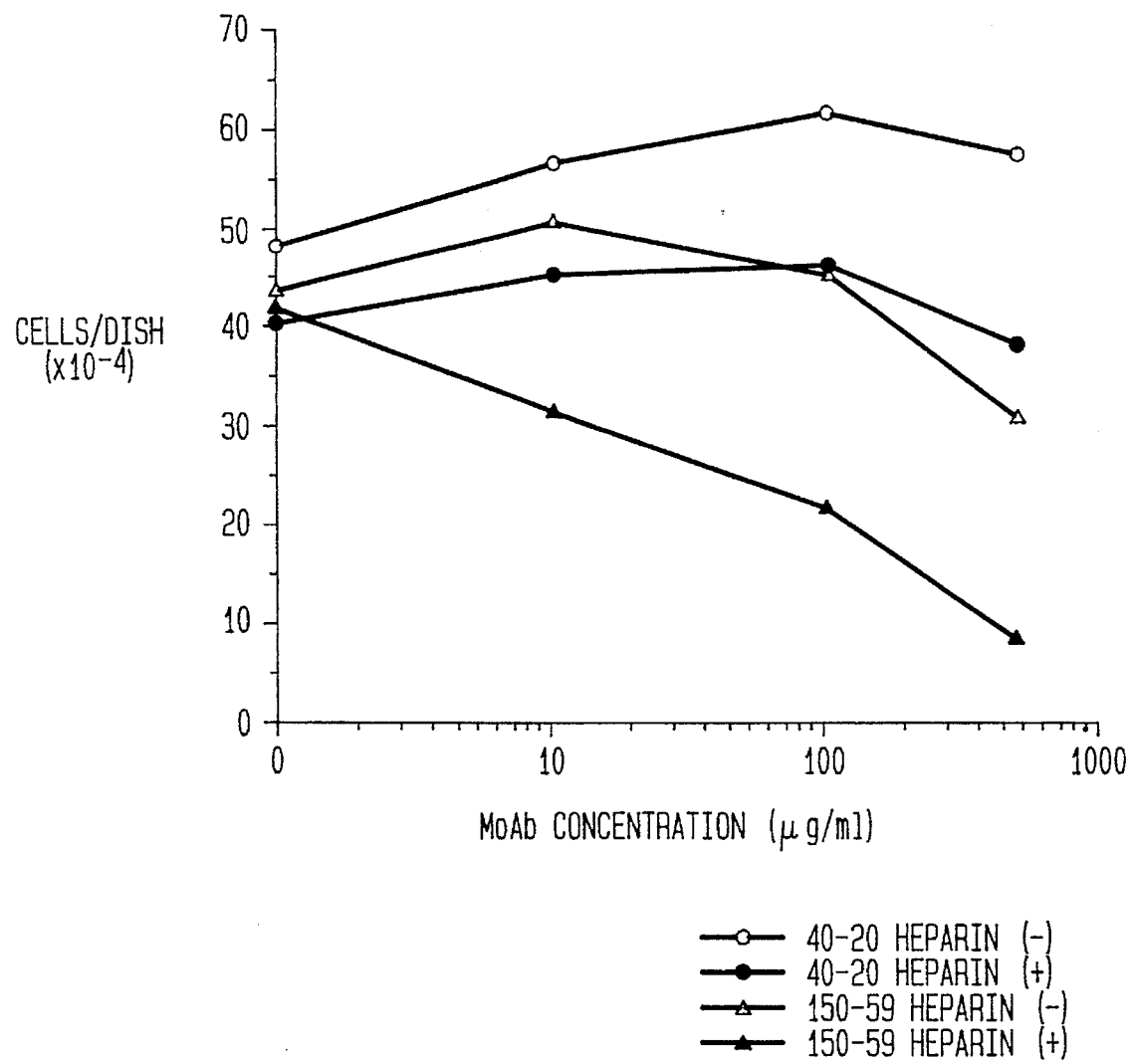

FIG. 28 is a graph showing the effect of inhibiting growth of stomach cancer cells AZ-521 with anti-GAF antibodies MoAb 150-59 and MoAb 40-20.

Figure 29:
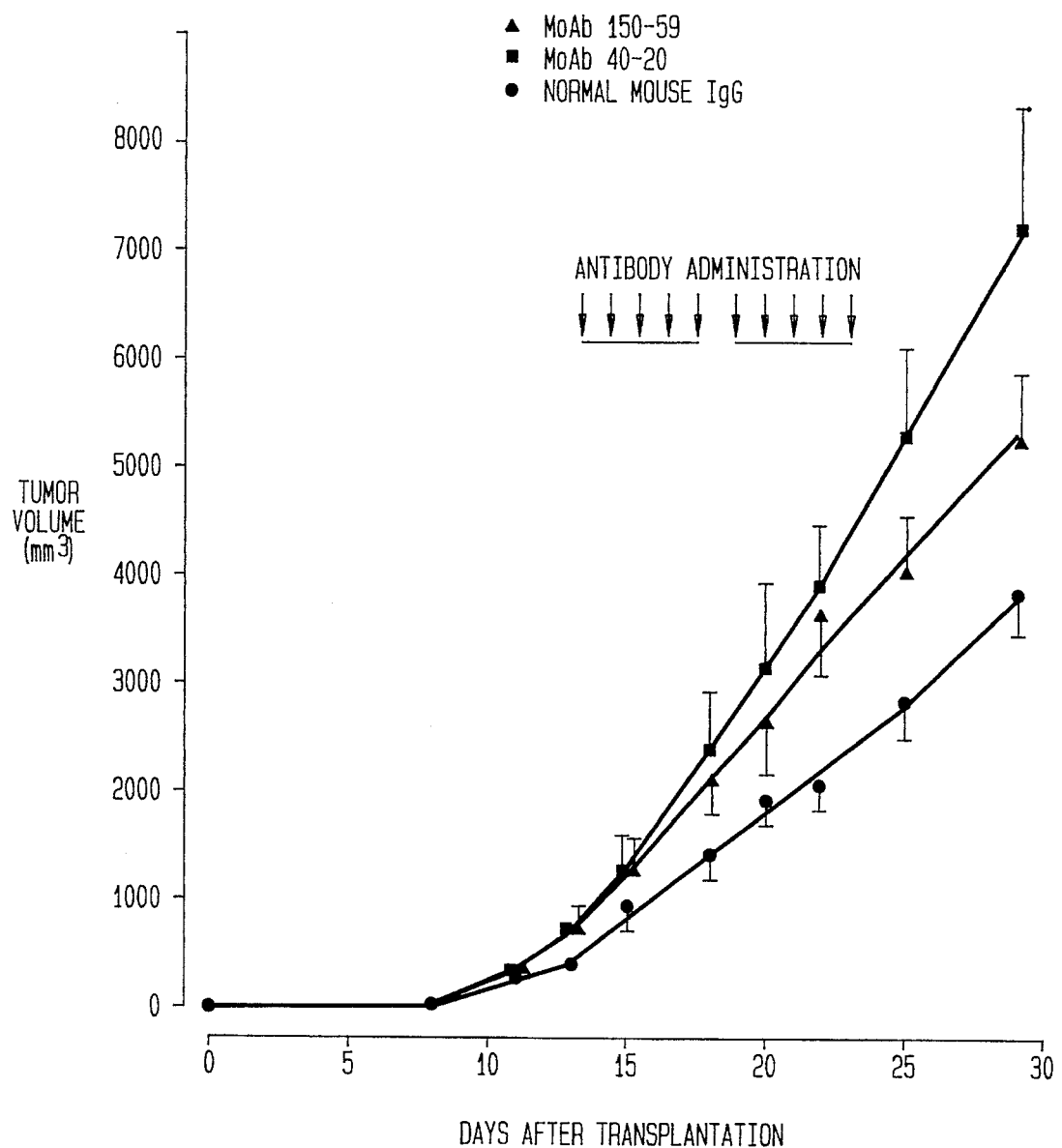

FIG. 29 is a graph showing the effect of anti-GAF antibodies on tumor formation of stomach cancer cells AZ-521 in nude mice.

DESCRIPTION OF THE PREFERRED EMBODIMENTS

In accordance with the present invention, there are provided (1) an antibody which specifically recognizes a glia activating factor polypeptide and is capable of neutralizing biological activity of said polypeptide; (2) the antibody of the above (1), wherein said antibody is a monoclonal antibody; (3) the antibody of the above (1) in which said biological activity is glia activating activity; (4) the antibody of the above (3), wherein said antibody is mouse monoclonal antibody GAF 150-59; (5) the antibody of the above (1), in which said biological activity is megakaryoblast growth promoting activity; (6) the antibody of the above (5), wherein said antibody is mouse monoclonal antibody GAF 4-82; (7) the antibody of the above (1), in which said polypeptide comprises a polypeptide represented by the following amino acid sequence:

Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp (SEQ ID NO:1); (8) the antibody of the above (1), in which said polypeptide comprises a polypeptide represented by the following amino acid sequence:

(Met)n X₁ Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser wherein n is 0 or 1; and X₁ represents Ala Pro Leu Gly Glu Val Gly Asn Tyr Phe Gly Val Gln Asp Ala Val Pro Phe Gly Asn Val Pro Val Leu Pro Val Asp Ser Pro Val Leu Leu Ser Asp His Leu Gly Gln Ser Glu Ala Gly Gly Leu Pro Arg Gly Pro Ala, or a fragment thereof (n=0: SEQ ID NO:2, n=1: SEQ ID NO:3); (9) the antibody of the above (8), wherein X₁ is Leu Gly Glu Val Gly Asn Tyr Phe Gly Val Gln Asp Ala Val Pro Phe Gly Asn Val Pro Val Leu Pro Val Asp Ser Pro Val Leu Leu Ser Asp His Leu Gly Gln Ser Glu Ala Gly Gly Leu Pro Arg Gly Pro Ala (n=0: SEQ ID NO:4, n=1: SEQ ID NO:5); (10) the antibody of the above (8), wherein X₁ is Ser Asp His Leu Gly Gln Ser Glu Ala Gly Gly Leu Pro Arg Gly Pro Ala (n=0: SEQ ID NO:6, n=1: SEQ ID NO:7); (11) the antibody of the above (8), wherein X₁ is Ala (n=0: SEQ ID NO:8, n=1: SEQ ID NO:9); (12) an antibody producing hybridoma wherein said antibody specifically recognizes a glia activating factor polypeptide and is capable of neutralizing biological activity of said polypeptide; (13) the hybridoma of the above (12), wherein said hybridoma is mouse hybrid hybridoma GAF 150-59 or GAF 4-82; (14) a method for producing a cloned hybridoma which comprises fusing a myeloma cell with a spleen cell from a mammal immunized with a glia activating factor polypeptide; (15) a method for producing the monoclonal antibody which specifically recognizes a glia activating factor polypeptide and is capable of neutralizing biological activity of said polypeptide, which comprises proliferating the cloned hybridoma produced by the method of the above (14) in a liquid culture medium or in an abdominal cavity of the mammal to form and accumulate the monoclonal antibody and then collecting the antibody; (16) an immunoassay for detecting or determining a biological activity of a glia activating factor polypeptide, which comprises using the antibody claimed in any one of the above (1) to (11) to determine the presence of a glia activating factor polypeptide in a specimen suspected of containing the same; (17) a method for purifying a glia activating factor polypeptide, which comprises using the antibody of any one of the above (1) to (11) to specifically bind with glia activating factor polypeptide to form conjugates and separating the conjugates; (18) a polypeptide represented by the following amino acid sequence:

(Met)n X₂ Val Thr Asp Leu Asp His Leu Lys Gly Ile Leu Arg Arg Arg Gln Leu Tyr Cys Arg Thr Gly Phe His Leu Glu

Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser wherein n is 0 or 1; and $X_2$ represents Ser Asp His Leu Gly Gln Ser Glu Ala Gly Gly Leu Pro Arg Gly Pro Ala or a fragment thereof (n=0: SEQ ID NO:6, n=1: SEQ ID NO:7); (19) a polypeptide of the above (18), wherein $X_2$ is Ser Asp His Leu Gly Gln Ser Glu Ala Gly Gly Leu Pro Arg Gly Pro Ala (n=0: SEQ ID NO:6, n=1: SEQ ID NO:7); (20) a polypeptide of the above (18), wherein $X_2$ is Ala (n=0: SEQ ID NO:8, n=1: SEQ ID NO:9); (21) a DNA encoding the polypeptide of the above (18) to (20); (22) a vector containing the DNA of the above (21); (23) a transformant carrying the vector of the above (22); (24) a pharmaceutical composition comprising a pharmacological suitable carrier containing a therapeutically effective amount of the polypeptide of any one of the above (18) to (20); (25) the pharmaceutical composition of the above (24), wherein said composition is a composition for promoting an increase in the number of platelets in a mammal; (26) a method for increasing platelets in mammal comprising administering to the mammal a platelet increasing effective amount of polypeptide as claimed in any one of claims 18 to 20; (27) the method of the above (26), wherein said polypeptide is administered with another agent; (28) the method of the above (27), wherein said another agent is an anticancer agent; (29) the method of the above (28), wherein said method comprises administering to the mammal polypeptide and an anticancer agent separately; (30) the method of the above (28), wherein said anticancer agent is selected from a group consisting of an alkylating agent, antimetabolite, antibiotics, plant alkaloides, platinum coordination compound and hormone; and (31) the method of the above (28), wherein said anticancer agent is selected from a group consisting of nitrogen mustard N-oxide, cyclophosphamide, melphalan, carboquone, busulfan, nimustine hydrochloride, ranimustine, dacarbazine, fluorouracil, tegaful, cytarabine, ancitabine hydrochloride, broxuridine, doxifluridine, mercaptopurine, thioinosine, methotrexate, mitomycin, bleomycin, daunorubicin hydrochloride, doxorubicin hydrochloride, pirarubicin hydrochloride, aclarubicin hydrochloride, neocarzinostatin, actinomycin D, vincristine sulfate, vindesine sulfate, vinblastine sulfate, etoposide, tamoxifen citrate, procarbazine hydrochloride, mitobronitol, mitoxanton hydrochloride, carboplatin and cisplatin.

In the present invention, the "glia activating factor (GAF) polypeptide" is a general term for polypeptides having glia activating factor activity (the GAF polypeptide is hereinafter also briefly referred to as "GAF"). The polypeptides include the polypeptide of SEQ ID NO:3 and fragments thereof.

Examples of the fragment peptides of GAF include deletion type muteins such as a mutein in which at least one amino acid residue is deleted from the N-terminus of SEQ ID NO:3 and/or from the C-terminus.

The GAF polypeptides, immunogens for preparing the antibodies of the present invention, include the polypeptide represented by SEQ ID NO:3 and the fragments thereof having GAF's biological activity. Usually, an antibody prepared by using a partial peptide as an immunogen can also recognize a whole molecular polypeptide containing the partial peptide portion. The partial peptide is therefore preferably used.

GAF of the present invention includes ones derived from mammals such as humans, monkeys, pigs, bovines, sheep and horses, which are selected according to applications of the antibodies. For example, GAF polypeptides derived from a certain mammal may be preferably selected for the purpose of treatment of the same mammal, and GAF polypeptides may be selected according to the animal species of GAF used for the purpose of tracing.

Examples of the GAF polypeptides further include ones extracted from various organs such as the brain and the kidney in which their existence has been already proved.

The GAF polypeptides may be produced by recombinant DNA techniques, and the fragments thereof may be synthesized by known synthesis methods such as chemical syntheses.

Examples of the GAF include a polypeptide containing the following amino acid sequence (SEQ ID NO:1), but are not limited thereto, as long as they have desired biological activity of GAF:

Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp

Preferred examples thereof include GAF comprising a polypeptide represented by the following amino acid sequence:

(Met)n $X_1$ Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser wherein n is 0 or 1; and $X_1$ represents Ala Pro Leu Gly Glu Val Gly Asn Tyr Phe Gly Val Gln Asp Ala Val Pro Phe Gly Asn Val Pro Val Leu Pro Val Asp Ser Pro Val Leu Leu Ser Asp His Leu Gly Gln Ser Glu Ala Gly Gly Leu Pro Arg Gly Pro Ala, or a fragment thereof (n=0: SEQ ID NO:2, n=1: SEQ ID NO:3).

In the amino acid sequence shown above, it is preferred that $X_1$ is Leu Gly Glu Val Gly Asn Tyr Phe Gly Val Gln Asp Ala Val Pro Phe Gly Asn Val Pro Val Leu Pro Val Asp Ser Pro Val Leu Leu Ser Asp His Leu Gly Gln Ser Glu Ala Gly Gly Leu Pro Arg Gly Pro Ala (n=0: SEQ ID NO:4, n=1: SEQ ID NO:5) or Ser Asp His Leu Gly Gln Ser Glu Ala Gly Gly Leu Pro Arg Gly Pro Ala (n=0: SEQ ID NO:6, n=1: SEQ ID NO:7) or Ala (n=0: SEQ ID NO:8, n=1: SEQ ID NO:9).

Examples of the fragments include polypeptides having desired activity, and preferably partial polypeptides of the GAF of SEQ ID NO:3 represented by the above-mentioned amino acid sequence.

Methods for producing such human GAF include the method described in European Patent Publication No. 503297.

The antibodies of the present invention may be obtained in accordance with known methods for preparing antibodies.

In general, mammals used for immunization include experimental animals such as bovines, goat, rabbits, guinea pigs, rats and mice.

When the rabbits are immunized, for example, any of the subcutaneous, intraperitoneal, intravenous, intramuscular and intracutaneous routes is available. For example, methods are frequently used in which immunization is carried out about 2 to about 6 times at intervals of two weeks and the blood is collected about 1 to about 15 days, preferably about 5 to about 10 days after the final immunization. The immunizing dose is preferably about 100 µg to about 10 mg per an animal such as rabbit, as the protein amount per one immunization.

Serum can be obtained by centrifugation of the collected blood.

The antibody titer in the serum can be assayed by the methods such as radio immunoassays (RIAs) or enzyme immunoassays (EIAs). For example, in the EIA, the serum is added to a solid phase (microtiter plate) by which the antigen (GAF) has been adsorbed. After washing sufficiently, a horseradish peroxidase (HRP)-labeled anti-immunoglobulin antibody (an anti-rabbit immunoglobulin antibody is used in the case of rabbit serum) or protein A is added thereto. After washing, color reaction is conducted, whereby the antibody binding to the antigen bound to the solid phase can be detected.

Neutralizing activity of the antibody of the present invention in the serum upon a GAF polypeptide is assayed more advantageously for an antibody fraction fractionated by ion exchange column chromatography, protein A column chromatography, protein G column chromatography or the like than for the serum. Of these, protein A column chromatography and protein G column chromatography are particularly preferred because of their simplicity and easiness.

The neutralizing activity of the antibody of the present invention can be assayed by use of methods for assaying GAF's activity. For example, based upon the uptake of tritium thymidine ($^3$H. thymidine) in glial cells or in 3T3 cells, it can be assayed by adding the antibody to the reaction system together with GAF and assaying the inhibition of GAF's $^3$H. thymidine uptake promoting activity. It can also be assayed by the inhibition of the increase of cell number caused by GAF.

Further, for a neutralizing antibody to the activity of growth promotion of megakaryoblasts (MK-CSF activity) of GAF and increasing the number of the platelets in the blood, assay of inhibition of these activities makes it possible to determine the neutralizing activity.

Preferred examples of mammals used to prepare monoclonal antibodies of the present invention include rats and mice. When the mice are immunized, for example, any of the subcutaneous, intraperitoneal, intravenous, intramuscular and intracutaneous routes is available. Mainly, subcutaneous, intraperitoneal and intravenous injections are preferred, and the subcutaneous injection is particularly preferred. The immunizing interval and the immunizing dose are widely changeable, and various methods are available. For example, methods are frequently used in which immunization is carried out about 2 to about 6 times at intervals of about 2 weeks and spleen cells removed about 1 to about 5 days, preferably about 2 to about 4 days after the final immunization are used. The immunizing dose is preferably about 0.1 µg or more preferably about 10 to about 300 µg per mouse, as the peptide amount per one immunization. Further, it is preferred to carry out a cell fusion using the spleen cells after confirmation of an increase in antibody titer in the blood by partially collecting the blood before removal of the spleens.

The thus-prepared spleen cells are fused with lymphoid cells. For example, the spleen cells removed from the mice are fused with lymphoid cells such as the same or a different kind (preferably the same kind) of myeloma cells, for example, P3-X63-Ag. SUI [Ichimori et al., *J. Immun. Method*, 80, 55 (1985)], having characteristics useful as selection marker such as hypoxanthine-guanine-phosphoribosyl transferase deficient (HGPRT$^-$) or thymidine kinase deficient (TK$^-$). The fused cells can be produced by fusion in accordance with the method of Köhler and Milstein [*Nature*, 556, 495 (1975)]. Namely, for example, the myeloma cells and the spleen cells are suspended in a ratio of about 1:5 in a 1:1 mixed medium of Iscove medium and Ham F-12 medium (hereinafter, IH medium), and a fusogen such as Sendai virus or polyethylene glycol (PEG) is added thereto. It is of course possible to add another fusogen such as dimethyl sulfoxide (DMSO). The molecular weight of PEG is usually about 1,000 to about 9,000, the fusion time is about 0.5 to about 30 minutes, and the concentration is about 10 to about 80%. As a preferred example, fusion is conducted in a concentration of about 35 to about 55% for about 4 to about 10 minutes using PEG 6,000, which results in efficient fusion. The fused cells can be selectively proliferated using hypoxanthine-aminopterin-thymidine medium (HAT medium) [*Nature*, 256, 495 (1975)].

The culture supernatant of the proliferated cells can be screened for whether a desired antibody has been produced or not. The screening of the antibody titer can be carried out in the following manner. In this case, first, the presence or absence of the antibody produced by peptide immunization can be examined by radio immunoassays (RIAs) or enzyme immunoassays (EIAs). For these methods, various modified methods are also available.

As a preferred example of the assays, a method using the EIA is hereinafter described. A rabbit anti-mouse immunoglobulin antibody is coupled with a carrier such as cellulose beads according to conventional methods, and then a culture supernatant or mouse serum to be assayed is added thereto, followed by reaction at a room temperature (about 4° to about 40° C. hereinafter the same) for a defined time After the reaction product is thoroughly washed, an enzyme labeled antigenic protein in which the enzyme is chemically conjugated with antibody is added thereto and the reaction is carried out at a room temperature for a defined time. Then, an enzyme substrate is added thereto, followed by reaction at a room temperature for a defined time. Then, the absorbance or fluorescence of the product can be measured.

The antibody titer in rabbit serum can be assayed in a similar manner.

For the resulting culture supernatant of anti-GAF antibody producing cells, the neutralizing activity of the antibody upon the biological activity of the GAF polypeptide can be screened in the following manner. Namely, in the case of the neutralizing antibody to glia activating activity, the neutralizing activity can be assayed by measuring changes with time in the number of cells, growth of which is induced by the GAF polypeptide. Although glial cells, fibroblasts or the like can be used as such cells, glial cells are preferably used. Inhibition of the growth promoting activity by the GAF polypeptide is desirably assayed by measuring changes in the number of glial cells with time. For the neutralizing antibody to the growth promoting activity of megakaryoblasts, the number of megakaryoblasts or speciallized megakaryoblasts is measured in the presence of the GAF to assay inhibition of GAF's activity.

Methods for measuring the number of cells include the method of directly counting the number of cells, the method of determining radioactivity using tritium thymidine, and the method of colorimetrically measuring the number of cells by use of (4,5-dimethyl-2-thiazolyl)-2,5-diphenyl-2H-tetrazolium bromide (MTT) (MTT method).

The cells in wells which show cell proliferation in a selective medium and antibody activity upon the peptide used for immunization and the desired neutralizing activity, can be cloned by a limiting dilution method. The supernatant of the cloned cells is screened to determine whether it shows a high antibody titer or not, thereby obtaining monoclonal antibody-producing hybridoma clones showing reactivity with the immunized peptide.

The hybridoma cells thus cloned are proliferated in a liquid medium. Specifically, for example, the hybridoma cells are cultivated in a known liquid medium such as a medium comprising RPMI-1640 [G. E. Moore et al., *J. Am. Med. Assoc.*, 199, 549 (1967)] and about 0.1–40% bovine serum for about 2 to about 10 days, preferably for about 3 to about 5 days, whereby the monoclonal antibody can be obtained from the culture solution. The antibody can also be obtained by intraperitoneally inoculating mammals with the hybridoma cells to proliferate the cells, and then collecting the ascites. For example, in the case of mice, about $1 \times 10^4$ to about $1 \times 10^7$, preferably about $5 \times 10^5$ to about $2 \times 10^6$ hybridoma cells are intraperitoneally inoculated into mice such as BALB/c preliminarily inoculated with mineral oil, etc., and the ascites is collected after about 7 to about 20 days, preferably after about 10 to about 14 days. The monoclonal antibody produced and accumulated in the ascites can be easily isolated as pure immunoglobulin by known separation and purification methods such as ammonium sulfate fractionation, DEAE-cellulose column chromatography and protein A or protein G column chromatography.

The antibodies of the present invention highly sensitively and selectively bind to the GAF polypeptides. Accordingly, they are very useful as reagents for detecting or determining GAF, and further for purifying GAF polypeptides.

Detection and determination of GAF polypeptides using the antibodies of the present invention can be performed, for example, by the immunochemical assay of measuring the GAF polypeptide using an anti-GAF antibody held on a carrier and a conjugate in which a labeling agent is directly bound to an anti-GAF antibody different from the above-mentioned antibody in the antigen recognition site.

The determination steps may include contacting a sample containing antigen with the antibody to form a conjugate or complex, contacting the conjugate with a second antibody bearing a detectable label such as radio isotope, enzyme or fluorescence, and detecting complexes of the antigen and two antibodies by detecting the label. In measurement, either of the antibodies may be a neutralizing antibody, and both may be neutralizing antibodies as long as they do not overlap each other in their antigen recognition site. Further, corresponding to biological activities for detection and determination, a neutralizing antibody to each activity is preferably selected.

Purification of GAF polypeptides using the antibodies of the present invention can be performed, for example, through steps like contacting GAF with specific antibody to form conjugates separating the conjugates and reconstituting the GAF to active form. For the separation of the GAF-antibody conjugate, the anti-GAF antibody held on a carrier is convenient to use. It could be used for antibody column.

Examples of the carriers to which the antibodies are bound in the above-mentioned assays include gel particles for example, agarose gels such as Sepharose 4B and Sepharose 6B (Pharmacia Fine Chemical, Sweden), dextran gels such as Sephadex G-75, Sephadex G-100 and Sephadex G-200 (Pharmacia Fine Chemical, Sweden) and polyacrylamide gels such as Biogel P-30, Biogel P-60 and Biogel P-100 (Bio RAD Laboratories, U.S.A.); cellulose particles, for example, Avicel (Asahi Chemical Industry, Japan) and ion exchange cellulose such as diethylaminoethyl cellulose and carboxymethyl cellulose; physical adsorbents, for example, glass such as glass balls, glass rods and aminoalkyl glass rods, silicone pieces, styrene resins such as polystyrene balls and polystyrene particles, and plates for immunoassay (for example, Nunc, Denmark); and ion exchange resins, for example, acescent cation exchange resins such as Amberlite IRC-50 (Rohm & Haas, U.S.A.) and Zeocurve 226 (Permutit, West Germany), and alkalescent anion exchange resins such as Amberlite IR-4B and Dowex (Dow Chemical, U.S.A.).

In order to bind the antibody on the carrier, conventional methods can be used. Examples of such methods include the cyanogen bromide method and the glutaraldehyde method which are described in *Metabolism*, 8, 696 (1971). As a simpler method, the antibody may be adsorbed on the surface of the carrier.

Examples of the labeling agents in the labeling agent-bound antibody conjugates include radioisotopes, enzymes, fluorescent substances and luminous substances, and enzymes are preferably used. Enzymes which are stable and high in specific activity are preferred, and peroxidases, alkaline phosphatases, β-D-galactosidases, glucose oxidases and the like can be used. Peroxidases are preferred among others, and peroxidases of various origins can be used. Examples thereof include peroxidases derived from horseradishes, pineapples, figs, sweet potatoes, broad beans and corn. Horseradish peroxidase (HRP) extracted from horseradishes is preferred among others.

In binding the peroxidase to the antibody, the peroxidase into which a maleimide group is preliminarily introduced is conveniently used to utilize the thiol group of Fab' as an antibody molecule.

When the maleimide group is introduced into the peroxidase, the maleimide group can be introduced through an amino group of the peroxidase. For this purpose, N-succinimidyl-maleimide-carboxylate derivatives can be used, and N-(γ-maleimidobutyloxy)succinimide (hereinafter, also "GMBS") is preferably used. A certain group may therefore intervene between the maleimide group and the peroxidase.

GMBS is reacted with the peroxidase in a buffer solution having a pH of about 6 to about 8 at about 10° to about 50° C. for about 10 minutes to about 24 hours. The buffer solutions include, for example, 0.1M phosphate buffer (pH 7.0). The maleimidated peroxidase thus prepared can be purified, for example, by gel chromatography. Examples of carriers used in the gel chromatography include Sephadex G-25 (Pharmacia Fine Chemical, Sweden) and Biogel P-2 (Bio RAD Laboratories, U.S.A.).

The maleimidated peroxidase can be reacted with the antibody molecule in a buffer solution at about 0° to about 40° C. for about 1 to about 40 hours. Examples of the buffer solutions include 0.1M phosphate buffer (pH 6.0) containing 5 mM sodium ethylenediaminetetraacetate (EDTA). The peroxidase-labeled antibody thus prepared can be purified, for example, by gel chromatography. Examples of carriers used in the gel chromatography include Sephadex G-25 (Pharmacia Fine Chemical, Sweden) and Biogel P-2 (Bio RAD Laboratories, U.S.A.).

Further, a thiol group may be introduced into the peroxidase to react with the maleimidated antibody molecule.

Enzymes other than the peroxidases can also be directly bound to antibodies in accordance with the methods used for binding the peroxidases. Known methods which achieve such binding include, for example, the glutaraldehyde method, the periodic acid method and the water-soluble carbodiimide method.

Samples to be tested in an assay system used in the present invention include fluids such as urine, serum, plasma and cerebrospinal fluid, extract of animal cells, and culture supernatants thereof.

As an example of assays used in the present invention, a case is hereinafter described in detail in which a peroxidase is used as the labeling agent, but the present invention is not limited thereto.

(1) First, a test sample containing a GAF polypeptide to be assayed is added to an antibody held on a carrier to conduct antigen-antibody reaction, and then a conjugate of a peroxidase with another antibody to the GAF polypeptide obtained in a manner similar to that described above is added thereto to allow them to react with each other.

(2) A substrate of the peroxidase is added to the reaction product obtained in (1), and then the absorbance or the fluorescent intensity of the resulting substance is measured, thereby detecting enzyme activity of the above-mentioned reaction product.

(3) A standard solution containing a known amount of the GAF polypeptide are previously subjected to the procedures of the above (1) and (2) to prepare a standard curve showing the relation between the amount of the GAF polypeptide and the absorbance or the fluorescent intensity thereof.

(4) The absorbance or the fluorescent intensity obtained for the test sample (sample to be tested) containing an unknown amount of the GAF polypeptide is applied to the standard curve to determine the amount of the GAF polypeptide contained in the test sample.

Active GAF can be efficiently assayed with the antibodies of the present invention because of their activity of neutralizing GAF's biological activity.

When the GAF polypeptide is purified, the purified antibody of the present invention is coupled with an appropriate carrier such as activated agarose gel beads according to conventional methods, followed by packing in a column. Then, a sample containing the crude GAF polypeptide, such as a culture supernatant or a fluid of disrupted cells, is loaded onto the antibody column to allow the sample to be adsorbed thereby, and then washed. Thereafter, the column is eluted with a chaotropic reagent such as potassium thiocyanate (KSCN) or under such slightly acidic conditions that GAF is not inactivated. Thus, the GAF polypeptide can be efficiently purified.

The antibody column can be prepared by coupling the monoclonal antibody of the present invention with an appropriate carrier, which antibody is, for example, purified from ascites or other fluids inoculated with hybridoma cells.

Any carrier may be used as long as the GAF polypeptide is specifically efficiently adsorbed thereby after coupling and suitable elution is thereafter possible. Examples of the carriers include agarose, cellulose and acrylamide polymers. As an example, agarose gel beads in which a primary amine of a protein is activated so as to be easily bindable, such as Affi-Gel 10 (Bio RAD), are conveniently used according to the following method. The antibody is reacted with Affi-Gel 10 in a buffer solution such as a bicarbonate solution having a concentration of about 0.001 to about 1M, preferably about 0.1M. The reaction can be conducted at about 0° to about 20° C. at various pH values for about 10 to about 24 hours, and preferably at about 4° C. at a pH of about 7 to about 10 for about 4 hours. With respect to the mixing ratio of the antibody to Affi-Gel 10, the amount of the antibody which becomes bound to Affi-Gel 10 increases as the amount of the antibody mixed therewith increases, until the ratio reaches about 50 mg of antibody per 1 ml of Affi-Gel 10. Hence, any ratio can be employed within this range. However, about 10 to about 30 mg of the antibody is conveniently used, considering the binding efficiency and the purification efficiency in affinity column chromatography. The antibody-carrier combined material thus formed is thoroughly washed with the buffer solution used in the reaction. Then, residual unreacted active groups are blocked by allowing the washed material to stand for several days, or by adding a compound containing a primary amine such as ethanolamine-hydrochloric acid or glycine thereto to a final concentration of about 0.05 to about 0.10M, followed by reaction at about 4° C. for about 1 to about 4 hours, or by reacting a protein such as above about 1 to about 5% bovine serum albumin (BSA) therewith at 4° C. overnight. The material thus treated is packed in an appropriate column to form the antibody column.

In purification with the above-mentioned antibody column, for example, a GAF polypeptide-containing sample is dissolved in a buffer solution having a pH around neutrality such as phosphate buffer or Tris-hydrochloric acid buffer, and adsorbed by the antibody column. Then, the column is washed with the same buffer, followed by elution of the GAF polypeptide. Eluents which can be used include slightly acidic solutions such as acetic acid solutions, solutions containing polyethylene glycol, solutions containing peptides more easily bindable with the antibody than the sample, high concentration salt solutions and combined solutions thereof. Solutions which do not so accelerate decomposition of the GAF polypeptide are preferred.

Column effluents are neutralized with buffer solutions by conventional methods. The above-mentioned purification procedure can be repeated if necessary.

Thus, the substantially pure GAF polypeptide substantially free from pyrogens and endotoxins is obtained. The substantially pure GAF polypeptide of the present invention contains the GAF polypeptide at a concentration of about 90% (w/w) or more, preferably about 95% (w/w) or more.

Continuous stimulation for growth of a cell can result in little or no effect on cell growth or can possibly make the cell malignant. If a cell having a receptor for a certain growth factor on the surface thereof has self-producing capability for the growth factor, overproduction of the growth factor by the cell can result in a cancer. This effect is known as "autocrine" transformation. GAF is a growth factor supporting growth of many mesoderm-derived cells such as fibroblasts, glial cells, osteoblast and nerve cells. If these cells acquire the property of overproducing GAF, the cells are considered cancerous.

For example, cells producing GAF such as NMC-GI cells appear in human spontaneous cancer. This factor is therefore considered as one of the potential oncogene. For such cases, antibodies neutralizing the biological activity of GAF can improve symptoms thereof. Namely, the antibodies of the present invention which is capable of neutralizing cell growth activity of GAF can be used as anticancer agents. When the antibodies are used as the anticancer agents, they are given, for example, as injections intravenously, subcutaneously, intraperitoneally or to tumor focuses. In the case of brain tumor, they may be directly given intracranially. In these cases, the antibodies are given, for example, in doses of about 1 μg to about 10 mg/kg, and can also be used in combination with other pharmaceutically acceptable carriers such as stabilizing agents, immunostimulants or chemotherapeutants.

In N-terminus-deleted fragments of the polypeptide of SEQ ID NO:3 namely the polypeptides having the following amino acid sequence: (Met)n $X_2$ Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser (wherein $X_2$ represents Ser Asp His Leu Gly Gln Ser Glu Ala Gly Gly Leu Pro Arg Gly Pro Ala, or a fragment thereof; and n is 0 or 1 (n=0: SEQ ID NO:6, n=1: SEQ ID NO:7), the fragment of $X_2$ may have at least one amino acid residue of the sequence of Ser Asp His Leu Gly Gln Ser Glu Ala Gly Gly Leu Pro Arg Gly Pro Ala. Usually, this fragment preferably contains the C-terminal Ala of the above sequence. Included is the use of a fragment consisting of the C-terminal Ala alone.

These fragments are stable against heat and acidic condition.

In accordance with the present invention, the GAF polypeptide can be prepared, for example, by the following process:

(a) mRNA coding for human GAF is extracted from cells, (b) Single stranded complementary DNA (cDNA) is synthesized from the mRNA, followed by synthesis of double stranded complementary DNA, (c) The complementary DNA is introduced into a phage vector or a plasmid, (d) The recombinant phage or plasmid thus obtained is introduced into an appropriate host cell to produce a transformant, (e) After cultivation of the transformant thus obtained, the plasmid or the phage containing the desired DNA is isolated from the transformant by an appropriate method such as hybridization using the DNA probe, (f) The desired cloned DNA is cut out from the recombinant DNA, and (g) The cloned DNA or a portion thereof is ligated downstream from a promoter in a vector suitable for expression.

The mRNA coding for the human GAF can be obtained from various GAF-producing cells such as human glioma cells and human fibroblasts. The human glioma cells include NMC-G1, and the human fibroblasts include WI-38 (ATCC No.: CCL-75).

The above-mentioned cell NMC-G1 was deposited with the Institute for Fermentation, Osaka, Japan (IFO), under the accession number IFO 50281 on October 31, 1990, and with the National Institute of Bioscience and Human-technology (NIBH) (formerly the Fermentation Research Institute), Agency of Industrial Science and Technology, the Ministry of International Trade and Industry, Japan, under the accession number FERM BP-3294 on February 21, 1991. WI-38 is cited in *Catalogue of Cell Lines & Hybridomas*, 5th edition, published by the American Type Culture Collection (1985).

Methods for preparing the RNA from the GAF-producing cells include the guanidine thiocyanate method [J. M. Chirgwin et al., *Biochemistry*, 18, 5294 (1979)] and the like.

Using the mRNA thus obtained as a template, cDNA is synthesized and then introduced into the plasmid or the phage by use of reverse transcriptase, for example, in accordance with the method of H. Okayama et al. [*Molecular and Cellular Biology*, 2, 161 (1982) and ibid,, 3, 280 (1983)].

The plasmids into which the cDNA is introduced include, for example, pBR322 [*Gene*, 2, 95 (1977)], pBR325 [*Gene*, 4, 121 (1978)], pUC12 [*Gene*, 19, 259 (1982)], pUC13 [*Gene*, 19, 259 (1982)], pUC118 and pUC119, each derived from *E. coli*, and pUB110 derived from *Bacillus subtilis* [*Biochemical and Biophysical Research Communication*, 112, 678 (1983)]. However, any other plasmid can be used as long as it is replicable and viable in the host.

Methods for introducing the cDNA into the plasmid include, for example, the method described in T. Maniatis et al., *Molecular Cloning*, p.239, Cold Spring Harbor Laboratory, (1982). Methods for introducing the cDNA into the phage vector include, for example, the method of T. V. Hyunh et al. [*DNA Cloning, A Practical Approach*, 1, 49 (1985)].

The above-mentioned plasmids may be prepared by introducing the cDNA synthesized from human normal diploid cell mRNA into a vector such as pCD vector [see Okayama et al., *Molecular Cell Biology*, 3, 280 (1983)].

The plasmid is introduced into appropriate host cells such as cells belonging to *Escherichia* and *Bacillus*.

Examples of the cells belonging to *Escherichia* described above include *E. coli* K12DH1 [*Proc. Natl. Acad. Sci. U.S.A.*, 60, 160 (1968)], M103 [*Nucleic Acids Research*, 9, 309 (1981)], JA221 [*Journal of Molecular Biology*, 120, 517, (1978)], HB101 [*Journal of Molecular Biology*, 41, 459 (1969)] and C600 [*Genetics*, 39, 440 (1954)].

Examples of the cells belonging to *Bacillus* described above include *Bacillus subtilis* MI114 [*Gene*, 24, 255 (1983)] and 207-21 [*Journal of Biochemistry*, 95, 87 (1984)].

Methods for transforming the host with the plasmid include, for example, the calcium chloride method and the calcium chloride/rubidium chloride method described in T. Maniatis et al., *Molecular Cloning*, p.249, Cold Spring Harbor Laboratory, (1982).

Desired clones are selected from the transformants thus obtained by using known methods such as the colony hybridization method [*Gene*, 10, 63 (1980)], and the DNA nucleotide sequence determination methods [*Proc. Natl. Acad. Sci. U.S.A.*, 74, 560 (1977); *Nucleic Acids. Research*, 9, 309 (1981)].

Thus, a cloned microorganism is obtained which contains the vector having the DNA containing the nucleotide sequence coding for GAF.

The above-mentioned step can be omitted by using, for example, known plasmid pETGAF1 (EP 0503297, *E. coli* DH-1/pGAF1 bearing said plasmid was deposited with NIBH under the accession number FERM BP-3547 on Sep. 2, 1991) in place of the plasmid thus obtained.

The above-mentioned cloned plasmid having the cDNA coding for the GAF can be used as it is or after digestion with a restriction enzyme if desired, depending on the intended purpose. The region intended to be expressed is cut out from the cloned cDNA and ligated downstream from a promoter in a vehicle (vector) suitable for expression, whereby the expression vector can be obtained.

The GAF polypeptides of the present invention can be produced by making the most of conventional recombinant DNA techniques. Chemical synthesis of oligonucleotides is easy. An oligonucleotide containing a translation initiating codon ATG or an oligonucleotide containing a translation terminating codon TAA, TAG or TGA is synthesized, and inserted into an appropriate site of the cDNA sequence coding for GAF, whereby an initiation or termination point of a peptide chain can be arbitrarily controlled to obtain a DNA coding for a desired N-terminus-deleted, C-terminus-deleted or both-deleted mutein. Further, an oligonucleotide coding for a desired amino acid sequence is synthesized, and inserted into a DNA coding for GAF, adjusting the oligonucleotide to a reading frame, whereby a DNA coding for a mutein to which the amino acid sequence is added can be produced. Furthermore, a DNA coding for a mutein in which a sequence is partially deleted can be produced by partially deleting a DNA coding for GAF, followed by recombination, adjusting amino acids to a reading frame.

In addition to the above-mentioned recombinant DNA techniques, site-directed mutagenesis is employed. This technique is well known and described in R. F. Lather and J. P. Lecoq, *Genetic Enqineering*, p.31–50, Academic Press (1983). Mutagenesis directed to oligonucleotides is described in M. Smith and S. Gillam, *Genetic Engineering: Principles and Methods*, Vol.3, p.1–32, Plenum Press (1981).

In a method for producing a mutagenized GAF gene to obtain GAF which is an N-terminus-deleted fragment of the polypeptide of SEQ ID NO:3 of the present invention, a gene codon coding for the carboxyl terminus of an amino sequence intended to be deleted is altered to ATG coding for MET by site-directed mutagenesis, and further, an appropriate recognition site for a restriction enzyme is formed on the 5'-terminal side of the codon, thereby making ligation with a promoter easy, or an oligonucleotide having ATG is ligated with a gene in which the amino terminus is deleted, adjusting ATG to a reading frame. Combinations of these techniques make it possible to produce the DNA coding for the desired GAF.

The gene coding for the GAF polypeptide as described above is ligated downstream from a promoter in a vehicle (vector) suitable for expression, whereby the expression recombinant vector can be obtained.

The vehicles (vectors) for producing the recombinant vectors include plasmids derived from *E. coli* such as pBR322 [*Gene*, 2, 95 (1977)], pBR325 [*Gene*, 4, 121 (1978)], pUC12 [*Gene*, 19, 259 (1982)], pUC13 [*Gene*, 19, 259 (1982)], pUC118 and pUC119, each derived from *E. coli*, pUB110 derived from *Bacillus subtilis* [*Biochemical and Biophysical Research Communication.*, 112, 678 (1983)], plasmids derived from *Bacillus subtilis* such as pUB110, pTP5 and pC194, plasmids derived from yeast such as pSH19 and pSH15, bacteriophages such as λ phage, and animal viruses such as retroviruses and vaccinia viruses.

The gene may have ATG as a translation initiating codon at the 5'-terminus thereof, and TAA, TGA or TAG as a translation terminating codon at the 3'-terminus thereof. A promoter is further ligated upstream therefrom to express the gene.

Any promoter may be used in this expression as long as it is suitable for expression in the host cell selected for the gene expression.

When the host cell used for transformation is a cell belonging to *Escherichia*, it is preferred that a T7 promoter, a trp promoter, a lac promoter, a recA promoter, a λPL promoter, or an l pp promoter is used. When the host cell is *Bacillus*, an SPO1 promoter, an SPO2 promoter, or a penP promoter is preferably used. When the host cell is yeast, a PHO5 promoter, a PGK promoter, a GAP promoter, or an ADH promoter is preferably used. In preferred embodiments of the present invention, the host cell is Escherichia and the promoter is a T7 promoter or a trp promoter.

When the host cell is an animal cell, a SV40-derived promoter, a retrovirus promoter or the like can be used. The SV40-derived promoter is preferred.

By using the vector containing the DNA thus constructed, the transformant is prepared.

Examples of the host cells include *Escherichia, Bacillus,* yeast and animal cells.

Examples of *Escherichia* include *E. coli* K12DH1 [*Proc. Natl. Acad. Sci. U.S.A.*, 60, 160 (1968)], M103 [*Nucleic Acids Research*, 4, 309 (1981)], JA221 [*Journal of Molecular Biology*, 120, 517, (1978)], HB101 [*Journal of Molecular Biology*, 41, 459 (1969)] and C600 [*Genetics*, 39, 440 (1954)].

Examples of the cells belonging to *Bacillus* described above include *Bacillus subtilis* MI114 [*Gene*, 24, 255 (1983)] and 207–21 [*Journal of Biochemistry*, 95, 87 (1984)].

Examples of the above-mentioned yeast include *Saccharomyces cerevisiae* AH22R⁻, NA87-11A and DKD-5D.

As the above-mentioned animal cells, cell lines are preferably used, and examples thereof include monkey cell COS-7, Vero, Chinese hamster cell (CHO), mouse L cell and human FL cell.

The transformation of *Escherichia* described above is conducted, for example, according to the method described in *Proc. Natl. Acad. Sci. U.S.A.*, 69, 2110 (1972), *Gene*, 17, 107 (1982) or the like.

The transformation of *Bacillus* is carried out, for example, according to the method described in *Molecular & General Genetics*, 168, 111 (1979) or the like.

The transformation of the yeast is performed, for example, according to the method described in *Proc. Natl. Acad. Sci. U.S.A.*, 75, 1929 (1978).

The transformation of the animal cells is carried out, for example, according to the method described in *Virology*, 52, 456 (1973).

Thus, the transformant transformed with the expression vector containing the cDNA coding for GAF is obtained.

When the bacterial transformants are cultivated, a liquid medium is typically used for cultivation. Carbon sources, nitrogen sources, inorganic compounds and other nutrients necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast, vitamins and growth promoting factors may be further added.

The pH of the medium is preferably about 5 to about 8.

When the *Escherichia* transformants are cultivated, M9 medium containing glucose and Casamino Acids [Miller, *Journal of Experiments in Molecular Genetics*, 431–433, Cold Spring Harbor Laboratory, New York (1972)] is preferably used to cultivate the transformants. In order to allow the promoters to act more efficiently, for example, drugs such as 3β-indolyl acrylic acid may be added thereto if necessary.

The *Escherichia* transformants are usually cultivated at about 15 to about 43° C. for about 3 to about 24 hours with aeration or agitation if necessary.

The *Bacillus* transformants are usually cultivated at about 30 to about 40° C. for about 6 to about 24 hours with aeration or agitation if necessary.

When the yeast transformants are cultivated, the preferred medium is Burkholder minimum medium [K. L. Bostian, *Proc. Natl. Acad. Sci. U.S.A.*, 77, 4505 (1980)]. The pH of the medium is preferably adjusted to about 5 to about 8. The cultivation is usually carried out at about 20 to about 35° C. for about 24 to about 72 hours with aeration or agitation if necessary.

When the animal cell transformants are cultured, examples of media include MEM medium containing about 0 to about 20% fetal calf serum [*Science*, 122, 501 (1952)], DMEM medium [*Virology*, 8, 396 (1959)], RPMI1640 medium [*Journal of the American Medical Association*, 199, 519 (1967)] and 199 medium [*Proceeding of the Society for the Biological Medicine*, 73, 1 (1950)]. The pH is preferably about 6 to about 8. The cell cultivation is usually carried out at about 30 to about 40° C. for about 15 to about 60 hours, with aeration or agitation if necessary.

The isolation and purification of the GAF polypeptides from the culture products can be carried out, for example, according to the following method.

First, the cells are collected by known methods after cultivation. Then, the collected cells are suspended in a buffer solution or a solution containing a protein denaturant such as guanidine hydrochloride, and disrupted by ultrasonic treatment, lysozyme treatment and/or freeze-thawing thereby releasing GAF, followed by centrifugation to obtain GAF. It is particularly preferred to use lysozyme treatment in combination with ultrasonic treatment.

The separation and purification of the GAF polypeptides from the supernatant obtained above can be carried out by appropriate combinations of well-known separating and purifying methods. These known separating and purifying methods include methods utilizing a difference in solubility such as salting-out and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography, methods utilizing a difference in specific affinity such as affinity chromatography, and methods utilizing a difference in hydrophobicity such as reverse phase high performance liquid chromatography.

In particular, affinity chromatography using the antibodies of the present invention is preferably used for purification of the GAF polypeptides.

More specifically, the above-mentioned supernatant can be subjected to ion-exchange chromatography with DEAE cellulose, thereby remove contaminants such as nucleic acid and acidic proteins. For example, it is effective to load the supernatant on a DEAE cellulose column equilibrated with a nearly neutral buffer solution such as Tris and to collect fractions not adsorbed by the column. Further, the GAF polypeptide can also be purified by ion-exchange chromatography using CM cellulose in which the GAF polypeptide is adsorbed by the carrier and eluted with a salt solution.

The GAF polypeptides can be directly purified from cell extracts by column chromatography with an acidic resin such as CM Sephadex. For example, the supernatant is loaded on a CM-Sephadex column equilibrated with a weak acidic buffer solution (for example, phosphate buffer), and the column is washed with the same buffer solution, followed by elution with a buffer solution further containing a salt (for example, NaCl), thereby being capable of eluting the GAF polypeptide efficiently. The eluate can be lyophilized after dialysis.

Affinity chromatography with heparin-Sepharose is also advantageously applied to purification of the GAF polypeptides in *E. coli* extracts. For example, an eluate is loaded on a heparin-Sepharose column equilibrated with a nearly neutral buffer solution such as Tris or phosphate buffer, and the column is thoroughly washed. Then, linear gradient elution is accomplished by use of a salt such as NaCl, whereby the GAF polypeptide can be purified.

In particular, heparin columns for high performance liquid chromatography (for example, ShodexAF-pak HR-894, Showa Denko K. K., Japan) are effective.

A sample is subjected to the column equilibrated with a nearly neutral buffer solution, and the column is thoroughly washed, followed by elution with linear gradient of NaCl or the like, whereby the GAF polypeptide can be recovered as an almost homogeneous sample.

The sample thus obtained can also be dialyzed and lyophilized to form a dried powder. The addition of serum albumin as a carrier can suitably prevent the sample from being adsorbed by a container during storage.

The use of a trace amount of reducing agent in the purification process or the storage process is suitable for preventing oxidation of the sample. Preferred reducing agents include β-mercaptoethanol, dithiothreitol and glutathione.

Thus, the substantially pure GAF polypeptides substantially free from pyrogens and endotoxins are obtained. The substantially pure GAF polypeptides include polypeptides containing GAF in a polypeptide content of about 95% (w/w) or more. The substantially pyrogen and endotoxin free product reacts negatively in the limulus lysate test. The biological activity of the GAF polypeptides thus prepared can be assayed, for example, by the method of Naruo et al. [*Journal of Biological Chemistry*, 268, 2857 (1993)], namely by growth promoting activity based upon the uptake of $^3$H-thymidine by primary culture glial cells isolated from the brain of a rat fetus (19 days after fertilization) or by BALB/c 3T3 cells.

Further, MK-CSF activity can be assayed by culturing mouse bone marrow cells and counting the number of megakaryoblasts.

GAF is a growth factor produced in the brain or the kidney in vivo, and it has been proved that it acts on not only mesoblast cells, but also megakaryoblasts to promote their growth. Excessive action on these cell lines can conceivably be responsible for tumorigenesis of the cells.

The neutralizing antibodies of the present invention inhibit action of GAF to exhibit antitumor activity, possibly because they have strong neutralizing activity. In this case, the antibodies are conceivably given, for example, in doses of about 10 μg to about 10 mg/kg, intravenously, subcutaneously or intraperitoneally. They can be used in combination with other stabilizing agents, immunostimulants or chemotherapeutants.

Fragments in which 33 to 49 amino acids are deleted from the N-terminus of the polypeptide represented by SEQ ID NO:3 is more stable against acid or heat than conventional GAF and can be safely given parenterally or orally to mammals (for example, humans, mice, rats, hamsters, rabbits, dogs and cats), as a therapeutic agent for cerebral nervous diseases, an osteogenesis promoting agent or a platelet increasing agent, similarly with conventional GAF, in a powder form as such or in a pharmaceutical composition (for example, an injection, a tablet, a capsule, a solution or an ointment) with pharmaceutically acceptable carriers, excipients (for example, stabilizing agents such as human serum albumin and sorbitol) and diluents. In particular, it is preferably given parenterally as an injection. Thus, the fragments are stable without coexistence of heparin or cyclodextrin which has anticoagulation activity, it is more advantageous for pharamaceutical use.

The polypeptides of the present invention can be used as activating agents for hepatic cells and can be used for hepatopathy such as hepatic cirrhosis because they accelerate growth of hepatic parenchymal cells. Also in this case, they are conceivably given, for example, as injections intravenously, subcutaneously or intraperitoneally. In this cases, the polypeptides are given, for example, in doses of about 100 ng to about 100 µg/kg, and can also be used in combination with other factors or stabilizing agents.

The polypeptides of the present invention can be used not only alone, but also as mixtures or in combination with other platelet increasing agents, leukocyte increasing agents (such as G-CSF, M-CSF, CM-CSF and IL-3), immunostimulants or erythrocyte increasing agents, which are different in mechanism of action.

The pharmaceutical compositions are prepared in accordance with known pharmaceutical manufacturing methods, using pharmaceutically acceptable additives, diluents, excipients and the like if desired.

For example, aqueous liquid formulations for injection are prepared by conventional methods, using solvents such as aqueous solvents (for example, distilled water), water-soluble solvents (for example, physiological saline and Ringer solution) and oily solvents (for example, sesame oil and olive oil), or additives such as solubilizing adjuvants (for example, sodium salicylate and sodium acetate), buffers (sodium citrate and glycerin), isotonic agents (for example, glucose and invert sugar), stabilizing agents (for example, human serum albumin and polyethylene glycol), preservatives (for example, benzyl alcohol and phenol), and soothing agents (for example, benzalkonium chloride and procaine hydrochloride) if desired.

Further, solid formulations for injection can be prepared by conventional methods, incorporating diluents (for example, distilled water, physiological saline and glucose), excipients (for example, carboxymethyl cellulose (CMC) and sodium alginate), preservatives (for example, benzyl alcohol, benzalkonium chloride and phenol), soothing agents (for example, glucose, calcium gluconate and procaine hydrochloride) and the like.

Furthermore, in preparing the formulations, monosaccharides such as glucose, amino acids, various salts, human serum albumin and the like may be added. In addition, isotonic agents, pH-regulating agents, soothing agents, antiseptics and the like can be added to prepare stable, effective formulations.

The therapeutic agent, for example, platelet-increasing agents of the present invention can be given at an appropriate dosage selected from the range of about 1 ng to about 1000 µg/kg of body weight daily, preferably about 10 ng to about 100 µg/kg, and more preferably about 100 ng to about 100 µg/kg, in several divided doses as required, taking into account the routes of administration, symptoms and the like.

Examples of parenteral administration of the therapeutic agents of the present invention include intravenous administration, subcutaneous administration, intramuscular administration, administration in medullary cavity, and administration through mucosa. The routes of administration through mucosa include nasal, intraoral and intrarectal routes.

In particular, intravenous administration and subcutaneous administration are preferred. The therapeutic agents may be given once a day or in several divided doses or by continuous intravenous drip infusion. They may be given intermittently, for example, about once for every 3 days or about once a week.

Further, the therapeutic agents may be given as sustained release preparations. Examples of such sustained release preparations include microcapsules and imbedding agents. In particular, the sustained release preparations are preferably imbedded subcutaneously to allow the bases to exhibit their effect for a long period of time.

Administration of the platelet-increasing agents of the present invention can increase the number of platelets in the peripheral blood. In chemotherapy of cancers, administration of almost all chemotherapeutics induces a decrease in the number of platelets, which hinders administering the chemotherapeutics in sufficient amounts. The same is true for radiotherapy. A decrease in the number of platelets is observed at about 3 to about 15 days after administration of the chemotherapeutics. The platelet-increasing agents of the present invention show platelet-increasing action at about 5 to about 10 days after administration, so that they can be given immediately after administration of the chemotherapeutics, or after observation of a decrease in the number of platelets to restore the number of platelets. Furthermore, they can also be administered to previously increase the number of platelets by giving the platelet-increasing agents of the present invention before administration of the chemotherapeutics.

The platelet-increasing agents of the present invention can increase platelets in number to restore the number of platelets decreased by chemotherapy, thereby enhancing the effect of treatment and restoring patients from serious symptoms.

Thus, platelet-increasing agents of the present invention can be used as anticancer aids as long as the cancer growth is not promoted by GAF. The cancer cell sensitive against GAF can be detected by the assay using GAF polypeptide or antibody of the present invention.

Examples of anticancer agents used as the chemotherapeutics include alkylating agents (for example, nitrogen mustard N-oxide, cyclophosphamide, melphalan, carboquone, busulfan, nimustine hydrochloride, ranimustine and dacarbazine), antimetabolites (for example, fluorouracil, tegaful, cytarabine, ancitabine hydrochloride, broxuridine, doxifluridine, mercaptopurine, thioinosine and methotrexate), antibiotics (for example, mitomycin, bleomycin, daunorubicin hydrochloride, doxorubicin hydrochloride, pirarubicin hydrochloride, aclarubicin hydrochloride, neocarzinostatin and actinomycin D), plant alkaloids (for example, vincristine sulfate, vindesine sulfate, vinblastine sulfate and etoposide), hormone agents (for example, tamoxifen citrate), platinum coordination component (for example, carboplatin, cisplatin) and others (for example, procarbazine hydrochloride, mitobronitol and mitoxanton hydrochloride).

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
A: Adenine
T: Thymine
G: Guanine C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine Transformants and animal cells obtained in Reference Examples and Examples described below were deposited with the IFO, and with the NIBH under the Budapest Treaty. Their accession numbers and deposit dates are shown in Table 1.

TABLE 1

| Transformant | IFO IFO No. | NIBH FERM BP-No. |
| --- | --- | --- |
| E. coli DH1/pGAF1 | 15217 (1991,8,28) | 3547 (1991,9,2) |
| E. coli MM294(DE3)/pLysS, pETGAF1 | 15248 (1991,12,3) | 3689 (1991,12,24) |
| E. coli MM294(DE3)/pLysS, pETGAF25 | 15503 (1993,6,29) | 4354 (1993,7,6) |
| Mouse hybridoma GAF 150-59 | 50385 (1992,12,21) | 4143 (1993,1,7) |
| Mouse hybridoma GAF 40-20 | 50384 (1992,12,21) | 4142 (1993,1,7) |
| Mouse hybridoma GAF 13-3 | 50383 (1992,12,21) | 4141 (1993,1,7) |
| Mouse hybridoma GAF 4-82 | 50408 (1993,09,14) | 4428 (1993,9,29) |

The present invention will be described in more detail through Reference Examples and Examples shown below. It is understood of course that they are not intended to limit the scope of the invention.

REFERENCE EXAMPLE 1

(1) Expression of GAF (N3) in *E. coli*

Construction of GAF Expression Plasmid pETGAF1

Figure 2:
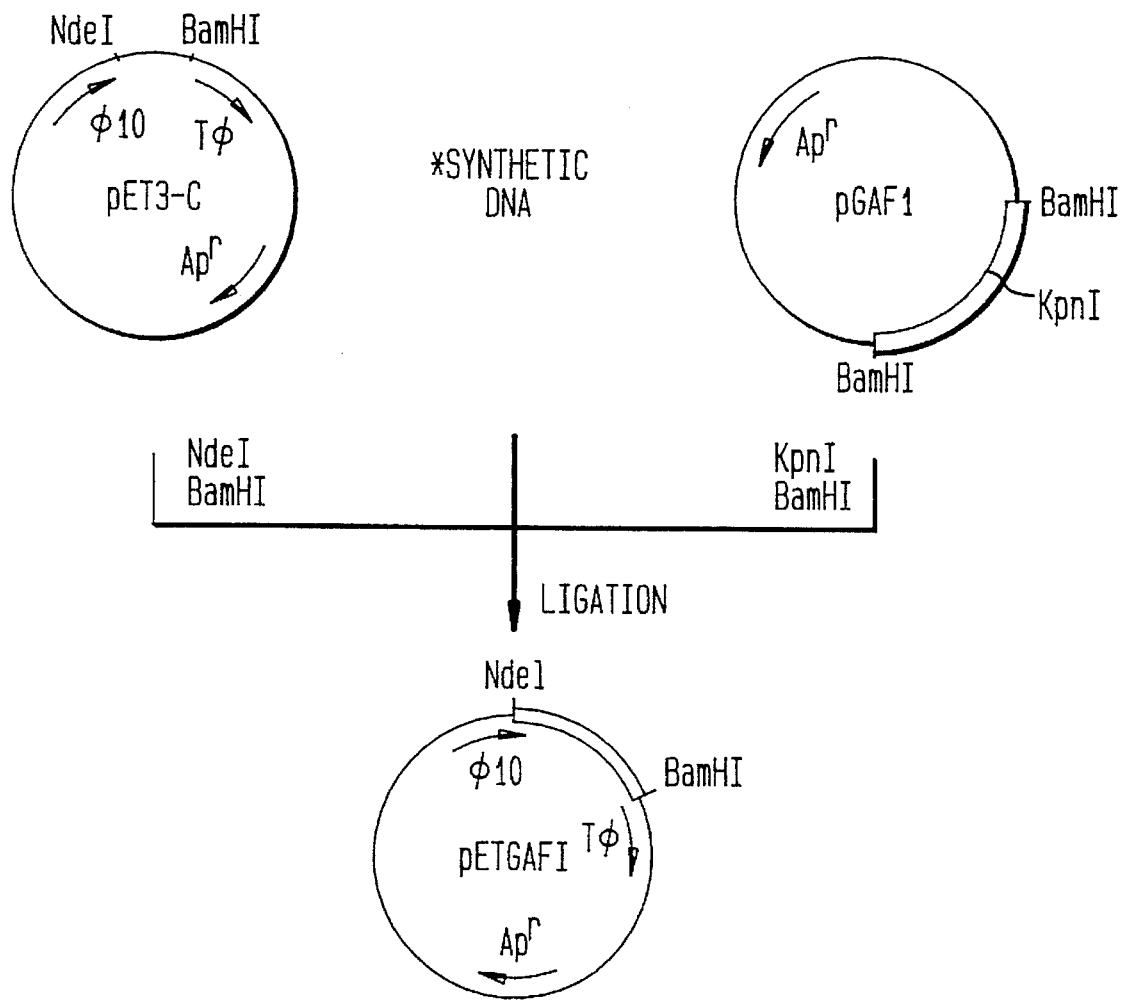
FIG. 2 is a schematic representation showing the construction of plasmid pETGAF1.
Figure 3:
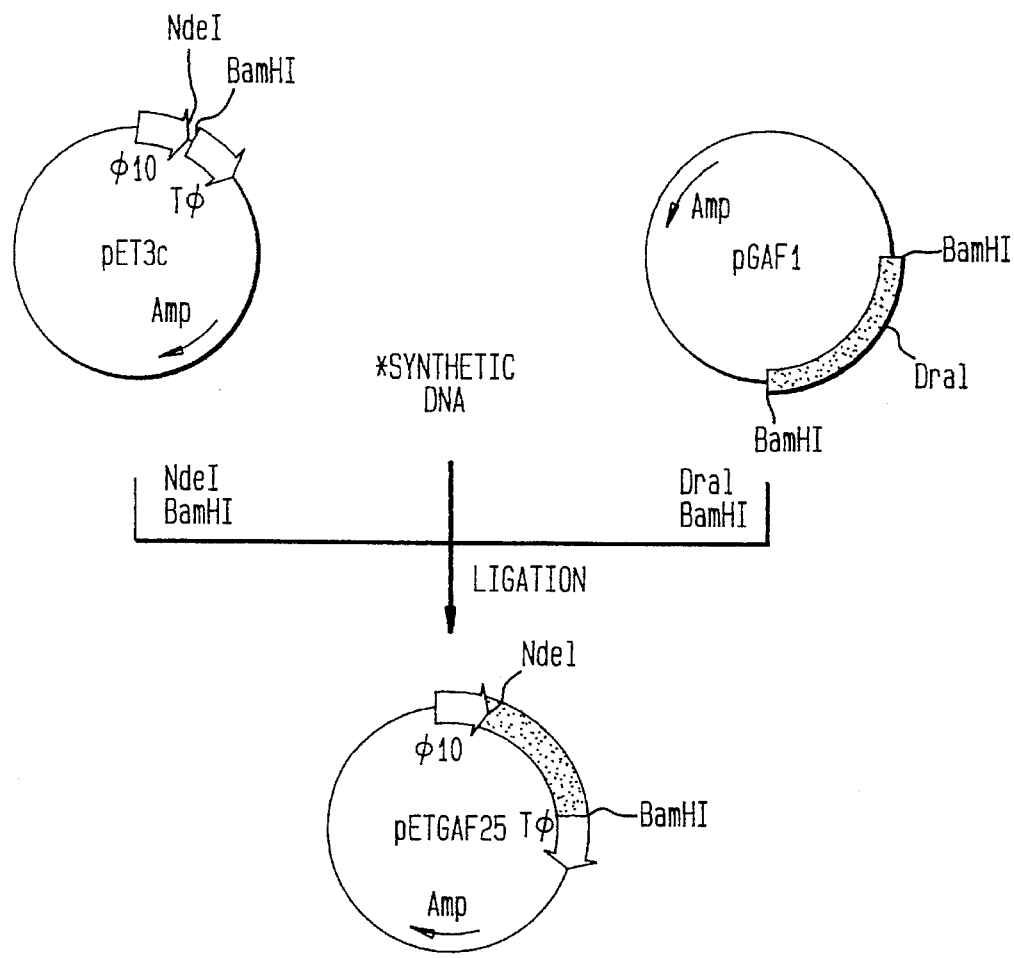
FIG. 3 is a schematic representation showing the construction of pETGAF25.

Plasmid pGAF1 containing the whole structure gene of human GAF described in EP 0503297 was cleaved with restriction enzyme KpnI-BamHI, and a 1.25-kb cDNA fragment was isolated. Similarly, plasmid pET3-c containing a T7 promoter was cleaved with restriction enzyme NdeI-BamHI, and a 4.6 kb DNA was isolated, followed by insertion therein of the above-mentioned 1.25-kb fragment of the GAF cDNA and synthesized DNA fragments (NdeI-KpnI) [(SEQ ID NO:10) and (SEQ ID NO:11)] which bring Met just ahead of Leu, the fourth amino acid from the N-terminus of the GAF polypeptide represented by SEQ ID NO:3. In this manner, expression plasmid pETGAF1, which could express the GAF cDNA under the control of the T7-promoter, was constructed. This plasmid expresses a polypeptide chain corresponding to the 30 kDa GAF molecular species purified from gliomas. This 30 kDa GAF polypeptide is hereinafter also referred to as "N3". The construction schematic of plasmid pETGAF1 is shown in FIG. 2. Using this plasmid, *E. coli* MM294(DE3)/pLysS was transformed to obtain N3 expression transformant *E. coli* MM294(DE3)/pLysS, pETGAF1.

MM294(DE3)/pLysS, pETGAF1 was cultivated in LB medium, and expression of N3 was induced by isopropyl-β-D(-)-thiogalactoside (Wako Pure Chemical Industries, Ltd., Japan). Then, polypeptides exatracted from the cells corresponding to 200 μl of the culture solution were examined by Western Blotting method using rabbit anti-GAF polyclonal anti-serum (500-fold dilution) recognizing the N-terminal portion of the GAF polypeptide. As a result, a specific band was observed. Transformant MM294(DE3)/pLysS, pET3-C which was transformed with plasmid pET3-c having no GAF cDNA did not produce the band.

(2) Extraction of Human GAF (N3) Produced in *E. coli*

*E. coli* MM294(DE3)/pLysS, pETGAF1 was cultivated with shaking at 37° C. in LB medium supplemented with 50 μg/ml ampicillin and 10 μg/ml chloramphenicol. When the Klett value of the culture solution reached 120, isopropyl-β-D(-)-thiogalactoside was added to a final concentration of 0.4 mM, and the culture was further cultivated with shaking at 37° C. for 3.5 hours. The cells collected from 1 liter of the culture solution by centrifugation (6,000 rpm, for 10 minutes) were suspended on ice in 80 ml of 20 mM Tris-HCl buffer supplemented with 2 mM (p-amidinophenyl) methanesulfonyl fluoride hydrofluoride (Wako Pure Chemical Industries, Japan), 100 μg/ml egg white lysozyme (Seikagaku Kogyo K. K., Tokyo, Japan) and 0.1M NaCl, and the resulting suspension was allowed to stand at 4° C. for 1 hour, followed by incubation at 37° C. for 3 minutes. The suspension thus obtained was cooled with ice and subjected to ultrasonic treatment [Sonifier Cell Disruptor 200 (registered trade mark), Branson, U.S.A., at an output of 8 for 2 minutes]. An *E. coli* extract was obtained by centrifugation at 17,000 rpm for 40 minutes.

(3) Purification of Human GAF (N3) Produced in *E. coli*

Step 1: Ammonium sulfate precipitation
To 80 ml of the *E. coli* extract obtained from 1 liter of the above culture solution, 27 ml of saturated aqueous solution of ammonium sulfate was added, followed by mixing. Then, the mixture was allowed to stand at 4° C. overnight. Subsequently, the mixture was centrifuged at 17,000 rpm for 40 minutes to obtain a supernatant.

Figure 5:
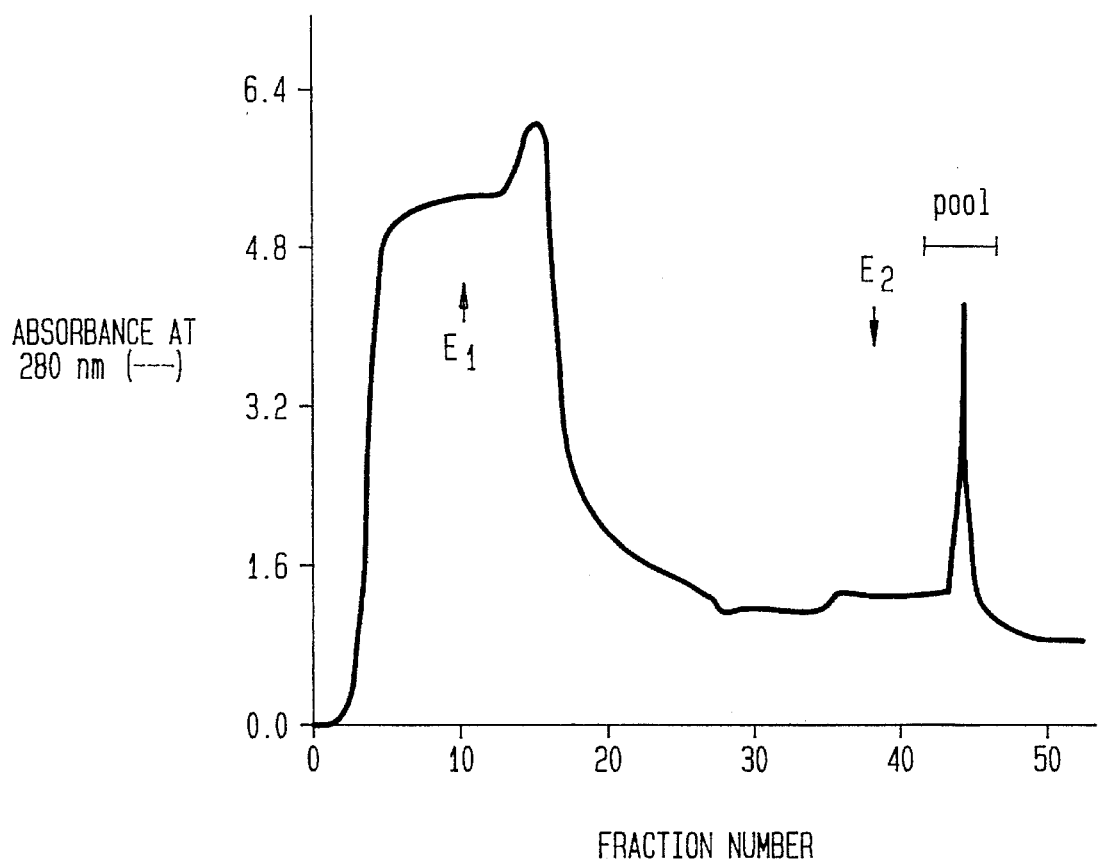
FIG. 5 shows a protein elution pattern on hydrophobic column chromatography (Reference Example 1 (3), step 2).

Step 2: Hydrophobic column chromatography
100 ml of the centrifuged supernatant obtained in step 1 was passed through a Butyl-Toyopearl column 650M (bed volume: 50 ml, 2.5 cm in internal diameter×10 cm in length, Tosoh Corp. Tokyo, Japan) equilibrated with 20 mM Tris-HCl buffer (pH 7.6) supplemented with 25% saturated ammonium sulfate solution, at a flow rate of 80 ml/hour at 4° C. The resin was thoroughly washed with 20 mM Tris-HCl buffer (pH 7.6) supplemented with 12.5% saturated ammonium sulfate solution and 2 mM aPMSF, and then, GAF polypeptide-containing fractions were obtained by elution with 20 mM Tris-HCl buffer (pH 7.6) supplemented with 15% glycerin, 0.1% CHAPS and 2 mM aPMSF (80 ml/hour, 10 ml/fraction, 4° C.) (FIG. 5). In FIG. 5, $E_1$ indicates elution with 20 mM Tris-HCl buffer (pH 7.6) supplemented with 12.5% saturated ammonium sulfate solution and 2 mM aPMSF, and $E_2$ indicates elution with 20 mM Tris-HCl buffer (pH 7.6) supplemented with 15% glycerin, 0.1% CHAPS and 2 mM aPMSF.

Step 3: Heparin affinity high performance liquid column chromatography

Figure 6:
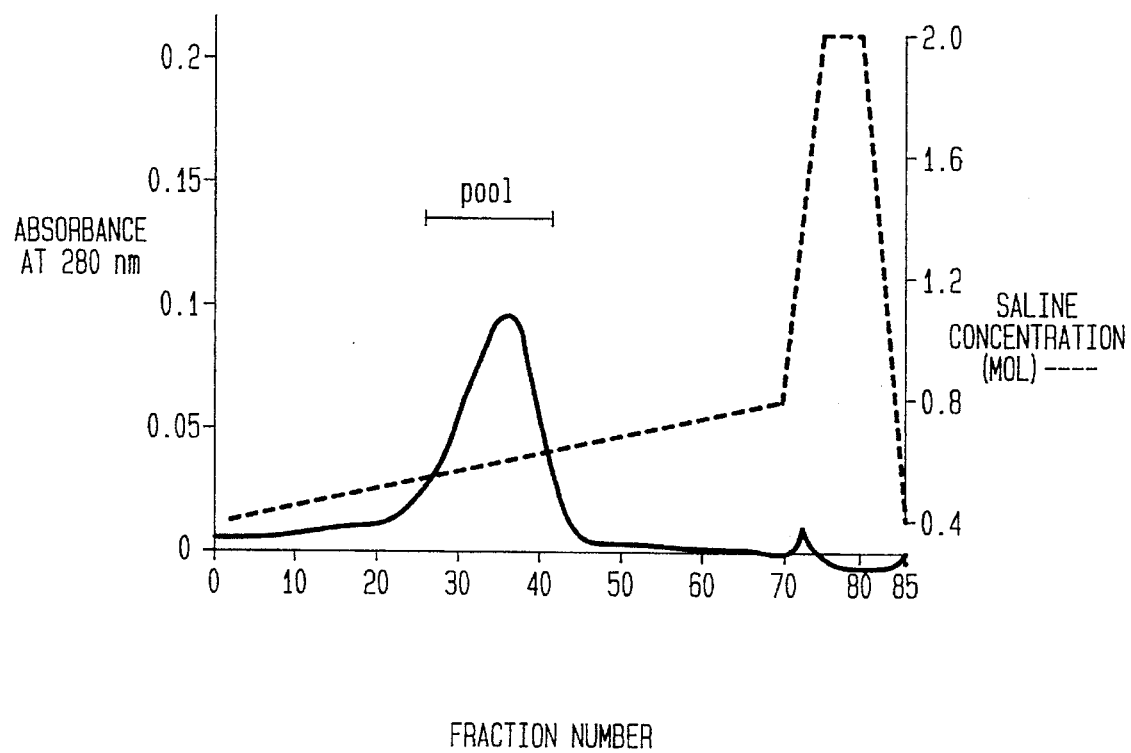
FIG. 6 shows a protein elution pattern on heparin affinity high performance liquid column chromatography (Reference Example 1 (3), step 3).
Figure 7:
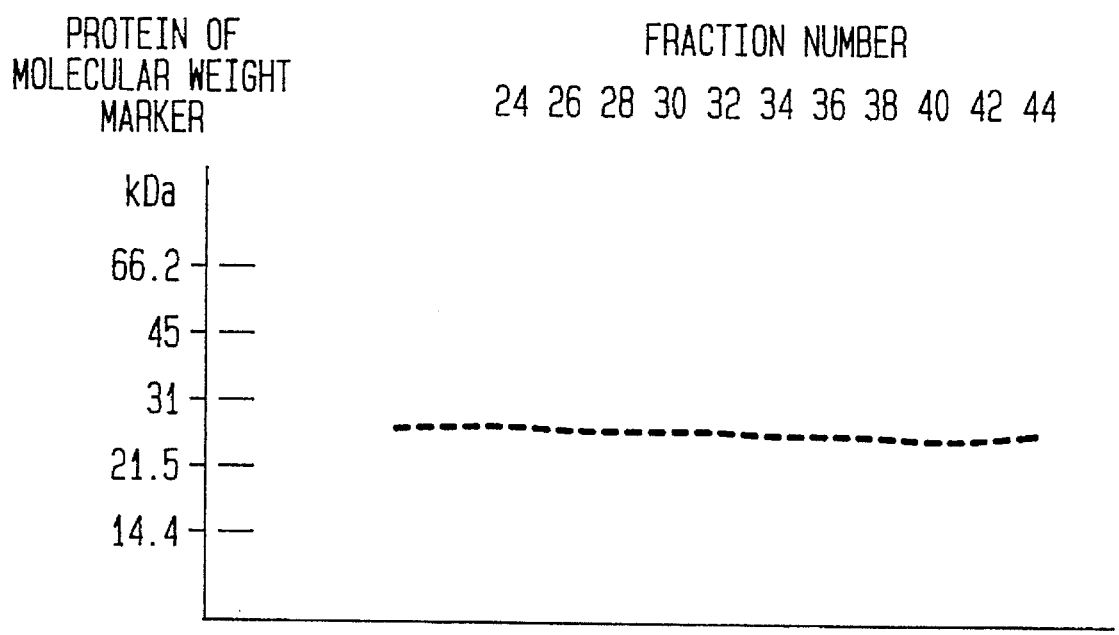
FIG. 7 shows an SDS polyacrylamide gel electrophoresis diagram of purified GAF.

The GAF polypeptide-containing fractions (fractions 44 to 47) obtained in step 2 were pooled (40 ml). Of 40 ml of this solution, 36 ml was applied to high performance liquid column chromatography (Gilson Medical Electronics, France) equipped with an HR-894 column (8 mm in diameter×50 mm in length, Showa Denko K. K., Japan). The polypeptide adsorbed by the resin was eluted at a flow rate of 2 ml/minute by linearly increasing the concentration of NaCl and fractionated (2 ml/fraction). Buffer A used was 10 mM Tris-HCl buffer (pH 7.6) containing 0.4M NaCl, 0.1% CHAPS and 15% glycerin, and buffer B was 10 mM Tris-HCl buffer (pH 7.6) containing 2M NaCl, 0.1% CHAPS and 15% glycerin. The program of elution was as follows:

0 minute (100% A)–70 minutes (75% A+25% B)–75 minutes (100% B)–80 minutes (100% B)–85 minutes (100% A) (FIG. 6)

The column temperature was room temperature.

Figure 4:
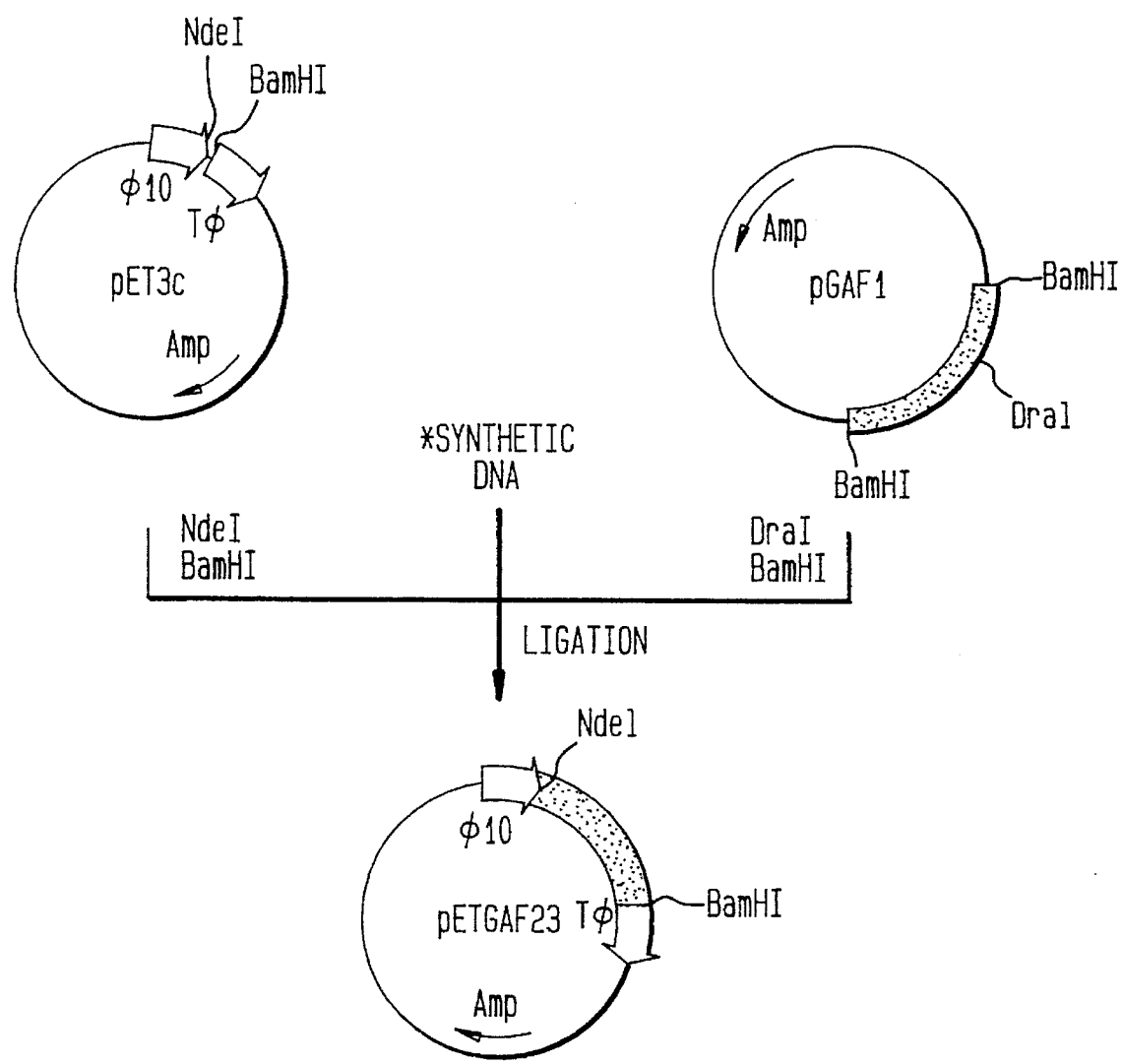
FIG. 4 is a schematic representation showing the construction of pETGAF23.

One microliter each of eluted fractions was subjected to SDS-polyacrylamide gel electrophoresis (gel concentration: 12.5%) in the presence of 2-mercaptoethanol, followed by silver staining. Results thereof are shown in FIG. 4. Fractions eluted by increasing the concentration of NaCl gave a single band at 27 kDa. This 27 kDa polypeptide was recognized by rabbit anti-GAF polyclonal anti-serum which binds to the N-terminal portion of GAF. Fractions 27 to 42 were pooled.

(4) Summary of Purification

The summary of purification of GAF (N3) obtained from 1 liter culture of the *E. coli* MM294(DE3)/pLysS, pETGAF1 is shown in Table 2.

TABLE 2

| Sample | Total protein amount (mg) | Total activity (U) | Specific activity (U/mg) | Activity Recovery (%) | Purification |
|---|---|---|---|---|---|
| *E. coli* extract | 672 | $4.16 \times 10^7$ | $6.19 \times 10^4$ | 100 | 1 |
| 25% saturated ammonium sulfate supernatant | 210 | $4.35 \times 10^7$ | $2.07 \times 10^5$ | 105 | 3.3 |
| Butyl Toyopearl | 37.6 | $4.10 \times 10^6$ | $1.09 \times 10^5$ | 10 | 1.8 |
| Heparin HPLC | 4.5 | $3.31 \times 10^6$ | $7.35 \times 10^5$ | 8.0 | 12 |

The biological activity was assayed by the method described in Reference Example 2 except that varied amount of GAF N3 was added to the reaction mixture in stead of 1 ng/ml of 25-kDa GAF and hybridoma culture supernatant. The biological activity (U) is expressed as the reciprocal of the dilution ratio of the sample having a 50% uptake value of tritium thymidine, wherein a 100% uptake value of tritium thymidine is defined as the uptake of tritium thymidine in a medium of 10% fetal calf serum. The amount of the polypeptide was determined by a MicroBCA kit (Pierce, U.S.A.) using bovine serum albumin as a standard.

EXAMPLE 1

(1) Production of N-Terminal 33 Amino Acid-Deleted GAF (N33)

Plasmid pGAF1 described in Reference Example 1 was cleaved with restriction enzyme DraI-BamHI, and a 1.2-kb CDNA fragment was isolated. Similarly, plasmid pET3c containing a T7 promoter was cleaved with restriction enzyme NdeI-BamHI, and a 38 bp DNA was removed, followed by insertion therein of the above-mentioned 1.2-kb fragment of the GAF cDNA and synthesized DNA fragments (NdeI-DraI) [(SEQ ID NO:12) and (SEQ ID NO:13)] which code translation initiating codon ATG just ahead of Ser, the 34th amino acid from the N-terminus of the GAF polypeptide represented by SEQ ID NO:3. In this manner, expression plasmid pETGAF25, which could express a GAF molecule in which 33 amino acids were deleted form the N-terminal side of the polypeptide of SEQ ID NO:3 under the control of the T7-promoter, was constructed. This molecule is a polypeptide chain corresponding to the 25 kDa GAF molecular species purified from glioma cells. This molecule is hereinafter referred to "N33".

Using this plasmid, *E. coli* MM294(DE3)/pLysS was transformed to obtain N33 expression transformant *E. coli* MM294(DE3)/pLysS, pETGAF25.

The cultivation of *E. coli* and the purification of GAF (N33) from the cells were conducted in the same manner as with N3.

(2) Purification of Mutein N33

Regarding the purification of N33, the following method was also used. *E. coli*MM294(DE3)/pLysS, pETGAF25 collected from 1 liter of the culture solution by centrifugation (6,000 rpm, for 10 minutes) were suspended on ice in 100 ml of 20 mM Tris-HCl buffer supplemented with 2 mM (p-amidinophenyl) methanesulfonyl fluoride hydrofluoride (Wako Pure Chemical Industries, Japan), 100 μg/ml egg white lysozyme (Seikagaku kogyo K. K., Tokyo, Japan) and 0.3M NaCl, and the resulting suspension was blended with beads (MAHLKOERPER MK-2GX (DR) 0.25–0.5 mmϕ, Willy A.Bachofen Basal. Switzerland)(vol.30 ml) at 0° C. (4 minutes mix and stand for 2 minutes, 6 sets). An *E. coli* extract was obtained by centrifugation (SORVALL, 11,000 rpm 30 minutes 14° C.). To the extract saturated aqueous solution of ammonium sulfate was added to a final concentration of 20%, followed by mixing. After the mixture was allowed to stand at 4° C. for 30 minutes, centrifuged at 17,000 rpm for 40 minutes (SORVALL 4° C.) to obtain a precipitate. The centrifuged precipitate was dissolved on ice into 50 ml of 20 mM Tris-HCl buffer(pH 7.6) supplemented with 0.15M NaCl and 0.1% CHAPS and placed on a DEAE-Toyopearl 650S column (bed volume, 150 ml, Tosoh Corp. Tokyo Japan) equilibrated with 50 ml of 20 mMTris-HCl buffer (pH 7.6) supplemented with 0.15M NaCl and 0.1% CHAPS.

The column was washed with the same buffer, and the fraction passed through the column was collected (fr.11–18, total amount 80ml). After filtration, the obtained solution was applied to a heparin-column (Shodex HR-894, 8φ×50 mm) equilibrated with 10mM Tris-HCl buffer (pH 7.6) supplemented with 0.2M NaCl. After the column was washed with the same buffer, the polypeptide was eluted by gradient elution of 0.2M–2M NaCl. (flow rate: 1 ml/min, 60 min)

When fractions eluted from the heparin affinity column in Example 1-(1) are subjected to polyacrylamide gel electrophoresis, a major protein peak observed at in the vicinity of 0.8M NaCl gave a single band at 22 kDa, and recognized by a rabbit anti-GAF C-terminal antibody induced by the C-terminal peptide of GAF.

Fractions 36 to 42 corresponding to this peak were pooled to prepare a purified sample.

The summary of purification of N33 obtained from 1 liter culture of the E. coli MM294(DE3)/pLysS, pETGAF25 is shown in Table 3.

TABLE 3

| Sample | protein amount (mg) | Total activity (U) | Specific activity (U/mg) | Activity recovery (%) |
|---|---|---|---|---|
| Crude extract | 322.5 | 933 × 10⁵ | 2.89 × 10⁵ | 100 |
| Ammonium sulfate precipitate | 300.5 | 788 × 10⁵ | 2.62 × 10⁵ | 84 |
| DEAE-Toyopearl | 242.1 | 416 × 10⁵ | 1.72 × 10⁵ | 45 |
| Heparin HPLC | 6.1 | 183 × 10⁵ | 3.00 × 10⁶ | 20 |

EXAMPLE 2

(1) Construction of N-Terminal 49 Amino Acid-Deleted GAF N49 Expression Plasmid

A 1.2-kb DraI-BamHI fragment of GAF cDNA obtained in the same manner as with Example 1 and synthesized DNA fragments (NdeI-DraI) which code translation initiating codon ATG just ahead of Ala, the 50th amino acid from the N-terminus of the GAF polypeptide represented by SEQ ID NO:3 are inserted. In this manner, expression plasmid pETGAF23, which could express GAF in which 49 amino acids were deleted from the N-terminus of the polypeptide of SEQ ID NO:3 (hereinafter also referred to as "N49") under the control of the T7-promoter, was constructed. The construction schematic of plasmid pETGAF23 is shown in FIG. 4. Using this plasmid, E. coli MM294(DE3)/pLysS was transformed to obtain N49 expression transformant E. coli MM294(DE3)/pLysS, pETGAF23.

(2) Purification of Mutein N49

E. coli MM294(DE3)/pLysS, pETGAF23 obtained in (1) described above was purified in the same manner as with Example 2-(2) to prepare a cell extract, and purified in the same manner as with Example 2-(3). The recovery of N49 was approximately equal to that of N33.

EXAMPLE 3

(Preparation of Monoclonal Antibody)

(1) Immunization

BALB/c mice (female, 8 weeks old) were subcutaneously injected with 100 μg of human GAF (N33) dissolved in 0.1 ml of physiological saline daily for 10 days. After 3 weeks, 100 μg of GAF (N33) dissolved in 0.1 ml of physiological saline was inoculated into the caudal veins of the mice.

(2) Cell Fusion

Four days after the final inoculation, the spleens were removed from the mice immunized in (1) to obtain cells to be used for cell fusion. These cells isolated from the spleans were suspended in RPMI-1640 medium.

Mouse myeloma cells P3-X63-Ag.SUI were subcultured in RPMI-1640 medium supplemented with 10% fetal calf serum under an atmosphere of 5% carbon dioxide and 95% air.

Cell fusion was carried out according to the method established by Köhler and Milstein [G. Köhler and C. Milstein, Nature, 256., 495 (1975)]. The above-mentioned myeloma cells ($2.9 \times 10^7$ cells) were mixed with the immunized lymphocytes ($1.5 \times 10^8$ cells) obtained by the above-mentioned method, and the mixture was centrifuged. Then, 0.3 ml of a 45% solution of polyethylene glycol 6000 (hereinafter, PEG 6000) in RPMI-1640 was added dropwise thereto. The PEG 6000 solution was preheated to 37° C. and slowly added. After 5 minutes, RPMI-1640 medium preheated to 37° C. was added thereto at a rate of 0.5 ml/min to make up a 10-ml volume. Then, the solution was centrifuged at room temperature at 600 rpm for 15 minutes to remove a supernatant. The resulting cell precipitate was suspended in 200 ml of PRMI-1640 supplemented with 20% calf serum. The suspension was seeded in a 96-well microtiter plate (Nunc) in an amount of 100 μl/well. One day later, RPMI-1640 medium (containing 20% calf serum) supplemented with HAT ($1 \times 10^{-4}$M hypoxanthine, $4 \times 10^{-7}$M aminopterin, $1.6 \times 10^{-5}$M thymidine) (hereinafter, HAT medium) was added to the microtiter plate in an amount of 100 μl/well. Further every 3 days, one-half the amount of the medium was changed with HAT medium. The cells which thus grew were hybrid cells.

(3) Screening for Antibody-Producing Cells

The culture supernatant of hybrid cells was added in an amount of 100 μl/well to a 96-well polystyrene microtiter plate to which human GAF (N33) had previously been fixed, and incubated at room temperature for 2 hours. After removal of the resulting supernatant and washing, the HRP-labeled anti-mouse IgG goat antibody (Miles) was added as a secondary antibody, and incubated at room temperature for 2 hours. The secondary antibody was removed, and the wells were thoroughly washed, followed by addition of a substrate to conduct coloring reaction (EIA method). By this method, the high antibody titer was observed in 3 wells.

(4) Cloning of Hybrid Cells

The cells in these wells were seeded to give 0.5 cell/well on a 96-well microtiter plate on which $10^4$ cells/well of mouse thymocytes had previously been seeded as vegetative cells, and cloned. As a result, 3 clonal mouse hybridoma, GAF 150-59, GAF 40-20 and GAF 13-3 cells, were obtained.

The cloned hybridoma were suspended in RPMI-1640 medium supplemented with 20% calf serum and 10% dimethyl sulfoxide (DMSO) and stored in liquid nitrogen.

EXAMPLE 4

(Immunoglobulin Class of Monoclonal Antibodies)

Antibodies produced by the hybridoma obtained in Example 3-(4) were tested by a subclass detecting kit (Bio RAD) to determine immunoglobulin subclass. Results are shown in Table 4.

TABLE 4

| Immunoglobulin subclass | Monoclonal antibody of the invention | | |
|---|---|---|---|
| | MoAb 150-59 | MoAb 40-20 | MoAb 13-3 |
| IgG1 | + | + | − |
| IgG2a | − | − | − |
| IgG2b | − | − | + |
| IgG3 | − | − | − |
| IgM | − | − | − |
| IgA | − | − | − |

In Table 4, "+" indicates the positive reaction, and "−" indicates the negative reaction.

The results shown in Table 4 revealed that both the antibodies produced by the GAF 150-59 and GAF 40-20 cells belong to IgG1, and that the antibody produced by the GAF 13-3 cell belongs to IgG2b.

EXAMPLE 5

(Purification of Monoclonal Antibodies)

For each of the hybridomas GAF 150-59, GAF 40-20 and GAF 13-3, $2\times10^6$ cells were inoculated into mice previously given intraperitoneally 0.5 ml of mineral oil. After 10 days, the ascites of 2 to 4 ml/mouse was collected. IgG was purified from the resulting ascites in the following manner. Namely, a 1:1 mixture of the ascites and a binding buffer solution (PBS) was loaded onto a protein G column equilibrated with the binding buffer solution to allow an antibody to be adsorbed thereby. After washing with the binding buffer solution, the antibody was eluted with an eluting buffer solution [0.1M glycine-hydrochloric acid (pH 2.7)]. 1M Tris (pH 8.0) was added to the eluate to neutralize it, followed by dialysis with phosphate buffered saline. Thus, desired anti-GAF antibodies 150-59, 40-20 and 13-3 were obtained, respectively.

REFERENCE EXAMPLE 2

(Screening for GAF-Neutralizing Antibody-Producing Cells)

Mouse BALB/c 3T3 A31 fibroblasts suspended in DMEM medium supplemented with 5% calf serum were seeded on a Nunc 96-well microtiter plate (flat-bottomed) at $2\times10^3$ cells in 75 μl of the medium per well, and cultured. The next day, 50 μl of the medium was discarded from each well, and 175 μl of serum-free DMEM medium was added. After culturing for 3 to 4 days, 20 μl of the medium was discarded from each well. Then, 20 μl of DMEM medium containing a hybridoma culture supernatant at various concentrations, 1 ng/ml 25-kDa GAF and 0.1% bovine serum albumin was added to each well, followed by culturing overnight. The next morning, 1 μCi of $^3$H thymidine (5 Ci/mmol, 0.5 mCi/ml, RCC Amersham) was added to each well, followed by further culturing for 5 to 7 hours. After culturing, each well was washed with 1 ml of PBS, and 100 μl of 5% SDS was added thereto. Then, the mixture was allowed to stand overnight at 37° C. Cell lysates in the respective wells were collected in a tube, and the amount of $^3$H thymidine taken into the cells was counted by a scintillation counter.

EXAMPLE 6

(GAF-Neutralizing Activity)

Figure 8:
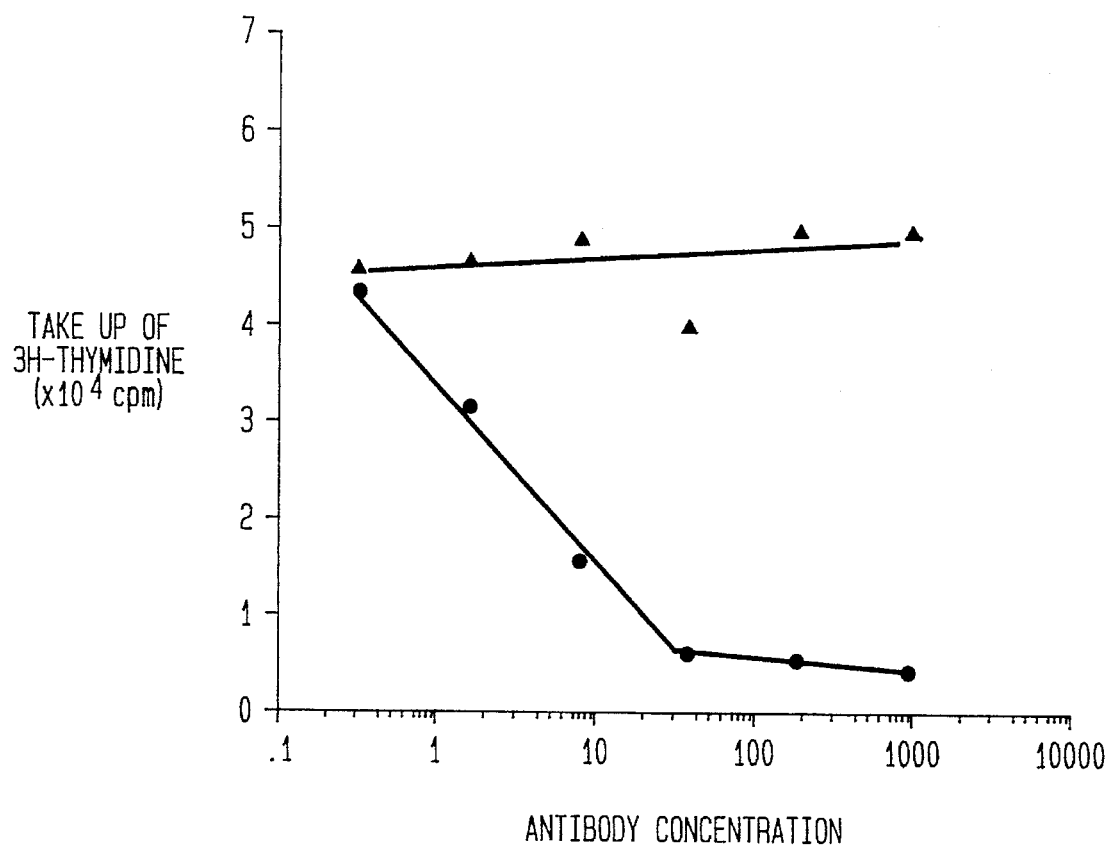
FIG. 8 is a graph showing neutralizing activity of MoAb 150-59 against GAF's growth promoting activity.

For antibody 150-59 purified in Example 5, human GAF-neutralizing activity was assayed by the method of Reference Example 2 (FIG. 8). The activity was assayed by the inhibition of proliferation of mouse BALB/c 3T3 A31 fibroblasts in the presence of 1 ng/ml of GAF N33. When MoAb 150-59 was added in an amount of 40 ng/ml, the uptake of $^3$H-thymidine was reduced to about one tenth that of the cells to which normal mouse IgG was added.

REFERENCE EXAMPLE 3

(Preparation of Horseradish Peroxidase-Labeled Antibody)

The purified anti-GAF antibody obtained in Example 5 was dialyzed against 0.1M phosphate buffer (pH 6.5) at 4° C. for 20 hours. Then, 0.6 mg of S-acetylmercaptosuccinic anhydride dissolved in 10 μl of N,N-dimethylformamide (DMF) was added, and reacted at 25° C. for 30 minutes. Then, 0.5M hydroxylamine, 5 mM EDTA and 0.2 ml of 0.1M Tris buffer were added, followed by reduction at 25° C. for 5 minutes. The reaction solution was placed on a Sephadex G-25 Fine column (1 cm in diameter×100 cm, Pharmacia Fine Chemical, Sweden), and eluted with 5 mM EDTA and 0.1M phosphate buffer (pH 6.0) to obtain an IgG fraction.

On the other side, 10 mg of horseradish peroxidase (Boehringer Mannheim, Germany) was dissolved in 1.5 ml of 0.1M phosphate buffer (pH 7.0), and 3.5 mg of N-(γ-maleimidobutyloxy)succinimide (GMBS) dissolved in 100 μl of DMF was added thereto, followed by stirring at 30° C. for 60 minutes. Then, the resulting solution was placed on a Sephadex G-25 Fine column (1.0 cm in diameter×100 cm), and eluted with 0.1M phosphate buffer (pH 7.0) to obtain maleimide group-introduced HRP (maleimidated HRP). IgG and maleimidated HRP were mixed with each other to a molar ratio of 1:1, and reacted at 4° C. for 20 hours. The reaction solution was loaded onto an Ultrogel AcA44 column, and eluted with 0.1M phosphate buffer (pH 7.0) to obtain an enzyme-labeled antibody (MoAb-HRP).

REFERENCE EXAMPLE 4

(Preparation of Antibody-Sensitized Plate)

The anti-GAF antibody obtained in Example 5 was diluted with 0.1M carbonate buffer (pH 9.6) to a concentration of 5 μg/ml. The resulting solution was poured in an amount of 100 μl/well into an immunoplate for EIA (Maxisoap: Nunc, Denmark), followed by standing overnight at 4° C. to sensitize the plate. The plate was washed with 0.01M phosphate buffer (pH 7.0) supplemented with 0.15 M NaCl, and then, 0.0.1M phosphate buffer 7.0) supplemented with 50% Block-Ace was poured into each well. The plate was stored in a chilled place until it is to be used.

REFERENCE EXAMPLE 5

(Assay of Human GAF)

(1) Preparation of Calibration Curve (a) Reagents

1. An enzyme-labeled antibody
2. An antibody-sensitized microtiter plate
3. Recombinant human GAF (GAF): 0–1 ng/ml
4. Buffer A (0.02M phosphate buffer (pH 7.0) supplemented with 0.15M NaCl)

Buffer B (0.02M phosphate buffer supplemented with 10% Block-Ace (a blocking agent prepared from lactoprotein, Dainippon Pharmaceutical) and 0.15M NaCl)

5. A peroxidase substrate solution (sodium citrate buffer (pH 5.5) supplemented with 0.02% hydrogen peroxide and 0.15% o-phenylenediamine)

An enzyme reaction-terminating solution (2N sulfuric acid)

(b) Assay

Into each well of the antibody-sensitized plate 100 µl of a solution of GAF in buffer B was poured, followed by reaction at 4° C. for 24 hours. Each well was washed with buffer A, and then, 100 µl of an enzyme-labeled antibody solution diluted 2000 times with buffer B was added thereto, followed by further reaction at 25° C. for 2 hours. Each well was washed with buffer A, and 100 µl of the peroxidase substrate solution was added thereto, followed by reaction 25° C. for 30 minutes. Then, 100 µl of the enzyme reaction-terminating solution was added. The absorbance at 492 nm was thereafter measured by using an automatic colorimeter for microtiter plates (Multiscan-Multisoft, Labosystems).

EXAMPLE 7

Using purified anti-GAF antibody 150-59 (5.6 mg/ml) obtained in Example 5, an HRP-labeled antibody was prepared according to the method described in Reference Example 3.

EXAMPLE 8

Using purified anti-GAF antibody 13-3 obtained in Example 5, an antibody-sensitized plate was prepared according to the method described in Reference Example 4.

EXAMPLE 9

Figure 9:
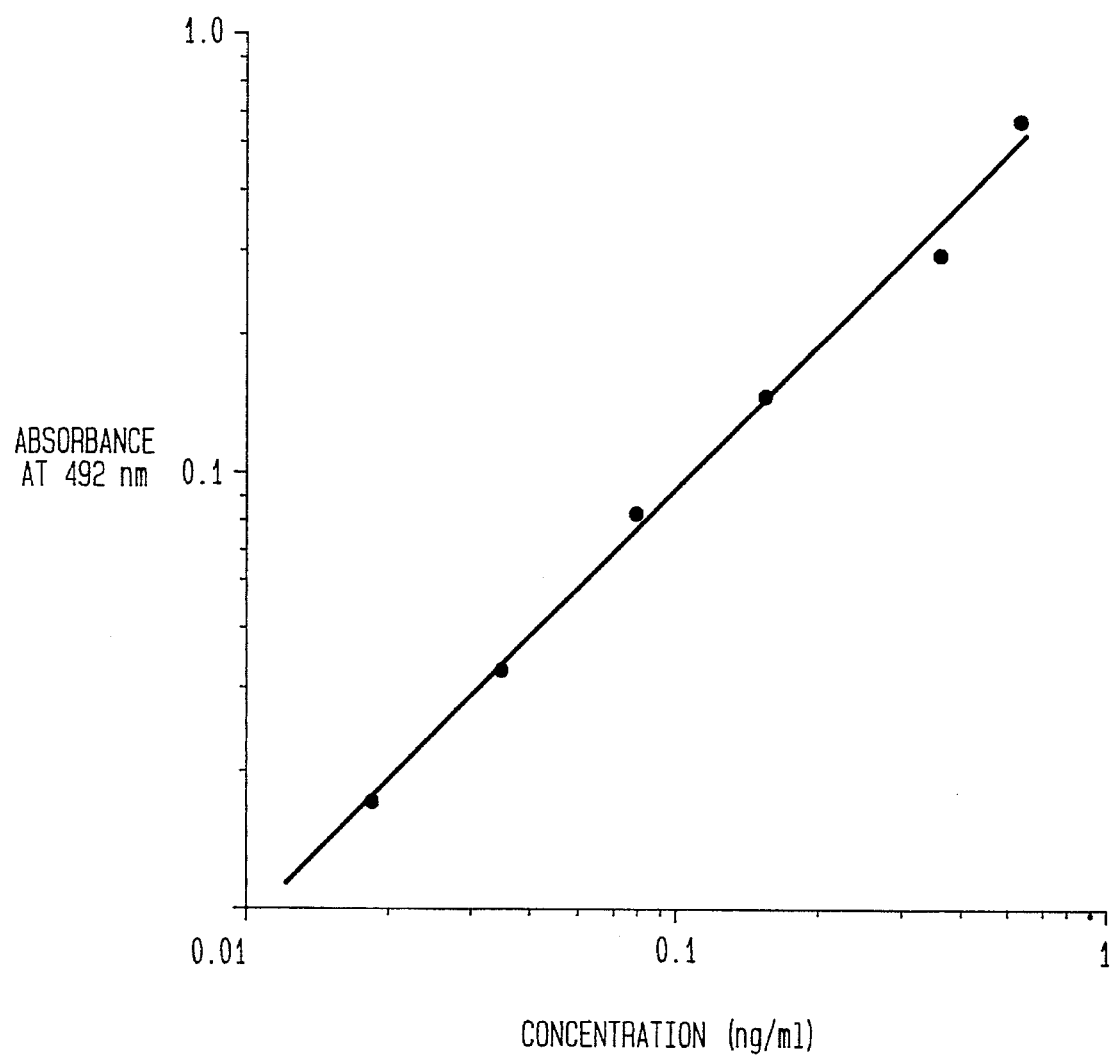
FIG. 9 is a graph showing a calibration curve of GAF prepared by a sandwich EIA method using MoAb 13-3 and MoAb 150-59.

Using the enzyme-labeled antibody obtained in Example 7 and the antibody-sensitized plate prepared in Example 8, GAF was assayed. Results thereof are shown in FIG. 9. Detection limit of this system was found to be 30pg/ml of

EXAMPLE 10

(Preparation of Polyclonal Antibody)

(1) Immunization

Rabbits (Kbs: JW; male, 14 weeks old) were injected subcutaneously with an oil emulsion (Freund's complete adjuvant; FcA) supplemented with heat-sterilized mycobacteria in which a solution of 1 mg of human GAF (N33) in phosphate buffered saline was emulsified. After 2 weeks, the rabbits were further injected subcutaneously with an oil emulsion (Freund's complete adjuvant; FIA) in which a solution of 1 mg of human GAF (N33) in phosphate buffered saline was emulsified, as additional immunization. The same procedure was repeated 3 times.

(2) Assay of Antibody Titer

Figure 10:
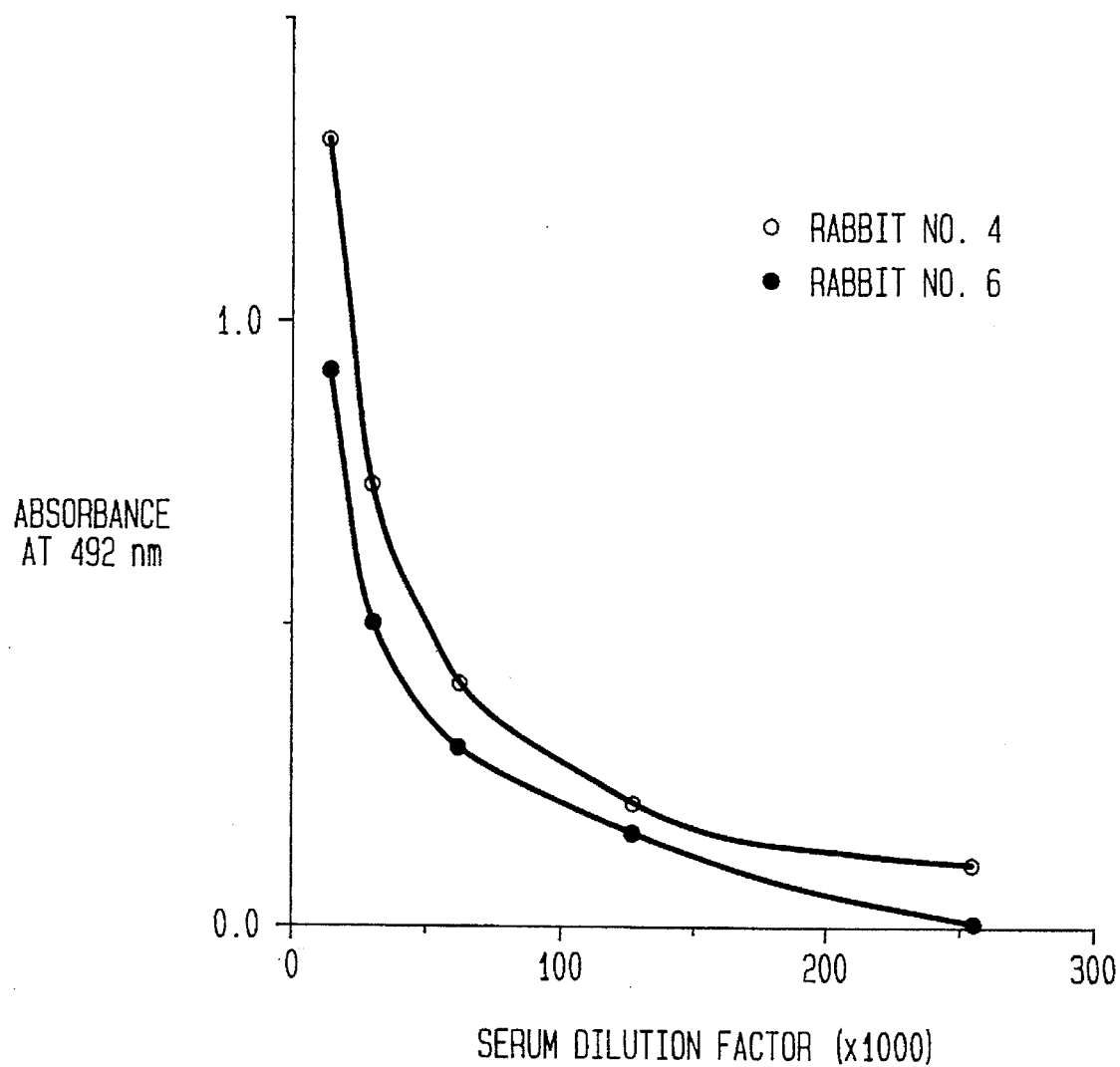
FIG. 10 is a graph showing the antibody titer of rabbit No. 4 and No. 6 sera obtained by immunization with GAF.

Two weeks after final immunization, the blood was collected and allowed to stand at room temperature for 1 hour. After additional standing at 4° C. for 6 hours, the blood was centrifuged to obtain the serum, which was diluted to each concentration. The solution was added in an amount of 100 µl/well to a 96-well polystyrene microtiter plate to which human GAF (N33) had previously been fixed, and incubated at room temperature for 2 hours. After removal of the resulting supernatant and washing, the HRP-labeled anti-rabbit IgG goat antibody (Kappel) was added as a secondary antibody, and incubated at room temperature for 2 hours. The secondary antibody was removed, and the wells were thoroughly washed, followed by addition of a substrate to conduct coloring reaction (EIA method). After 100 µl of the enzyme reaction-terminating solution was added to terminate reaction, the absorbance at 492 nm was measured by using an automatic colorimeter for microtiter plates (Multiscan-Multisoft, Labosystems). The relationship between the serum concentration and the absorbance is shown in FIG. 10.

(3) Purification of Antibody

A 1:1 mixture of the serum obtained in (2) described above and a binding buffer solution (PBS) was loaded onto a protein G column (NGK Insulators) equilibrated with the binding buffer solution to allow an antibody to be adsorbed thereby. After washing with the binding buffer solution, the antibody was eluted with an eluting buffer solution [0.1M glycine-hydrochloric acid (pH 2.7)]. 1M Tris buffer (pH 8.0) was added to the eluate to neutralize it, followed by dialysis with phosphate buffered saline.

EXAMPLE 11

(GAF-Neutralizing Activity)

Figure 11:
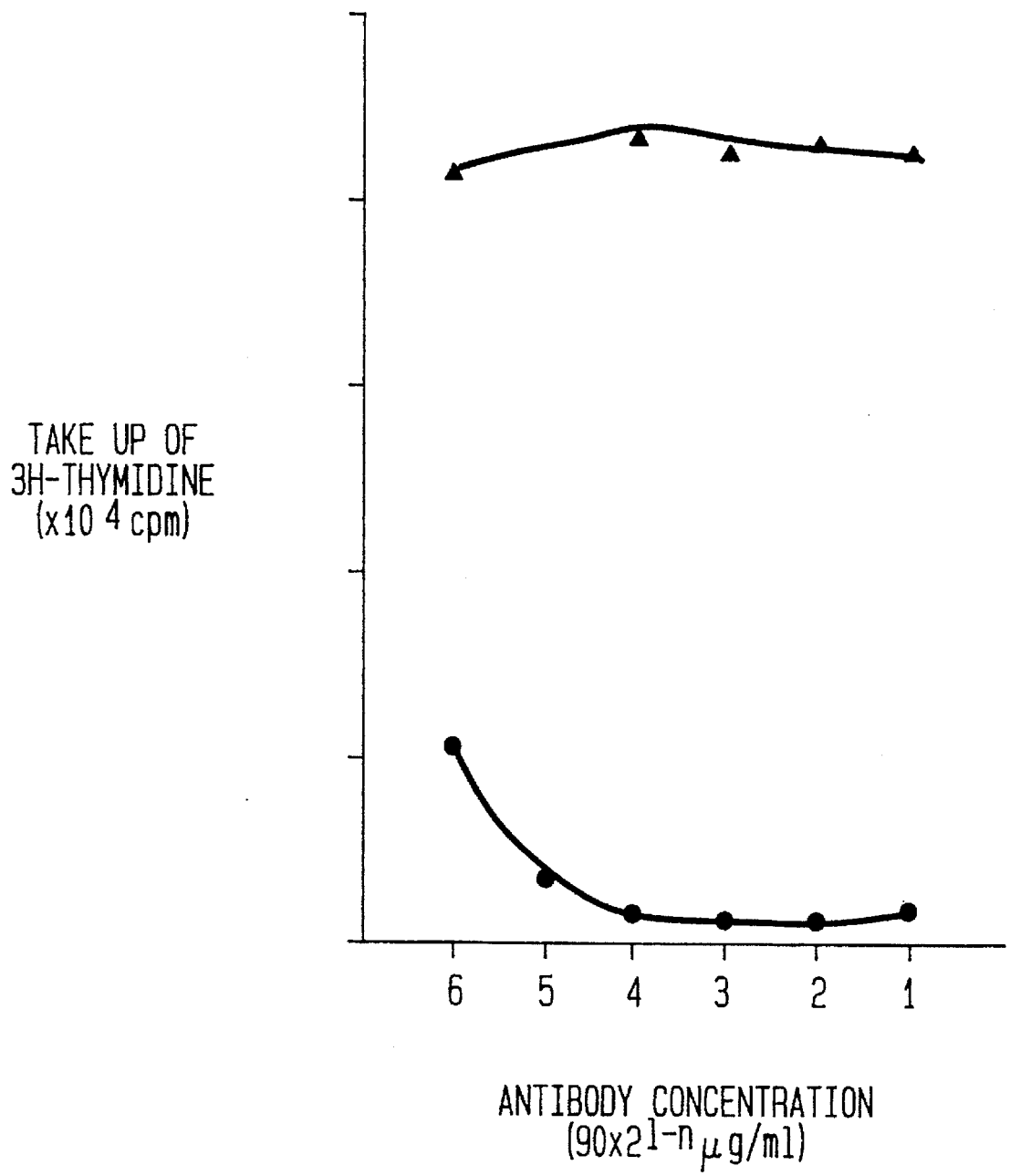
FIG. 11 is a graph showing neutralizing activity of rabbit anti-GAF No. 4 serum against GAF's cell growth promoting activity of GAF.

For anti-rabbit GAF IgG purified by the method of Example 10 (2), the GAF-neutralizing activity was examined by the method of Reference Example 2. Namely, the activity was assayed by the inhibition of proliferation of mouse BALB/c 3T3 A31 fibroblasts in the presence of 1 ng/ml of GAF (FIG. 11). Of the rabbit polyclonal antibodies, one antibody (No. 4 anti-GAF antibody) neutralized the GAF activity.

TEST EXAMPLE 1

(Comparison of GAF Activity)

GAF's cell growth promoting activity was assayed using rat glial cell strain RG-1 according to the following method. RG-1 cells (glial cell strain) suspended in DMEM medium supplemented with 10% fetal calf serum were seeded on a Nunc 96-well microtiter plate (flat-bottomed) at $3 \times 10^3$ cells in 100 µl of the medium per well, and cultured. After 2 to 3 days, 75 µl of the medium was discarded from each well, and 175 µl of serum-free DMEM medium was added to each well. After further culturing for 2 to 3 days, 20 µl of the medium was discarded from each well. Then, 20 µl of the sample diluted with DMEM medium supplemented with 0.1% bovine serum albumin was added to each well, followed by culturing overnight. The next morning, 1 µCi of tritium thymidine (5 Ci/mmol, 0.5 mCi/ml, RCC Amersham) was added to each well, followed by further culturing for 5 to 7 hours. After culturing, the medium of each well was discarded, and 100 µl of PBS supplemented with 0.5% trypsin and 0.01% EDTA was added to each well, followed by standing at 37° C. for 5 minutes. After the detachment of the RG-1 cells was confirmed under a microscope, the cells were collected on a glass fiber filter (Dainippon Pharmaceutical) by using a cell harvester (Flow Laboratories), and washed with water. Then, the amount of tritium thymidine taken into the cells was measured by a scintillation counter.

Figure 12:
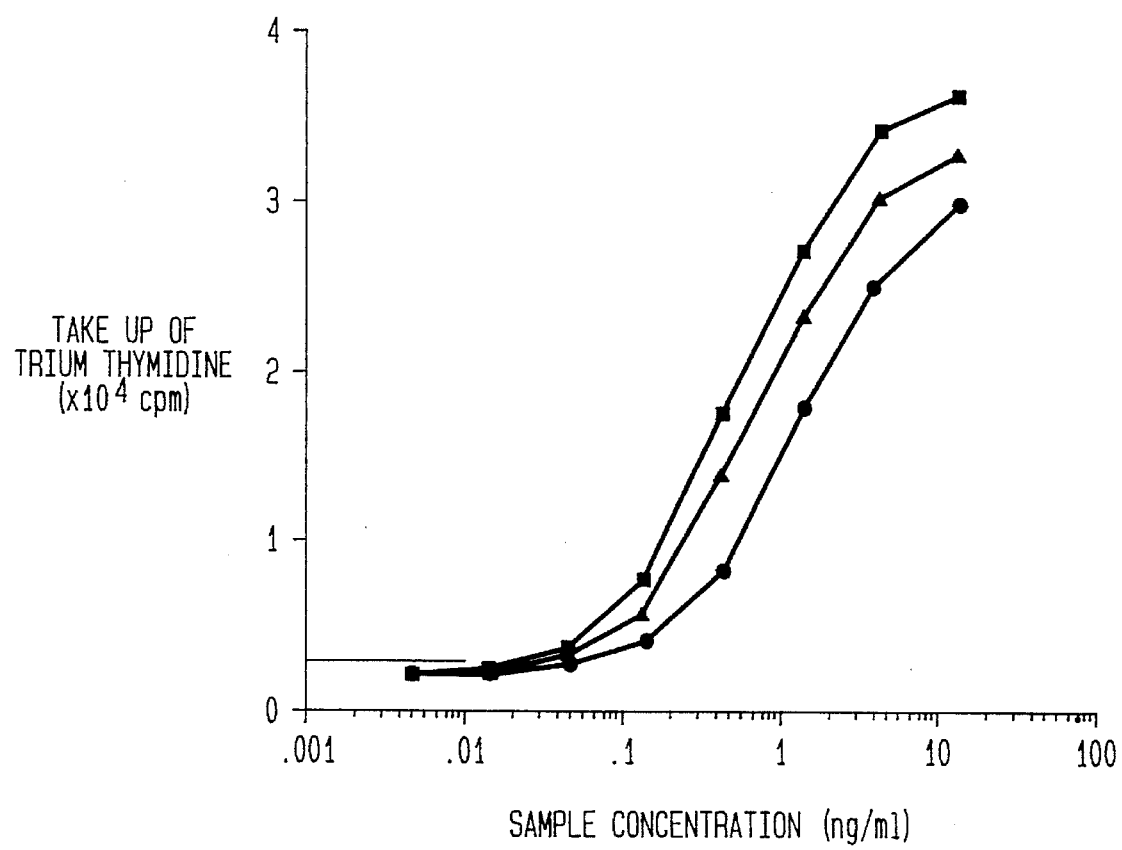
FIG. 12 is a graph showing growth promoting activity of N3, N33 and N49 upon a rat glial cell strain, wherein —●—, —▲— and —■— indicate N3, N33 and N49, respectively.

By this method, the growth promoting activity of the known N-terminal 3 amino acid-deleted GAF (N3, 30 kDa GAF) prepared in Example 1 according to Example 7 of EP 0503297, N33 and N49 upon glial cells was compared and shown in FIG. 12. As shown in FIG. 12, a molecule having a shorter N-terminal side chain length indicated a higher specific activity. N49 indicated a specific activity about 3 times higher than that of N3.

TEST EXAMPLE 2

(Study of GAF Polypeptide Stability)

(1) Stability to Acid Treatment

Each of the samples was dissolved in 50 mM Glysine-HCl (pH 2.5) and 0.1% CHAPS or in 50 mM Glysin-HCl (pH 2.5), 0.1% CHAPS and 20 µg/ml heparin to a final concentration of 200 ng/ml, and incubated at room temperature. Then, 50 µl samples were withdrawn with time, and each neutralized with 450 µl of 0.1% BSA-DMEM and 0.1HEPES (pH 7.2), followed by assay of the biological activity.

Figure 13:
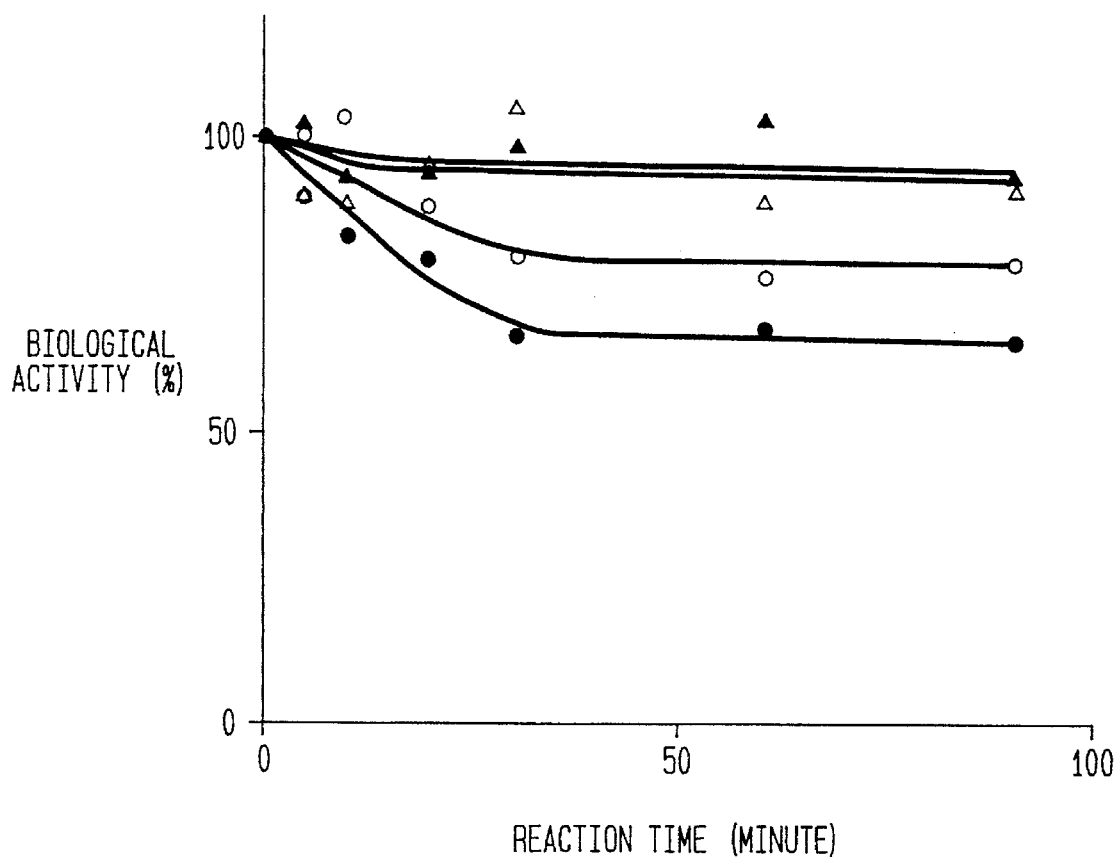
FIG. 13 is a graph showing acid stability of N3 and N33, wherein —●—, —○—, —▲— and —Δ— indicate N3, N33, the coexistence of 20 µg/ml heparin with N3 and the coexistence of 20 µg/ml heparin with N33, respectively.

Results thereof are shown in FIG. 13. The results revealed that both the N3 and N33 molecules were reduced activity by treatment at pH 2.5, but that N33 was more stable than N3 to acid treatment. The results further showed that the coexistence of heparin improved the stability to acid treatment for both the molecules.

(2) Stability to Heat Treatment

Each of the samples was dissolved in 10 mM Tris-HCl (pH 7.6) and 0.1% CHAPS or in 10 mM Tris-HCl (pH 7.6), 0.1% CHAPS and 20 µg/ml heparin to a final concentration of 200 ng/ml, and incubated at 56° C. or 42° C. Then, 50 µl samples were withdrawn with time, and each mixed with 450 µl of 0.1% BSA-DMEM The mixture was cooled to 0° C. followed by assay for the biological activity.

Figure 14:
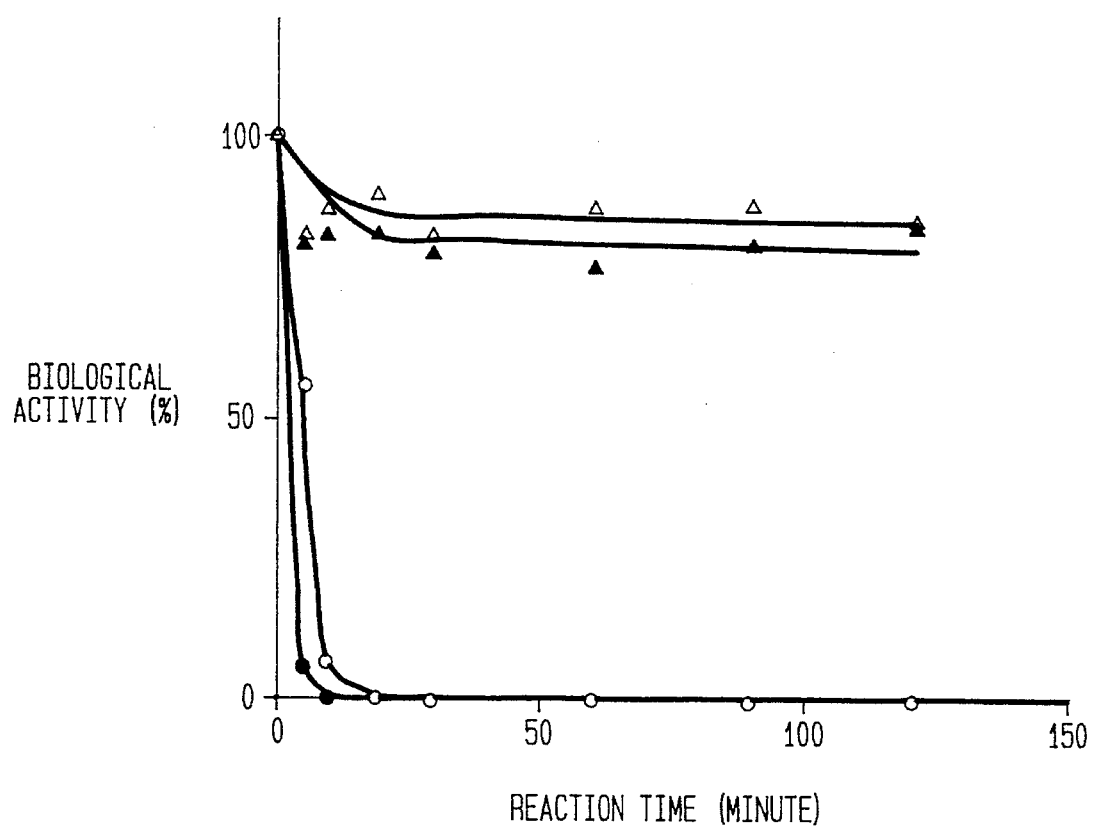
FIG. 14 is a graph showing stability to heat (treatment at 56° C.) of N3 and N33, wherein —●—, —○—, —▲— and —Δ— indicate N3 and N33, the coexistence of 20 µg/ml heparin with N3 and the coexistence of 20 µg/ml heparin with N33, respectively.
Figure 15:
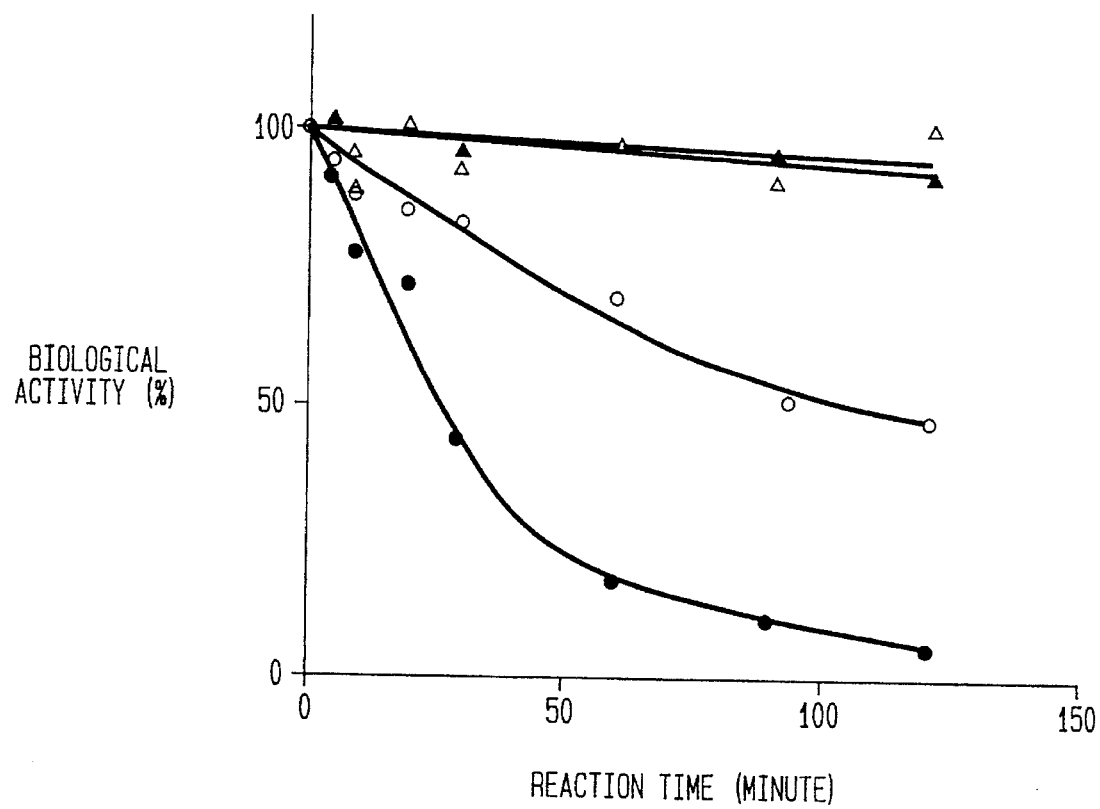
FIG. 15 is a graph showing stability to heat (treatment at 42° C.) of N3 and N33, wherein —●—, —○—, —▲— and —Δ— indicate N3, N33, the coexistence of 20 µg/ml heparin with N3 and the coexistence of 20 µg/ml heparin with N33, respectively.

Results of treatment at 56° C. and 42° C. are shown in FIGS. 14 and 15, respectively. Both the N3 and N33 molecules were rapidly inactivated by heat treatment at 56° C. The results clearly indicated that the inactivation rate in treatment at 42° C. was considerably slower than that in treatment at 56° C., and that N33 was more stable than N3. In either case, the coexistence of heparin prevents inactivation.

TEST EXAMPLE 3

(GAF's MK-CSF Activity)

Bone marrow cells collected from the femurs of BALB/c mice (female, 7 weeks old) were suspended in IMDM medium (Flow) supplemented with 10% fetal calf serum (FCS) at $2 \times 10^5$ cells/ml, and incubated on a plastic plate at 37° C. for 45 minutes. The non-adhesive bone marrow cells were collected and suspended ($1 \times 10^5$ cells/ml) in IMDM medium supplemented with Neutridoma-sp (Boehringer Mannheim), and inoculated with 200 µl/well into a 96-well flat-bottomed plate (Nunc).

At this time, the sample was added at various concentrations.

After culturing at 37° C. for 7 days, 50 µl of 5% glutaraldehyde (Wako Pure Chemical Industries) was added, and the plate was centrifuged at 2,000 rpm for 5 minutes to fix the cells. The plate was briefly washed with 0.1M phosphate buffer (pH 6.0), followed by acetylcholinesterase staining. Namely, 30 mg of acetylthiocholine iodide (Sigma) was dissolved in 45 ml of 0.1M phosphate buffer, and then, 6 ml of 30 mM copper sulfate, 3 ml of 0.1M sodium citrate and 6 ml of 5 mM potassium ferricyanide were added thereto to prepare a staining solution at the time of use. To each well 200 µl of the solution was added, and staining was carried out at room temperature for 6 hours. After washing with 0.1M phosphate buffer, the number of megakaryocytes was counted under a microscope. Results thereof are shown in FIG. 16.

Figure 16:
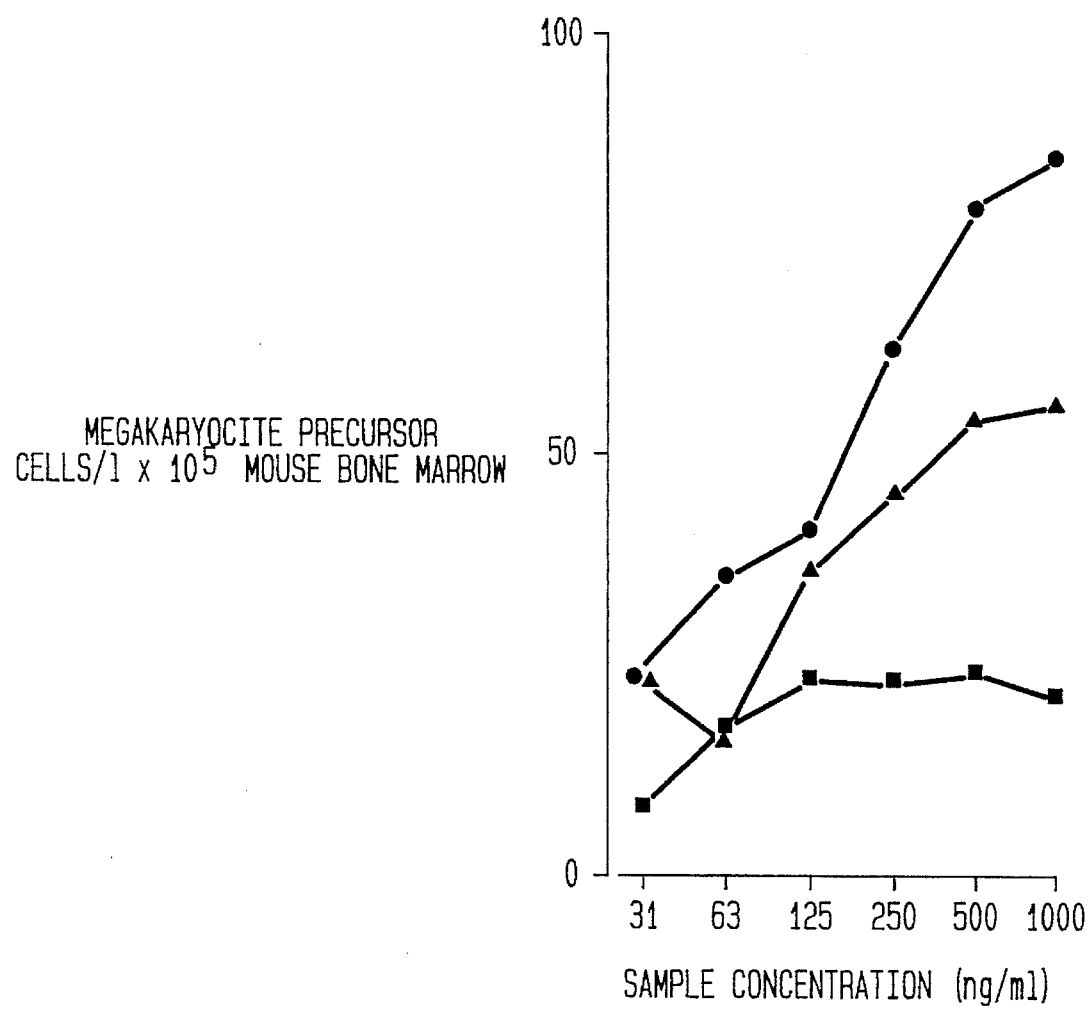
FIG. 16 is a graph showing MK-CSF activity of N3, N33 and N49, wherein —●—, —▲— and —■— indicate N3, N33 and N49, respectively.

As shown in FIG. 16, N3, N33 and N49 stimulated the proliferation of megakaryocyte precursor cells in the mouse bone marrow, in a dose dependent manner. Their activity was N3>N33>N49.

TEST EXAMPLE 4

(Increase of Peripheral Blood Platelets by Administration of GAF)

Each of N3, N33 and N49 was dissolved in physiological saline (Otsuka Pharmaceutical) supplemented with 100 µg/ml of bovine serum albumin (BSA, Armer) to yield a concentration of 500 µg/ml. The solution was given subcutaneously to BALB/c mice (female, 7 weeks old, Charles River) in a dose of 100 µl twice a day for 2 days. As a control, physiological saline supplemented with 100 µg/ml of BSA was given. The blood was collected at 4, 7, 9, 11, 14 and 17 days after initial dosing, and the number of platelets in the peripheral blood was counted by use of a multipurpose automatic hemocytometer (Toa Iyoh Denshi).

Figure 17:
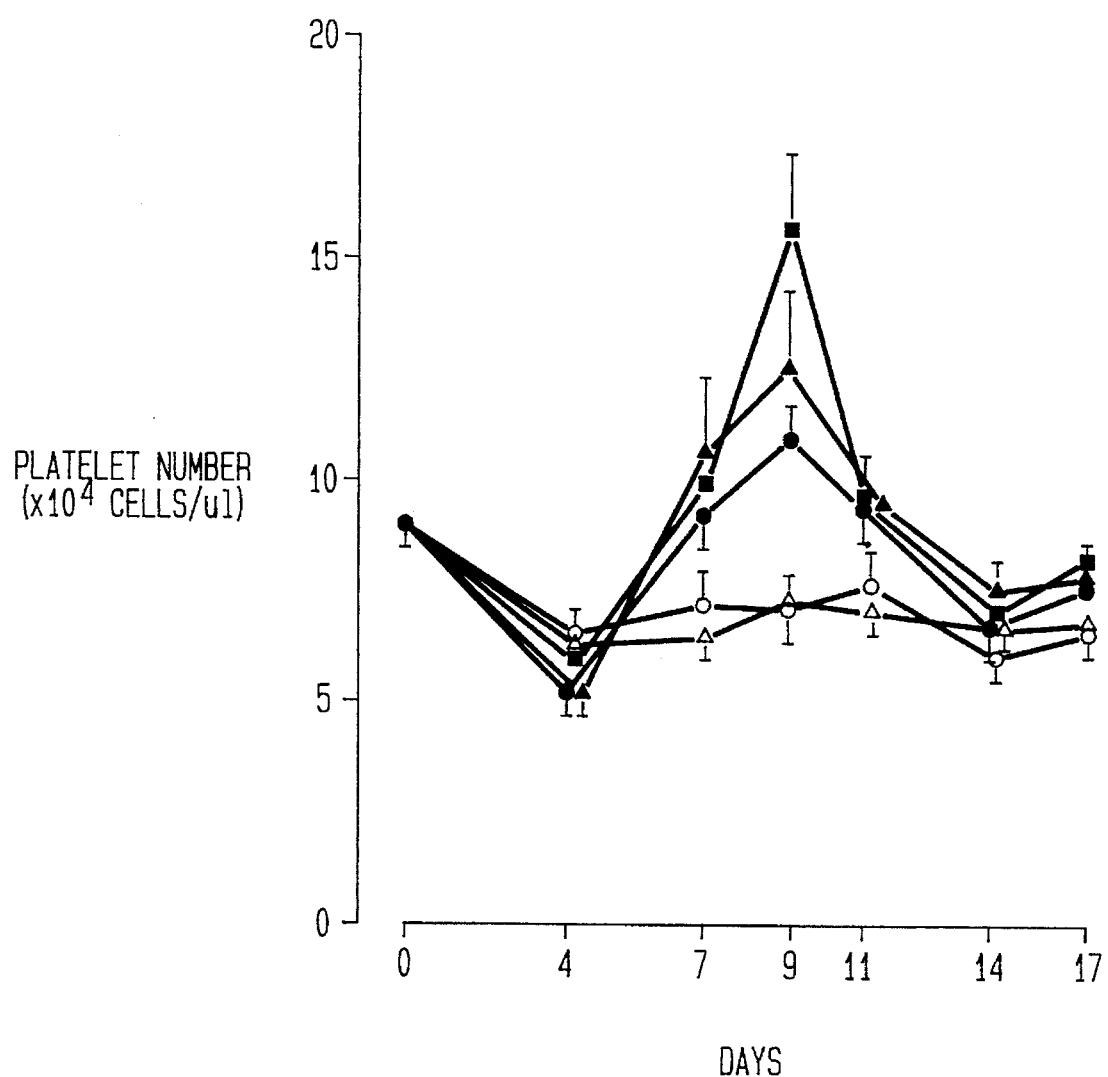
FIG. 17 is a graph showing the number of platelets in the peripheral blood by administration of N3, N33 and N49, wherein —●—, —▲—, —■—, —○— and —Δ— indicate N3, N33, N49, vehicle administration (control) and no treatment, respectively.

As a result, the groups given the GAF molecules exhibited clear increases in the number of platelets in the peripheral blood at 7 to 11 days after the initial dosing (FIG. 17). Their activity was N49>N33>N3, and the tendency of a molecule with a shorter N-terminal side chain length having a higher specific activity was observed.

TEST EXAMPLE 5

(Changes in Number of Platelets in Peripheral Blood by successive Administration of GAF N33 for two weeks)

N33 was dissolved in physiological saline (Otsuka Pharmaceutical) supplemented with 100 µg/ml of bovine serum albumin (BSA, Armer) to yield concentrations of 2, 10 and 500 µg/ml to prepare sample solutions. These solutions were given subcutaneously to BALB/c mice (female, 7 weeks old) in a dose of 100 µl twice a day for 14 days. As a control, physiological saline supplemented with 100 µg/ml of BSA was given. The blood was collected at 3, 5, 7, 10, 12, 14, 17 and 25 days after initial dosing, and the number of platelets in the peripheral blood was counted by use of a multipurpose automatic hemocytometer (Toa Iyoh Denshi).

Figure 18:
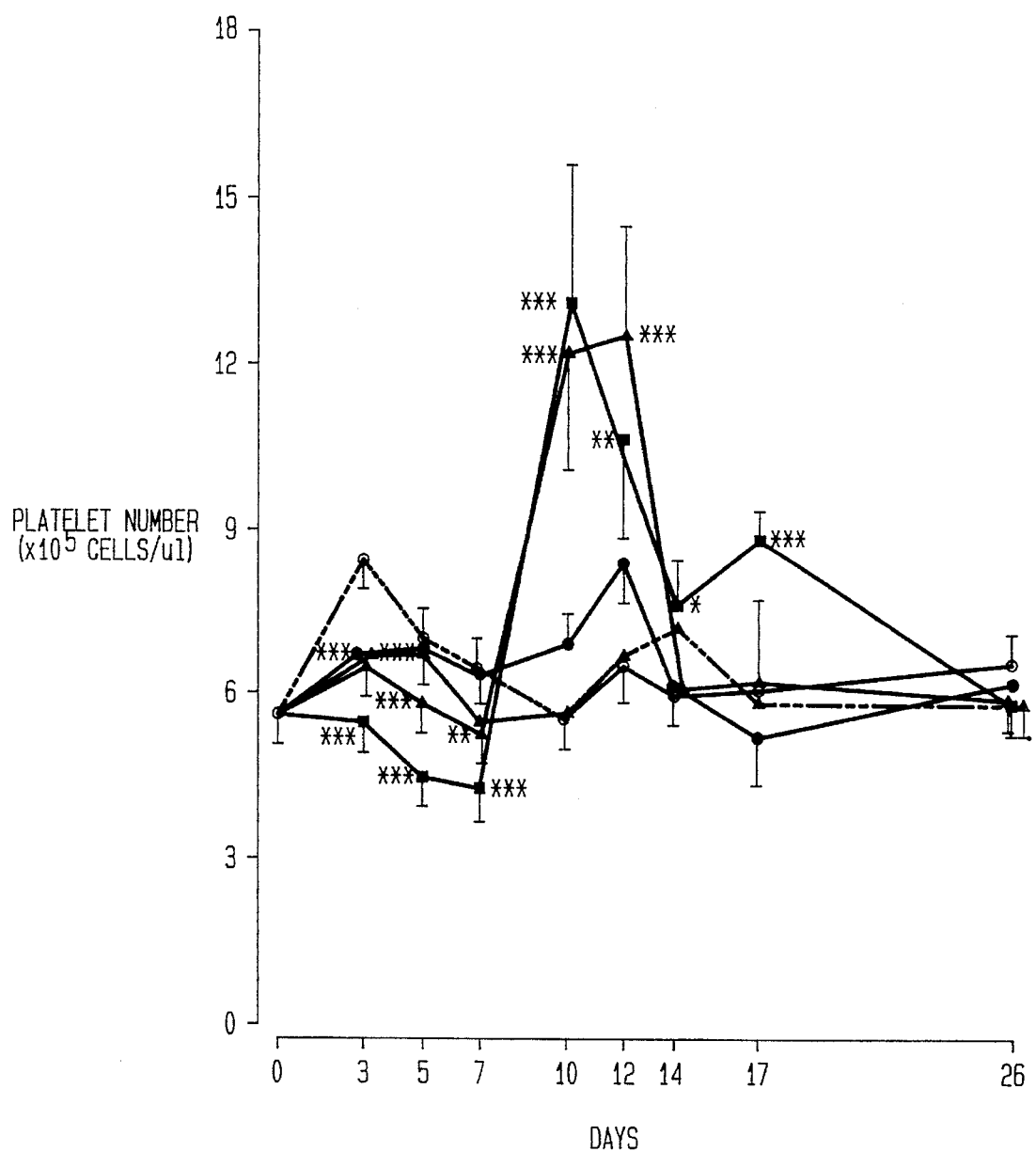
FIG. 18 is a graph showing the number of platelets in the peripheral blood by changes in the dosage of N33, wherein —■—, —▲—, —●—, —○— and —Δ— indicate 100 µg/day, 20 µg/day, 4 µg/day, vehicle administration (control) and no treatment, respectively, and *,  and * indicate $p<0.05$, $p<0.01$ and $p<0.001$, respectively.

Results thereof are shown in FIG. 18. All the sample solutions exhibited clear increases in the number of platelets in the peripheral blood at 10 to 12 days after the initial dosing. The number of platelets increased in a dose dependent manner.

TEST EXAMPLE 6

(Platelet-Increasing Activity of GAF N33 in Normal Mice)

GAF N33 prepared in Reference Example 1 was given intravenously or subcutaneously to CDF1 female mice having a body weight of about 20 g once a day successively for 5 days. The peripheral blood was collected for a predetermined period of time after termination of the administration, and the number of platelets was counted.

GAF N33 was dissolved in physiological saline supplemented with 1% normal mouse serum (Solution) to give a dosage of 0.2 ml/20 g of mouse (intravenous administration) or 0.1 ml/20 g of mouse (subcutaneous administration). The dosage of the drug was expressed in weight (μg) per mouse, and the date of measurement of the platelet number was expressed as the number of days after termination of the administration of GAF N33.

The number of platelets was counted by use of a multi-purpose automatic hemocytometer E-2500 (Symex, Toa Iyoh Denshi). Results thereof are shown in Table 5.

TABLE 5

| Dosage (μg/mouse/ day) | Root of administ- ration | Number of animals | Number of platelets ($\times 10^4/mm^3$) Average ± (standard deviation) | | |
|---|---|---|---|---|---|
| | | | 5 days | 7 days | 10 days |
| No dosing, control | | 5 | 62.09 (7.17) | 61.67 (10.11) | 70.20 (11.55) |
| Solution 0 | i.v. | 5 | 59.92 (10.76) | 62.44 (15.48) | 71.68 (9.22) |
| GAF N33 40 | i.v. | 5 | 87.50 (7.17) | 84.70 (9.02) | 79.80 (3.70) |
| Solution 0 | s.c. | 5 | 73.92 (7.65) | 57.20 (8.90) | 73.50 (7.09) |
| GAF N33 40 | s.c. | 5 | 87.36 (9.80) | 85.12 (7.82) | 85.82 (15.51) |

TEST EXAMPLE 7

(Platelet-Increasing Activity of GAF N33 in Tumor-Bearing Mice)

M5076 reticulosarcoma cells ($5\times10^5$ cells) were implanted in the abdominal endothelia of C57BL/6 female mice having a body weight of about 20 g, and GAF N33 was given subcutaneously to the mice once a day successively for 10 days from 5 days after implantation of the sarcoma cells. The peripheral blood was collected for a predetermined period of time after termination of the administration, and the number of platelets was counted.

GAF N33 was dissolved in physiological saline supplemented with 1% normal mouse serum (Solution) to give a dosage of 0.1 ml/20 g of mouse. The dosage of the drug was expressed in weight (μg) per mouse, and the date of measurement of the platelet number was expressed as the number of days after termination of the administration of GAF N33.

The number of platelets was counted by use of a multi-purpose automatic hemocytometer E-2500 (Symex, Toa Iyoh Denshi). Results are shown in Table 6.

TABLE 6

| Dosage (μg/mouse/ day) | Root of administ- ration | Number of animals | Number of platelets ($\times 10^4/mm^3$) Average ± (standard deviation) | | |
|---|---|---|---|---|---|
| | | | 2 days | 5 days | 7 days |
| No dosing, control | | 5 | 60.34 (6.85) | 62.72 (11.33) | 65.18 (14.81) |
| Solution (0) | s.c. | 5 | 63.98 (8.86) | 65.24 (18.56) | 79.88 (15.94) |
| GAF N33 (40) | s.c. | 5 | 103.74 (6.01) | 93.24 (20.10) | 100.66 (7.67) |

TEST EXAMPLE 8

(Platelet-Increasing Activity of GAF N33 After Giving an Antineoplastic Agent, Carboplatin (CBDCA) to Normal Mice)

CBDCA (Bristol Myers Squib) was given intravenously once to CDF1 female mice having a body weight of about 20 g in a dose of 100 mg/kg, and GAF N33 was given subcutaneously to the mice twice a day continuously for 7 days from 3 days after CBDCA administration. The peripheral blood was collected for a predetermined period of time after termination of the administration, and the number of platelets was counted.

GAF N33 was dissolved in physiological saline supplemented with 1% normal mouse serum (Solution) to give a dosage of 0.1 ml/20 g of mouse. The dosage of the drug was expressed in weight (μg) per mouse, and the date of measurement of the platelet number was expressed as the number of days after termination of the administration of GAF N33.

The number of platelets was counted by use of a multi-purpose automatic hemocytometer E-2500 (Symex, Toa Iyoh Denshi). Results thereof are shown in Table 7.

TABLE 7

| Dosage (μg/mouse/ day) | Root of administ- ration | Number of animals | Number of platelets ($\times 10^4/mm^3$) Average ± (standard deviation) | | |
|---|---|---|---|---|---|
| | | | 3 days | 5 days | 8 days |
| No dosing, control | | 5 | 62.88 (11.74) | 67.19 (8.17) | 56.16 (7.80) |
| CBDCA[1] + Solution 0 | s.c. | 5 | 32.00 (1.70) | 35.33 (14.51) | 47.84 (11.13) |
| CBDCA[1] + GAF N33 40[2] | s.c. | 5 | 96.40 (16.91) | 95.70 (9.39) | 79.60 (12.48) |

[1] 100 mg/kg (2 mg/20 g of mouse)
[2] GAF N33 was given in 2 divided doses of 20 μg.

TEST EXAMPLE 9

(Platelet-Increasing Activity of GAF N33 After an Antineoplastic Agent, Carboplatin (CBDCA), Was Given to Tumor-Bearing Mice to Decrease Platelets)

M5076 reticulosarcoma cells ($5\times10^5$ cells) were implanted in the abdominal endothelia of C57BL/6 female mice having a body weight of about 20 g. CBDCA was given intravenously to the mice at a dose of 100 mg/kg six days after implantation of the sarcoma cells, and GAF N33 was further given subcutaneously to the mice once a day successively for 7 days from 7 days after CBDCA administration. The peripheral blood was collected for a predetermined period of time after termination of the administration, and the number of platelets was counted.

GAF N33 was dissolved in physiological saline supplemented with 1% normal mouse serum (Solution) to give a dosage of 0.1 ml/20 g of mouse. The dosage of the drug was expressed in weight (μg) per mouse, and the date of measurement of the platelet number was expressed as the number of days after termination of the administration of GAF N33.

The number of platelets was counted by use of a multipurpose automatic hemocytometer E-2500 (Symex, Toa Iyoh Denshi). Results thereof are shown in Table 8.

TABLE 8

| Dosage (μg/mouse/day) | Root of administration | Number of animals | Number of platelets ($\times 10^4/mm^3$) Average ± (standard deviation) | | |
|---|---|---|---|---|---|
| | | | 1 days | 3 days | 5 days |
| No dosing, control | | 5 | 72.10 (8.44) | 70.98 (7.76) | 47.88 (16.08) |
| CBDCA[1) + Solution 0 | s.c. | 4 | 29.17 (11.16) | 39.55 (18.26) | 50.40 (7.34) |
| CBDCA[1) + GAF N33 20 | s.c. | 5 | 40.25 (21.43) | 59.15 (16.61) | 72.98 (4.02) |

[1)]100 mg/kg (2 mg/20 g of mouse)

EXAMPLE 12

(Preparation of Monoclonal Antibody (2))

Anti-GAF antibody-producing mouse hybridoma GAF 4-82 cells were obtained in a manner similar to that of Example 3. The antibody produced by the GAF 4-82 cells was examined with a mouse antibody subclass detection kit (Bio RAD). The results showed that the antibody belongs to the immunoglobulin class of IgM subclass.

EXAMPLE 13

(Purification of Monoclonal Antibody (2))

Anti-GAF antibody GAF 4-82 was obtained from hybridoma GAF 4-82 by the method described in Example 7.

TEST EXAMPLE 10

(Neutralization of GAF mediated Growth Megakaryocyte by Anti-GAF Antibody)

Bone marrow cells were collected from the femurs of BALB/c mice (female, 6 to 8 weeks old, Charles River), and suspended in Iscove's modification of Dulbecco's medium (IMDM, Flow) supplemented with 10% FCS to give $2\times10^6$ cells/mi. Then, the cells were incubated at 37° C. for 45 minutes in a plastic dish. Non-adherent cells ($1\times10^5$) from whose medium serum is removed by washing with IMDM medium were suspended in IMDM medium supplemented with Neutridoma-SP (Boehringer Mannheim), and 200 μl thereof is plated in each well of a 96-well flat-bottomed plate, together with 100 ng/ml of GAF N3 and each of antibodies diluted to various concentrations. After culturing at 37° C. for 7 days, 50 μl of 5% glutaraldehyde (Wako Pure Chemical Industries) was added thereto, followed by centrifugation at 2,000 rpm for 5 minutes to fix the cells. Then, the cells were washed with 0.1M phosphate buffer (pH 6.0), and stained. Thereafter, the number of positive cells was counted.

Figure 19:
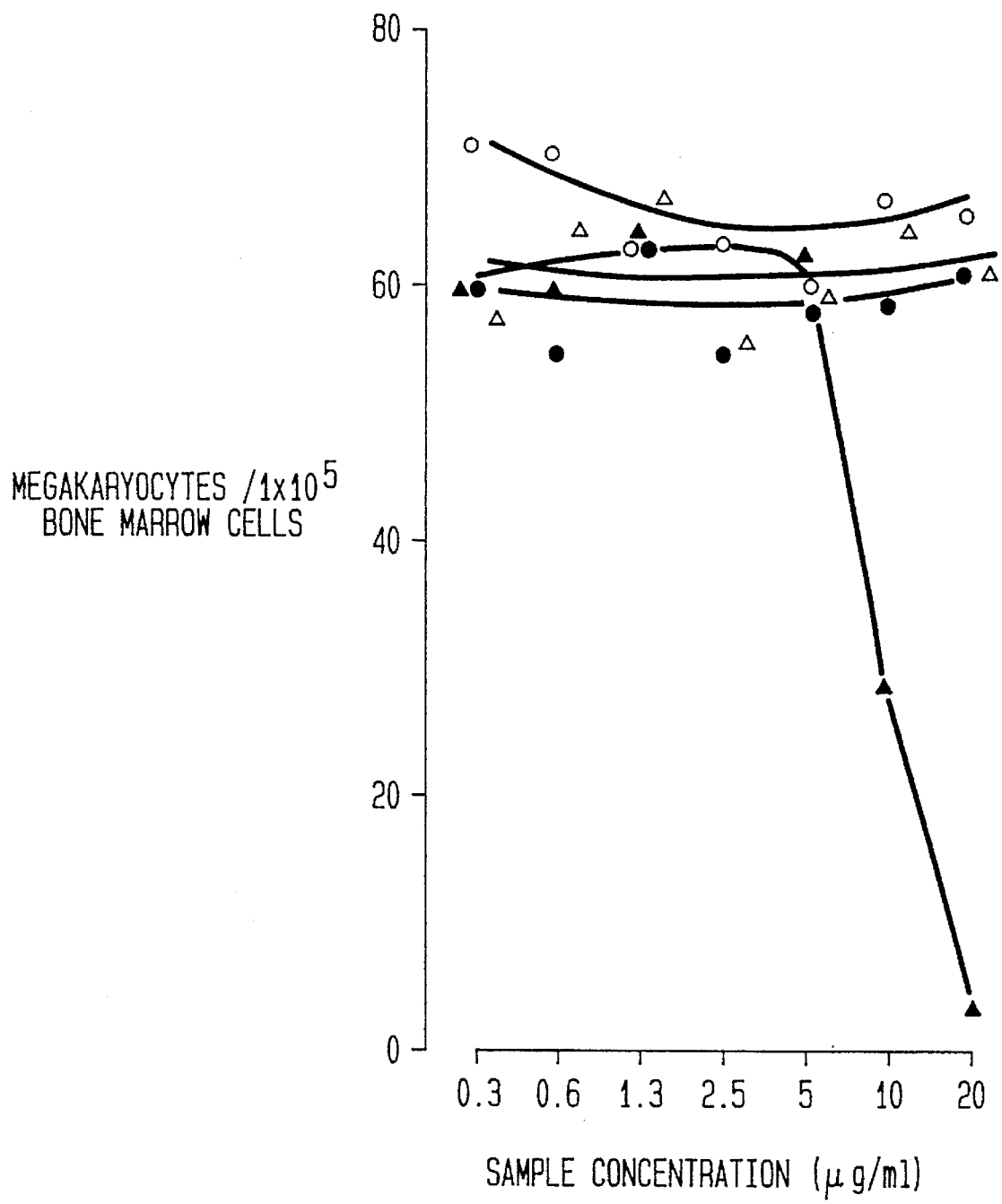
FIG. 19 is a graph showing inhibition of MK-CSF activity of GAF (N3) with anti-GAF monoclonal antibodies, wherein mouse non-adherent bone marrow cells (1×10⁵) were added together with GAF (N3) (100 μg/ml) and MoAb 150-59 (●), MoAb 4-82 (▲), MoAb 40-20 (Δ) or normal mouse IgG (o) of various concentrations.

MoAb 150-59 did not inhibit growth of megakaryocyte cells caused by GAF N3. In contrast, MoAb 4-82 inhibited the growth of megakaryocyte cells caused by GAF N3, depending on concentration, and completely neutralized the growth at 20 μg/ml (FIG. 19). The results proved that MoAb 4-82 had neutralization activity upon the growth of megakaryocyte cells caused by GAF N3. MoAb 40-20 did not affect the activity of GAF N3.

TEST EXAMPLE 11

(Neutralization of Platelet-Increasing Activity of GAF N33 of Anti-GAF Monoclonal Antibody)

BALB/c mice (female, 7 weeks old, 6 mice/group) were subcutaneously given a mixture of GAF N33 (50 μg) diluted with physiological saline (Otsuka Pharmaceutical) supplemented with 100 μg/ml bovine serum albumin (BSA, Armer) and a 20-fold excess amount (1 mg) (against GAF N3) of MoAb 150-59, MoAb 4-82 or MoAb 40-20 twice a day for 2 days. As a positive control, only GAF N33 was given. As a negative control, physiological saline supplemented with 100 μg/ml BSA was given. After dosing, the blood was collected from the ocular fundus veins with time, and the blood examination was conducted with a multipurpose automatic hemocytometer (Toa Iyoh Denshi). The Dunnett's multiple comparative test was carried out.

Figure 20:
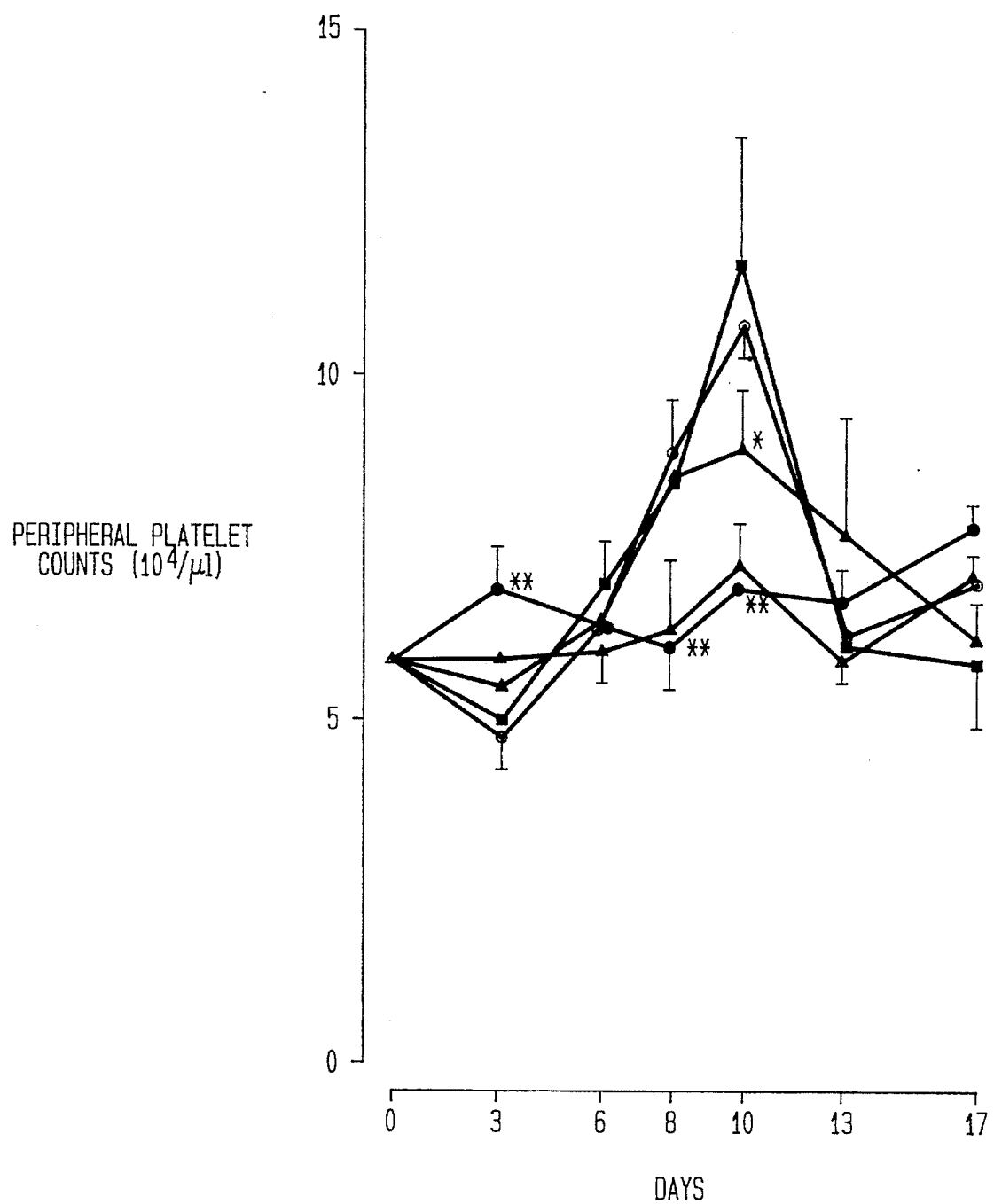
FIG. 20 is a graph showing inhibition of platelet-increasing activity of GAF (N33) with anti-GAF monoclonal antibodies, wherein 1 mg of MoAb 150-59 (●), MoAb 4-82 (▲) or MoAb 40-20 (■) was subcutaneously given together with 50 μg of GAF N33 twice a day for 2 days. As a positive control, only GAF N33 was given (o). As a negative control, physiological saline supplemented with 100 μg/ml BSA was given (Δ).

The number of platelets in the peripheral blood was increased by the administration of GAF N33, and showed a peak 10 days after dosing. MoAb 150-59 completely neutralized the platelet-producing promoting activity of GAF N33 at a 20-fold excess amount of GAF N33, and the mice given GAF N33 and MoAb 150-59 showed the number of platelets on the same level with the negative control group to which physiological saline was given (significant with $p<0.01$ to the group to which GAF N33 was given). Further, MoAb 4-82 partly neutralized the activity of GAF N33 (significant with $p<0.05$ to the group to which GAF N33 was given). MoAb 40-20 did not affected the platelet-producing promoting activity of GAF N33 (FIG. 20).

TEST EXAMPLE 12

(Growth Promoting Activity of GAF N33 upon Juvenile Rat Hepatic Cells)

The livers of SD rats (female, 6 days old, Nippon Clea) were collagenase digested by the in situ perfusion method [*Jikken Igaku* (*Experimental Medicine*) 6, 1105 (1988)] to separate hepatocytes. The cells were washed with WE medium (Flow), and then, suspended in WE medium supplemented with $10^{-9}$M insulin (Sigma), $10^{-9}$M dexamethasone (Sigma) and 5% fetal calf serum (FCS, Whittaker M. A. Bioproducts) so as to give $2.5\times10^5$ cells/mi. $2.5\times10^4$ cells were plated in each well of a 96-well microplate (Nunc) coated with a 0.03% collagen solution [Cellugen 1-AC (Kohken) was diluted with 0.02N acetic acid] beforehand, and the cells were cultured at 37° C. for 6 hours. The medium was replaced by a new medium, and culturing was conducted at 37° C. overnight, followed by addition of recombinant human epidermal growth factor (rhEGF-)(Wakunaga Pharmaceutical Co.) or GAF N33 of various concentrations and further culturing for 2 days. Then, a 5 mg/ml MTT-PBS solution was added in an amount of 20 µl/well. After culturing at 37° C. for 4 hours, a 10% SDS-0.01N HCl solution was added in an amount of 100 µl, followed by further incubation at 37° C. overnight. Then, the absorbance at 590 nm was measured with a Titertek multi-scan (Flow). The results are shown in FIG. 21. As shown in FIG. 21, GAF N33 showed the activity of proliferating juvenile rat hepatic cells, though it was weaker than rhEGF.

TEST EXAMPLE 13

(Mouse Liver Weight-Increasing Action of GAF N33)

BALB/c mice (female., 7 weeks old, n=6, Nippon Kurea) were subcutaneously given 100 µl of a 20 µg/ml, 100 µg/ml or 500 µg/ml solution of GAF N33 diluted with physiological saline (Otsuka Pharmaceutical) supplemented with 100 µg/ml bovine serum albumin (BSA, Sigma) twice a day for 10 days, according to the following group constitution. The control group was given physiological saline supplemented with 100 µg/ml BSA. The day after the final dosing, the mice were anatomized to measure the weight of the livers. The significant difference test between the groups was carried out using the Dunnett's multiple comparative test.

Group constitution

1. Control
2. GAF N33 (4 µg/mouse/day)
3. GAF N33 (20 µg/mouse/day)
4. GAF N33 (100 µg/mouse/day)

Results thereof are shown in Table 9. The results shown in Table 9 revealed that the weight of the livers significantly increased depending on the amount of GAF N33 given. According to the autopsy, the significant difference was not observed between liver sections increased in weight by dosing of GAF N33 and sections of the group to which no GAF N33 was given, and therefore the cause of an increase in the weight of the livers was considered to be increases in hepatic parenchymal cells and interstitial cells.

TABLE 9

| Mouse Liver Weight-Increasing Action of GAF N33 | | |
|---|---|---|
| Group | n | Liver (g) |
| Control | 6 | 1.0 ± 0.07 |
| GAF (4 µg) | 6 | 1.17 ± 0.08* |
| GAF (20 µg) | 6 | 1.18 ± 0.13** |
| GAF (100 µg) | 6 | 1.32 ± 0.07** |

Mean ± SD. *, **: Significantly different from the control group (Dunnett's, test, *: p < 0.05, **: p < 0.01)

TEST EXAMPLE 14

(Liver Weight-Increasing Action of GAF N3, N33 and N49)

BALB/c mice (female, 7 weeks old, n=6, Charles River) were subcutaneously given 100 µl of a 500 µg/ml solution of GAF N3, N33 or N49 diluted with physiological saline supplemented with 100 µg/ml BSA twice a day for 6 days. The control group was given physiological saline supple- mented with 100 µg/ml BSA. At 10 days after dosing, the mice were anatomized to measure the weight of the livers. The significant difference test between the groups was carried out using the Dunnett's multiple comparative test. Results thereof revealed that the weight of the livers was significantly increased by all GAF polypeptides treatment (p<0.01). The tendency was observed that a polypeptide having a longer chain resulted in a more increase in the weight of the livers (FIG. 22).

EXAMPLE 14

(Transformation of Mouse BALB/c 3T3 Cells with GAF cDNA)

(A) Construction of Plasmid

Plasmid pGAF1 [M. Miyamoto et al., *Mol. Cell. Biol.*, 13, 4251 (1993)] was cleaved with restriction enzyme BamHI and a 1.55-kb entire coding region for GAF was isolated. On the other hand, vector pTB399 [R. Sasada et al., *Cell Struct. Funct.*, 12, 1205 (1987)] was cleaved with restriction enzyme BamHI to remove the IL-2 cDNA region, followed by insertion of the above-mentioned 1.55-kb fragment of GAF cDNA, thereby constructing expression plasmid pRGB12 possible to express human GAF with an animal cell under the control of the Abelson murine leukemia virus (MuLV)-LTR promoter (FIG. 23).

(B) cDNA transfection and isolation of Transformants

Mouse BALB/c 3T3 clone A31-1-1 cells [A31 cells, T. Kakunaga et al., *Science*, 209, 505 (1980)] were cultured in Dulbecco's modified Eagle's medium (DMEM, Flow) supplemented with 10% calf serum (CS, Flow). The A31 cells ($1 \times 10^5$ cells) were plated in a 60-mm tissue culture dish (Falcon). The next day, 10 µg of expression vector pRGB12 was transfected by the calcium phosphate coprecipitation method [M. Wigler et al., *Cell*, 16, 777 (1979)]. The cells transfected were cultured in DMEM medium supplemented with 5% calf serum (CS, Flow) for 4 weeks, and transformants were selected by the focus forming method. Then, five clones of ATG1, ATG2, ATG3, ATG4 and ATG5 were cloned by the limiting dilution method.

These cells showed a remarkable morphological change, compared with parent strain A31. That is, the A31 cells were flat, proliferated to form a regular cobble stone-like layer, and showed significant contact inhibition. On the other hand, the resulting clones were three-dimensional spindle-shaped, proliferated in multiple layers overlapping one another, and showed a malignant cell-like form.

(C) Properties of Transformants $2.5 \times 10^4$ cells of each transformant or the parent strain (A31 cell) were plated in a 35-mm tissue culture flask and cultured in 2 ml of DMEM medium supplemented with 5% CS, changing the medium every 2 to 3 days. The number of cells was counted with a Coulter counter, and the saturation density and the growth rate were calculated. Results thereof are shown in FIG. 24 and Table 6.

These transformants were high in growth rate, compared with the parent strain (A31 cell). Further, the A31 cells formed a cell layer after 4 to 5 days and stop proliferating, whereas theses transformants continued to proliferate for 7 to 9 days, while forming multiple layers overlapping one another, resulting in a saturation density of 5 to 8 times higher than that of the A31 cells.

(d) GAF productivity of transformant $1 \times 10^5$ cells of each transformant or the parent strain (A31 cell) were plated in a 35-mm tissue culture dish and cultured in 2 ml of DMEM medium supplemented with 5% CS for 3 days. The culture supernatant and cell extract were collected to assay GAF activity. The cells were scraped from the dish with a cell scraper, and washed with PBS, followed by suspension of the cells in 1 ml of PBS. The suspension was subjected to ultrasonic treatment (90 seconds) under ice cooling, and centrifuged at 15000 rpm for 20 minutes to obtain a supernatant. This supernatant was used as the cell extract.

As shown in Table 10, the GAF activity was detected in the culture supernatant of each transformant, whereas the GAF activity was scarcely detected in the cell extract. The correlation was observed between the growth rate of the transformant and the production amount of GAF.

TABLE 10

| Cell | Morpho-logical Change | GAF content (ng/dish) | | Saturation Density ($10^5$ cells/ $cm^2$) | Doubling Time (hr) |
|---|---|---|---|---|---|
| | | Medium | Cell Extract | | |
| A31 | — | 0.03 | 0.03 | 0.32 | 24.0 |
| ATG1 | + | 1.8 | 0.03 | 1.5 | 21.5 |
| ATG2 | + | 7.8 | 0.06 | 2.2 | 20.5 |
| ATG3 | + | 60 | 0.6 | 2.5 | 15.5 |
| ATG4 | + | 19 | 0.5 | 1.8 | 19.0 |
| ATG5 | + | 78 | 0.35 | 1.4 | 17.0 |

EXAMPLE 15

(Reversion of Transform Character of Transformants with Antibody)

The transformants secreted GAF extracellularly, so that they were considered to express the transform phenotype by the autocrine fashion.

It was therefore studied whether or not their character was inhibited by addition of an antibody for neutralizing the GAF activity. When the transformants were cultured in the presence of MoAb 150-59, the shape of cells returned to a parent strain A31-like, the growth rate was reduced, and the saturation density was decreased (FIG. 25). In the presence of normal mouse IgG, the transformants showed no change. The GAF activity in the culture supernatants of the transformants was not detected at all, when MoAb 150-59 was added.

These results proved that MoAb 150-59 showed suppressive activity upon tumor cells cancerated by the autocrine mechanism made by abnormal production of GAF.

EXAMPLE 16

(Anchorage Independent Growth of Transformants and Effect of Antibodies)

Acquisition of anchorage independent growth ability is considered to be on in vitro property which is most related to cell canceration. Then, for the resulting transformants, growth in soft agar medium was studied. Two milliliters of DMEM medium supplemented with 0.5% Bacto-Agar (Difco) and 10% FCS was poured in each 35-mm tissue culture dish beforehand. The cells were removed with trypsin, and suspended in a medium supplemented with 0.3% Bacto-Agar and 10% FCS to give $1 \times 10^4$ cells/ml. One milliliter of the suspension was layered on each medium described above. For examining the action of antibodies, 10 μg/ml rabbit anti-GAF antibody or MoAb 150-59 was added to the suspension. After culturing at 37° C. for 2 weeks, colonies comprising viable cells were stained with iodonitrotetrazolium, and counted [A. Rosenthal, et al., *Cell*, 46, 301 (1986)].

Results thereof are shown in Table 11. The parent strain (A31 cell) could hardly form a colony, whereas the transformants formed many colonies. It was observed that the ATG3 and ATG5 cells which produced GAF in large amounts had a tendency to form large colonies. However, no correlation was observed between the production amount of GAF and the colony forming frequency. It was considered that anchorage independent growth took place with GAF produced by the transformants, because colony formation of the transformants was inhibited with the rabbit anti-GAF neutralizing antibody. IgG of normal animals did not affect colony formation of the transformants (the data are not shown). On the contrary, MoAb 150-59 inhibited colony formation of the ATG1 cells, but could not inhibit colony formation of the other transformants.

TABLE 11

Anchorage Independent Growth of Transformants and Action of Anti-GAF Antibody

Experiment 1

| Cell | No. of Colony | No. of Colonies in the Presence of Rabbit Anti-GAF Antibody |
|---|---|---|
| A31 | 12 | 2 |
| ATG1 | 652 | 100 |
| ATG2 | 1181 | 166 |
| ATG3 | 526 | 106 |
| ATG4 | 800 | 211 |
| ATG5 | 567 | 124 |

Experiment 2

| Cell | No. of Colony | No. of Colonies in the Presence of MoAb 150-59 |
|---|---|---|
| A31 | 5 | 8 |
| ATG1 | 803 | 277 |
| ATG2 | 1182 | 1385 |
| ATG3 | 1312 | 1386 |
| ATG4 | 681 | 541 |
| ATG5 | 1519 | 1592 |

DMEM containing 10% FCS and 0.5% agar was added to a 35-mm tissue culture dish beforehand. Cells ($1 \times 10^4$) were suspended in DMEM containing 10% FCS and 0.5% agar, and plated. The rabbit anti-GAF antibody (100 μg/ml) or MoAb 150-59 (10 μg/ml) was added. These were cultured for 2 weeks and viable colonies were counted. Colony formation was not affected by the added IgG fraction prepared from a preimmune animal. The colonies formed in the presence of the anti-GAF antibody were smaller than those formed in the absence of the anti-GAF antibody.

EXAMPLE 17

(Tumor Forming Ability of Transformants in Nude Mice and Inhibition with Antibody)

(A) Tumorigenecity of Transformants

In order to study the in vivo tumor forming activity of the transformants, nude mice were inoculated with the ATG3 or ATG5 cells, and examined whether or not a tumor was formed.

Nude mice (female, 7 weeks old, 5 mice/group, Charles River) were subcutaneously inoculated with the ATG3, ATG5 or A31 cells ($3 \times 10^6$ cells) cultured in vitro, and the size of tumors formed after 14 days was measured. The volume of a tumor was calculated as (the width of a tumor)$^2 \times$(the length of a tumor)/2.

As shown in Table 12, both the ATG3 cells and the ATG5 cells were taken to the nude mice to form tumors. The parent strain, the A31 cells, formed no tumor.

TABLE 12

Tumorigenecity of Transformants ATG3 and ATG5 in Nude Mice

| Cell | Population Size | Tumor Size mean ± SD (mm$^3$) |
|---|---|---|
| A31 | 5 | 0 |
| ATG3 | 6 | 4280 ± 1212 |
| ATG5 | 6 | 2203 ± 1332 |
| None | 5 | (−) |

(B) Anti-Tumor Action of Antibody

Nude mice (female, 7 weeks old, 5 mice/group, Charles River) were subcutaneously inoculated with the ATG5 cells (1.5×10$^6$ cells) cultured in vitro, and given MoAb 150-59, MoAb 40-20 or normal mouse IgG (i.v., doses of 200 μg/mouse/day), from 3 days after inoculation for 5 days. Then, the volume of tumors was measured with time.

Tumor formation was clearly inhibited by administration of MoAb 150-59 which shows neutralization activity upon GAF in vitro (FIG. 26). In contrast, MoAb 40-20 recognizing GAF, but having no neutralization activity, or normal mouse IgG did not affect tumor formation.

It was further examined whether a tumor degenerate or not by administration of an antibody after the transformant had been taken and the tumor had been formed.

Nude mice (female, 7 weeks old, 5 mice/group, Charles River) were subcutaneously inoculated with the ATG5 cells (1.5×10$^6$ cells), and given i.v. doses of 200 μg/mouse/day of normal mouse IgG, MoAb 40-20 or MoAb 150-59, from 11 days after the tumor size had reached 1000 mm$^3$ for 5 days Then, the tumor size was measured with time. The volume of a tumor was calculated as (the width of a tumor)$^2$×(the length of a tumor)/2. Results of this therapeutic experiment are shown in FIG. 27. The tumor degenerated by administration of MoAb 150-59, resulting a cure. In observation up to 20 days after administration of the antibody, tumor formation was not observed.

EXAMPLE 18

(Anti-Tumor Action of MoAb 150-59 upon Human Tumor)

For in vitro culture supernatants of various cell strains derived from human tumors, the presence or absence of GAF production was examined according to the method described in Example 10. Results thereof are shown in Table 13. Within the range examined, glioma cell NMC-G1 purified and stomach cancer cell AZ-521 produced released GAF in the media.

It was studied whether or not these GAF-producing human tumors were made cancerous by autocrine mechanism through GAF, and whether or not GAF neutralizing antibodies could inhibit tumor formation thereof.

TABLE 13

Measurement of GAF in Various Cell Culture Supernatants

| Tumor/Tissue/Site | Name | GAF (pg/ml) |
|---|---|---|
| Carcinoma | | |
| cervix | Hela-S3 | — |
| colon | WiDR | — |
| lung | CADO-LC3 | — |
| | Calu-1 | — |

TABLE 13-continued

Measurement of GAF in Various Cell Culture Supernatants

| Tumor/Tissue/Site | Name | GAF (pg/ml) |
|---|---|---|
| | A549 | — |
| stomach | AZ-521 | 740 |
| | NUGC-3 | — |
| | NUGC-4 | — |
| Leukemia and lymphoma | | |
| pleural effusion | U937 | — |
| bone marrow | IM-9 | — |
| | MEG-O1 | — |
| blood | J-111 | — |
| Burkitt lymphoma | Namalwa | — |
| | Raji | — |
| Sarcoma | Ret-2 | — |
| | EOS | — |
| | MG-63 | — |
| Melanoma | G-361 | — |
| Glioblastoma | NMC-G1 | 460 |
| | T98G | — |
| Lymphoblastoma | RPMI-1778 | — |
| | NC-37 | — |
| Epithelial-like amnion | WISH | — |

Results of measurement of GAF in various cell culture supernatants according to the EIA method using MoAb 13-3 and HRP-MoAb 150-59 are shown.

−: Less than the detection limit (30 pg/ml)

AZ-521 cells (2×10$^4$ cells) were plated in each well of a 24-well Limbro plate, and cultured in DMEM medium supplemented with 5% FCS containing MoAb 150-59 or MoAb 40-20 of various concentrations, in the presence or absence of 20 μg/ml of heparin for 7 days. After 7 days, the cell number was counted to examine the effect of the antibodies on growth.

As a result, MoAb 150-59 inhibited growth of the AZ-521 cells, dependent on concentration, in the presence of heparin, as shown in FIG. 28. No inhibiting action was observed in the absence of heparin. Further, MoAb 40-20 did not affected the growth of the AZ-521 cells, independently of the presence of heparin.

It was further studied whether or not anti-GAF antibodies showed anti-tumor action upon the tumor forming activity of AZ-521 in vivo.

Nude mice (female, 7 weeks old, 6 mice/group, Charles River) were subcutaneously inoculated with the AZ-521 cells (3×10$^6$ cells) cultured in vitro, and given i.v. doses of 200 μg/mouse/day of MoAb 150-59, MoAb 40-20 or normal mouse IgG, from 11 days and 18 days after inoculation for 5 days, respectively. Then, the tumor size was measured with time.

The growth rate of tumors was inhibited to about one half by administration of MoAb 150-59.

Accordingly, this proved that the anti-GAF neutralizing antibody exhibited anti-tumor action upon the GAF-producing human tumors.

FORMULATION EXAMPLE 1

| Formulation for Injection | |
|---|---|
| GAF N33 | 30 mg |
| Lactose | 170 mg |

| Formulation for Injection | |
|---|---|
| HPC—L (oxypropyl cellulose) | 10 mg |
| | Total 210 mg |

The above-mentioned components were mixed, and dissolved in water or physiological saline for injection. Human serum albumin (HSA) was added to the solution to yield a concentration of 0.5%, followed by filtration through a membrane filter (0.02 μm in pore size). Then, 1 ml portions of the resulting filtrate were separately poured into vials in a sterilized state, and lyophilized to prepare an platelet-increasing agent for injection. This formulation for injection is dissolved in 5 ml of water for injection at the time of use.

FORMULATION EXAMPLE 2

| Formulation for Injection | |
|---|---|
| GAF N33 | 30 mg |
| Lactose | 170 mg |
| Sodium lauryl sulfate | 1000 mg |
| | Total 1200 mg |

The above-mentioned components were mixed, and dissolved in water for injection or physiological saline. HSA was added to the solution to yield a concentration of 0.5%, followed by filtration through a membrane filter (0.02 μm in pore size). Then, 1 ml portions of the resulting filtrate were separately poured into vials in a sterilized state, and lyophilized to prepare an platelet-increasing agent for injection. This formulation for injection is dissolved in 5 ml of water for injection at the time of use.

What is claimed is:

1. A purified polypeptide represented by the following amino acid sequence:

(Met)n X₂ Val Thr Asp Leu Asp His Leu Lys Gly Ile Leu Arg Arg Arg Gln Leu Tyr Cys Arg Thr Gly Phe His Leu 5 Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr 10 Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser wherein n is 0 or 1; and X₂ represents Ser 15 Asp His Leu Gly Gln Ser Glu Ala Gly Gly Leu Pro Arg Gly Pro Ala or Ala (n=0, X₂=Ser Asp His Leu Gly Gln Ser Glu Ala Gly Gly Leu Pro Arg Gly Pro Ala SEQ.ID NO:6; n=0, X₂=Ala SEQ.ID NO:8; n<1, X₂=Ser Asp His Leu Gly Gln Ser Glu Ala Gly Gly Leu Pro Arg Gly Pro Ala SEQ ID NO:7; n=1, X₂=Ala SEQ.ID NO:9). 20

2. The polypeptide according to claim 1, wherein said polypeptide has the amino acid sequence as follows (SEQ ID NO: 6):

| Ser 1 | Asp | His | Leu | Gly 5 | Gln | Ser | Glu | Ala | Gly 10 | Gly | Leu | Pro | Arg | Gly 15 | Pro |
| Ala | Val | Thr | Asp 20 | Leu | Asp | His | Leu | Lys 25 | Gly | Ile | Leu | Arg | Arg 30 | Arg | Gln |
| Leu | Tyr | Cys 35 | Arg | Thr | Gly | Phe | His 40 | Leu | Glu | Ile | Phe | Pro 45 | Asn | Gly | Thr |
| Ile | Gln 50 | Gly | Thr | Arg | Lys | Asp 55 | His | Ser | Arg | Phe | Gly 60 | Ile | Leu | Glu | Phe |
| Ile 65 | Ser | Ile | Ala | Val | Gly 70 | Leu | Val | Ser | Ile | Arg 75 | Gly | Val | Asp | Ser | Gly 80 |
| Leu | Tyr | Leu | Gly | Met 85 | Asn | Glu | Lys | Gly | Glu 90 | Leu | Tyr | Gly | Ser | Glu 95 | Lys |
| Leu | Thr | Gln | Glu 100 | Cys | Val | Phe | Arg | Glu 105 | Gln | Phe | Glu | Glu | Asn 110 | Trp | Tyr |
| Asn | Thr | Tyr 115 | Ser | Ser | Asn | Leu | Tyr 120 | Lys | His | Val | Asp | Thr 125 | Gly | Arg | Arg |
| Tyr | Tyr 130 | Val | Ala | Leu | Asn | Lys 135 | Asp | Gly | Thr | Pro | Arg 140 | Glu | Gly | Thr | Arg |
| Thr 145 | Lys | Arg | His | Gln | Lys 150 | Phe | Thr | His | Phe | Leu 155 | Pro | Arg | Pro | Val | Asp 160 |
| Pro | Asp | Lys | Val | Pro 165 | Glu | Leu | Tyr | Lys | Asp 170 | Ile | Leu | Ser | Gln | Ser. 175 | |

3. The polypeptide according to claim 1, wherein said polypeptide has the amino acid sequence as follows (SEQ ID NO: 8):

| Ala 1 | Val | Thr | Asp | Leu 5 | Asp | His | Leu | Lys | Gly 10 | Ile | Leu | Arg | Arg | Arg 15 | Gln |
| Leu | Tyr | Cys | Arg 20 | Thr | Gly | Phe | His | Leu 25 | Glu | Ile | Phe | Pro | Asn 30 | Gly | Thr |
| Ile | Gln | Gly 35 | Thr | Arg | Lys | Asp | His 40 | Ser | Arg | Phe | Gly | Ile 45 | Leu | Glu | Phe |
| Ile | Ser 50 | Ile | Ala | Val | Gly | Leu 55 | Val | Ser | Ile | Arg | Gly 60 | Val | Asp | Ser | Gly |

| Leu 65 | Tyr | Leu | Gly | Met | Asn 70 | Glu | Lys | Gly | Glu | Leu 75 | Tyr | Gly | Ser | Glu | Lys 80 |
| Leu | Thr | Gln | Glu | Cys 85 | Val | Phe | Arg | Glu | Gln 90 | Phe | Glu | Glu | Asn | Trp | Tyr 95 |
| Asp | Thr | Tyr | Ser 100 | Ser | Asn | Leu | Tyr | Lys 105 | His | Val | Asp | Thr | Gly 110 | Arg | Arg |
| Tyr | Tyr | Val 115 | Ala | Leu | Asn | Lys | Asp 120 | Gly | Thr | Pro | Arg | Glu 125 | Gly | Thr | Arg |
| Thr | Lys 130 | Arg | His | Gln | Lys | Phe 135 | Thr | His | Phe | Leu | Pro 140 | Arg | Pro | Val | Asp |
| Pro 145 | Asp | Lys | Val | Pro | Glu 150 | Leu | Tyr | Lys | Asp | Ile 155 | Leu | Ser | Gln | Ser. | |

\* \* \* \* \*